United States Patent
Xu et al.

(10) Patent No.: US 11,447,490 B2
(45) Date of Patent: Sep. 20, 2022

(54) AROMATIC HETEROCYCLIC SUBSTITUTED OLEFIN COMPOUND, PREPARATION METHOD FOR SAME, PHARMACEUTICAL COMPOSITION OF SAME, AND APPLICATIONS THEREOF

(71) Applicant: SHANGHAI YINGLI PHARMACEUTICAL CO., LTD, Shanghai (CN)

(72) Inventors: Zusheng Xu, Shanghai (CN); Yangtong Lou, Shanghai (CN); Li Chen, Shanghai (CN); Kun Zeng, Shanghai (CN); Qingrui Sun, Shanghai (CN); Xiaoli Lei, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 67 days.

(21) Appl. No.: 16/964,551

(22) PCT Filed: Dec. 28, 2018

(86) PCT No.: PCT/CN2018/124667
§ 371 (c)(1),
(2) Date: Jul. 23, 2020

(87) PCT Pub. No.: WO2019/144765
PCT Pub. Date: Aug. 1, 2019

(65) Prior Publication Data
US 2021/0032242 A1    Feb. 4, 2021

(30) Foreign Application Priority Data
Jan. 24, 2018    (CN) .......................... 201810069892.9

(51) Int. Cl.
*C07D 471/04* (2006.01)
*C07D 401/06* (2006.01)

(52) U.S. Cl.
CPC ......... *C07D 471/04* (2013.01); *C07D 401/06* (2013.01)

(58) Field of Classification Search
CPC ............................ C07D 471/04; C07D 401/06
See application file for complete search history.

(56) References Cited

U.S. PATENT DOCUMENTS

| | | |
|---|---|---|
| 2004/0242615 A1 | 12/2004 | Yamamori et al. |
| 2005/0261299 A1 | 11/2005 | Kim et al. |
| 2009/0036457 A1 | 2/2009 | Yamamori et al. |
| 2010/0267731 A1 | 10/2010 | Nakamura |
| 2011/0160210 A1 | 6/2011 | Fleenor et al. |
| 2021/0032241 A1* | 2/2021 | Xu .................. A61K 31/437 |
| 2021/0300916 A1* | 9/2021 | Xu .................. A61K 31/444 |

FOREIGN PATENT DOCUMENTS

| | | | |
|---|---|---|---|
| AU | 2017302959 A1 | 3/2019 | |
| CN | 1972921 A | 5/2007 | |
| CN | 101330914 A | 12/2008 | |
| CN | 102695511 A | 9/2012 | |
| CN | 110066277 A | 7/2019 | |
| JP | 2001131151 A | 5/2001 | |
| JP | 2012193123 A | 10/2012 | |
| WO | 02094833 A1 | 11/2002 | |
| WO | 2004013135 A1 | 2/2004 | |
| WO | 2004048383 A1 | 6/2004 | |
| WO | 2009022171 A1 | 2/2009 | |
| WO | 2009133070 A1 | 11/2009 | |
| WO | 2012002680 A2 | 1/2012 | |
| WO | 2018019106 A1 | 2/2018 | |
| WO | WO-2018019106 A1 * | 2/2018 | .......... A61K 31/437 |

OTHER PUBLICATIONS

Chemical Abstracts STN Registry Database, record for RN 1322888-05-0, Entered into STN Aug. 25, 2011. (Year: 2011).*
National Center for Biotechnology Information. PubChem Compound Summary for CID 66775574, 6-(2-Pyridin-2-ylethenyl)quinoline. Create Date Nov. 30, 2012. https://pubchem.ncbi.nlm.nih.gov/compound/6-_2-Pyridin-2-ylethenyl_quinoline. (Year: 2012).*
Kim; Journal of Photoscience, 1998, 5, 69-71. (Year: 1998).*
Maryanoff; Chem. Rev. 1989, 89, 4, 863-927. (Year: 1989).*
Neuzillet; Pharmacology & Therapeutics, 2015, 147, 22-31. (Year: 2015).*
Kubiczkova; J Transl Med 2012, 10, 183. (Year: 2012).*
Rosemary; Nat Rev Drug Discov 2012, 790-811. (Year: 2012).*
Boys; Bioorg. Med. Chem. Lett. 22 (2012) 3392-3397. (Year: 2012).*
International Search Report dated Apr. 2, 2019 issued in International Patent Application No. PCT/CN2018/124667, with English translation (7 pages).
Written Opinion of the International Searching Authority dated Apr. 2, 2019 issued in International Patent Application No. PCT/CN2018/124667, with English translation (10 pages).

(Continued)

*Primary Examiner* — Daniel R Carcanague
(74) *Attorney, Agent, or Firm* — Foley & Lardner LLP

(57) ABSTRACT

Provided in the present application are an aromatic heterocyclic substituted olefin compound, a preparation method for same, a pharmaceutical composition of same, and applications thereof. The aromatic heterocyclic substituted olefin compound of the present invention is a novel ALK5 inhibitor and is for use in treating and/or preventing various ALK5-mediated diseases.

(I)

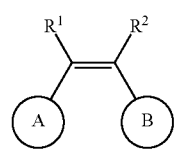

14 Claims, No Drawings

(56) References Cited

OTHER PUBLICATIONS

Search Report dated Jan. 7, 2020 issued in Chinese Patent Application No. CN2018100698929A, with English translation (5 pages).
First Office Action dated Jan. 16, 2020 issued in Chinese Patent Application No. CN2018100698929A, with English translation (10 pages).
Second Office Action dated Sep. 21, 2020 issued in Chinese Patent Application No. CN201810069892A, with English translation (10 pages).
Third Office Action dated Mar. 9, 2021 issued in Chinese Patent Application No. 201810069892.9, with English translation, 7 pages.

* cited by examiner

AROMATIC HETEROCYCLIC SUBSTITUTED OLEFIN COMPOUND, PREPARATION METHOD FOR SAME, PHARMACEUTICAL COMPOSITION OF SAME, AND APPLICATIONS THEREOF

The present application is a 371 of PCT/CN2018/124667, filed on Dec. 28, 2018, which claims the right of priority to Chinese patent application CN 201810069892.9, filed on Jan. 24, 2018, the contents of which are incorporated herein by reference in their entireties.

TECHNICAL FIELD

The present invention relates to an aromatic heterocyclic substituted olefin compound, a preparation method for same, a pharmaceutical composition of same, and applications thereof.

BACKGROUND ARTS

Transforming growth factor-β (TGF-β) is a multifunctional cytokine that participates in the regulation of cell proliferation, differentiation and apoptosis through complex receptor signaling pathways on cell surface in manners of autocrine, paracrine, and endocrine. TGF-β and activins, inhibins, bone morphogenetic proteins, and Mullerian-inhibiting substance and other related proteins belong to the transforming growth factor β superfamily (TGF-β superfamily, TGF-βs).

TGF-β has 3 main cell receptors: type I, type II and type III receptors. Type I and type II receptors are transmembrane serine/threonine kinases, both of which transmit information at the same time. Type III receptors do not transmit information, the function of which is mainly to transmit TGF-β to type II receptors, and to indirectly affect signal transduction through providing ligands for receptor II.

The signaling pathway of TGF-β is mainly TGF-β-Smad signaling pathway. The Smad protein family is an intracellular signal transduction protein discovered in recent years, and it is known that there are 8 kinds of Smad protein molecules in the human body. After the activation of TGF-β in the form of an inactive protein complex, TGF-β interacts with type II receptor (TGFβR II) and type I receptor (TGFβR I, also known as ALK5 (activin-like kinase 5)) on the cell surface to form a double dimer receptor complex. Type II receptor phosphorylates and activates type I receptor. Then type I receptor phosphorylates the Smad protein molecule (Smad2/3) to which it is attached and releases it into the cytoplasm, forms a complex with Smad4 protein and transfers it to the nucleus, thereby combining different transcription factors and transcription co-activators or transcription co-inhibitors to regulate the transcription of TGF-β target genes and produce biological effects. The TGF-β-Smad signaling pathway has important regulatory effects on cell proliferation, differentiation, apoptosis, attachment and migration, synthesis of extracellular matrix, wound repair, and immune function (Nature 2003, 425, 577). Studies have shown that abnormal TGF-β signaling is associated with many diseases, such as cancer, renal fibrosis, liver fibrosis, lung fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, arteriosclerosis, and tumor metastasis and growth. An important node TGFβR I (ALK5) of the TGF-β signaling pathway is an ideal target for the treatment of these diseases. By inhibiting ALK5 phosphorylation of its downstream signal Smad2 or Smad3, blocking or partially blocking the transmission of TGF-β signal into the cell, thereby correcting the abnormal TGF-β signal, it can treat and prevent various ALK5-mediated diseases (Nat Rev Drug Discov. 2012 Oct., 11(10): 790-811; Pharmacology & Therapeutics 147 (2015) 22-31).

The prior art has disclosed some compounds as ALK5 inhibitors, for example: WO 2012002680, WO 2009022171, WO 2009133070, WO 2004048383, WO 2004013135, WO 2002094833, etc.

The inventors have discovered through research that a class of aromatic heterocyclic substituted olefin compounds can be used as ALK5 inhibitors and is useful in treating and/or preventing various ALK5-mediated diseases.

Content of the Present Invention

The present invention provides an aromatic heterocyclic substituted olefin compound, a preparation method for same, a pharmaceutical composition of same, and applications thereof. The aromatic heterocyclic substituted olefin compound of the present invention is a novel ALK5 inhibitor and is for use in treating and/or preventing various ALK5-mediated diseases.

The present invention provides an aromatic heterocyclic substituted olefin compound represented by general formula I or a pharmaceutically acceptable salt thereof:

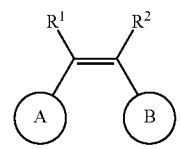

wherein ring A and ring B are located on the same side of the double bond;

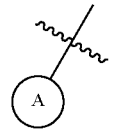

is

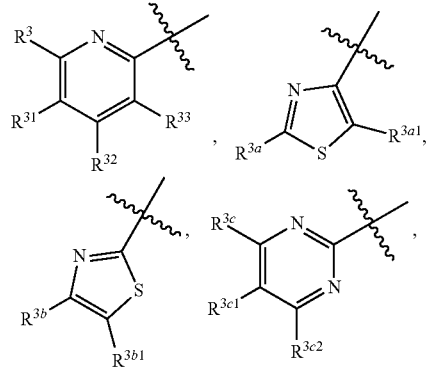

-continued

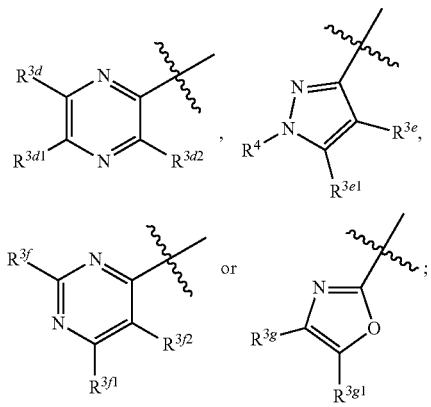

is

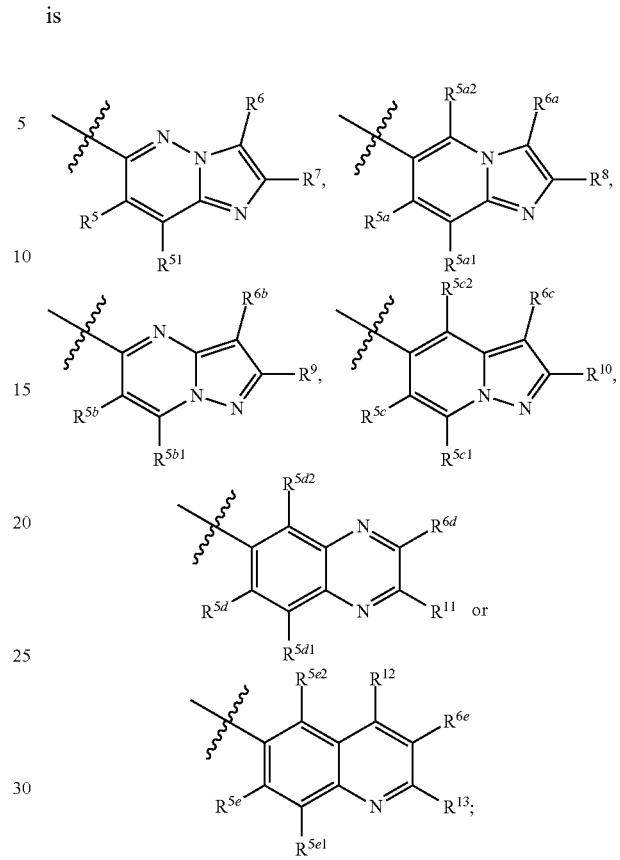

$R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —$NR^{a3}R^{a4}$, —$OR^{35}$, —$SR^{a6}$, —$C(O)OR^{a7}$, —$C(O)NR^{a8}R^{a9}$, —$COR^{a10}$, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{4-8}$ cycloalkenyl, substituted or unsubstituted $C_{6-20}$ aryl, or substituted or unsubstituted $C_{2-10}$ heteroaryl; wherein $R^{a3}$, $R^{a4}$, $R^{a5}$, $R^{a6}$, $R^{a7}$, $R^{a8}$, $R^{a9}$ and $R^{a10}$ are each independently hydrogen, substituted or unsubstituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl; $R^{a3}$ and $R^{a8}$ can also be independently hydroxyl or $C_{1-6}$ alkoxy;

substituents in the substituted $C_{1-6}$ alkyl in $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$, $R^{3g1}$, $R^{a3}$, $R^{a4}$, $R^{a5}$, $R^{a6}$, $R^{a7}$, $R^{a8}$, $R^{a9}$ and $R^{a10}$, and substituents in the substituted $C_{2-8}$ alkenyl, substituted $C_{2-8}$ alkynyl, substituted $C_{3-10}$ cycloalkyl, substituted $C_{2-8}$ heterocycloalkyl, substituted $C_{4-8}$ cycloalkenyl, substituted $C_{6-20}$ aryl, and substituted $C_{3-10}$ heteroaryl in $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{a15}$, —$SR^{a16}$, —$C(O)OR^{a17}$, —$COR^{a18}$, —$C(O)NH_2$, $C_{3-10}$ cycloalkyl, $C_{2-8}$ heterocycloalkyl, $C_{6-20}$ aryl or $C_{2-10}$ heteroaryl; $R^{a15}$, $R^{a16}$, $R^{a17}$ and $R^{a18}$ are each independently hydrogen or $C_{1-6}$ alkyl; when there are multiple substituents, the substituents are the same or different;

$R^4$ is hydrogen, cyano, $C_{1-6}$ alkyl, $C_{3-10}$ cycloalkyl, $C_{2-8}$ heterocycloalkyl, —$C(O)OR^{a19}$ or $C_{1-6}$ alkyl substituted with —$OR^{a20}$; $R^{a19}$ and $R^{a20}$ are each independently $C_{1-6}$ alkyl;

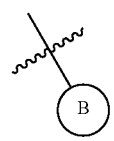

$R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are each independently hydrogen, deuterium or halogen;

$R^6$, $R^{6a}$, $R^{6b}$, $R^{6c}$, $R^{6d}$ and $R^{6e}$ are each independently hydrogen, deuterium, halogen, sulfonyl, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, substituted or unsubstituted $C_{2-10}$ heteroaryl, cyano, —$OR^{61}$, —$SR^{62}$, —$NR^{a63}R^{a64}$, —$C(O)R^{65}$, —$C(O)OR^{66}$, —$OC(O)R^{67}$, —$OC(O)OR^{68}$, —$C(O)NR^{a69}R^{a610}$, —$N(R^{611})C(O)R^{612}$, —$S(O)R^{613}$, —$S(O)_2R^{614}$, —$S(O)_2NR^{a615}R^{a616}$, —$OC(O)NR^{a617}R^{a618}$, —$N(R^{619})C(O)OR^{620}$, —$N(R^{621})C(O)NR^{a622}R^{a623}$, —$N(R^{624})S(O)_2R^{625}$ or —$OP(O)(OR^{626})_2$;

$R^{61}$, $R^{62}$, $R^{a64}$, $R^{65}$, $R^{66}$, $R^{67}$, $R^{68}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are each independently hydrogen, substituted or unsubstituted $C_{1-6}$ alkyl, substituted or unsubstituted $C_{2-5}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

$R^{a63}$ and $R^{a69}$ are each independently hydrogen, hydroxyl, Cue alkoxy, substituted or unsubstituted $C_{1-6}$ alkyl, substituted or unsubstituted $C_{2-5}$ alkenyl, substituted or unsubstituted $C_{2-8}$ alkynyl, Substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

in $R^6$, $R^{6a}$, $R^{6b}$, $R^{6c}$, $R^{6d}$ and $R^{6e}$, substituents in the substituted $C_{1-6}$ alkyl, substituted $C_{2-8}$ alkenyl, substituted $C_{2-5}$ alkynyl, substituted $C_{3-10}$ cycloalkyl, substituted $C_{2-5}$ heterocycloalkyl, substituted $C_{6-20}$ aryl, and substituted $C_{3-10}$ heteroaryl are each independently one or more of the following groups: deuterium, halogen, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{3-10}$ heteroaryl, cyano, —OR$^{71}$, —SR$^{72}$, —NR$^{a73}$R$^{a74}$, —C(O)R$^{75}$, —C(O)OR$^{76}$, —OC(O)R$^{77}$, —OC(O)OR$^{78}$, —C(O)NR$^{a79}$R$^{a710}$, —N(R$^{711}$)C(O)R$^{712}$, S(O)R$^{713}$, —S(O)$_2$R$^{714}$, —S(O)$_2$NR$^{a715}$R$^{a716}$, —OC(O)NR$^{a717}$R$^{a718}$, —N(R$^{719}$)C(O)OR$^{720}$, —N(R$^{721}$)C(O)NR$^{a722}$R$^{a723}$, —N(R$^{724}$)S(O)$_2$R$^{725}$ or —OP(O)(OR$^{726}$)$_2$; when there are multiple substituents, the substituents are the same or different; R$^{71}$, R$^{72}$, R$^{a73}$, R$^{a74}$, R$^{75}$, R$^{76}$, R$^{77}$, R$^{78}$, R$^{a79}$, R$^{a710}$, R$^{711}$, R$^{712}$, R$^{713}$, R$^{714}$, R$^{a715}$, R$^{a716}$, R$^{a717}$, R$^{a718}$, R$^{719}$, R$^{720}$, R$^{721}$, R$^{a722}$, R$^{a723}$, R$^{724}$, R$^{725}$ and R$^{726}$ are each independently deuterium, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{3-10}$ heteroaryl;

in R$^{61}$, R$^{62}$, R$^{a63}$, R$^{a64}$, R$^{65}$, R$^{66}$, R$^{67}$, R$^{68}$, R$^{a69}$, R$^{a610}$, R$^{611}$, R$^{612}$, R$^{613}$, R$^{614}$, R$^{a615}$, R$^{a616}$ R$^{a617}$, R$^{a618}$, R$^{619}$, R$^{620}$, R$^{621}$, R$^{a622}$, R$^{a623}$, R$^{624}$, R$^{625}$ and R$^{626}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl or substituted $C_{2-10}$ heteroaryl are one or more of the following groups: deuterium, halogen, cyano, Cue alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, —OR$^c$, —SR$^{c1}$, —NR$^{b1}$R$^{b2}$, —C(O)R$^{c2}$, —C(O)OR$^{c3}$, —OC(O)R$^{c4}$, —OC(O)OR$^{c5}$, —C(O)NR$^{b3}$R$^{b4}$, —N(R$^{c6}$)C(O)OR$^{c7}$, S(O)R$^{c8}$, —S(O)$_2$R$^{c9}$, —S(O)$_2$NR$^{b5}$R$^{b6}$, —N(R$^{c10}$)C(O)R$^{c11}$, —N(R$^{c12}$)C(O)NR$^{b7}$R$^{b8}$ or —N(R$^{c13}$)S(O)$_2$R$^{c14}$; R$^c$, R$^{c1}$, R$^{b1}$, R$^{b2}$, R$^{c2}$, R$^{c3}$, R$^{c4}$, R$^{c5}$, R$^{b3}$, R$^{b4}$, R$^{c6}$, R$^{c7}$, R$^{c8}$, R$^{c9}$, R$^{b5}$, R$^{b6}$, R$^{c10}$, R$^{c11}$, R$^{c12}$, R$^{b7}$, R$^{b8}$, R$^{c13}$ and R$^{c14}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

R$^7$, R$^8$, R$^9$, R$^{10}$, R$^{11}$, R$^{12}$ and R$^{13}$ are each independently hydrogen, deuterium or halogen; one of R$^1$ and R$^2$ is hydrogen, deuterium, halogen, or substituted or unsubstituted $C_{1-6}$ alkyl, and the other is hydrogen, deuterium, halogen, cyano, sulfonyl, substituted or unsubstituted $C_{1-6}$ alkyl, —C(O)OR$^{91}$, —COR$^{92}$,

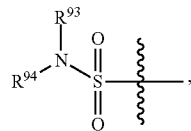

—S(O)R$^{95}$, —S(O)$_2$R$^{96}$, —C(O)NR$^{97}$R$^{98}$, or substituted or unsubstituted $C_{2-10}$ heteroaryl; in R$^1$ and R$^2$, substituents in the substituted $C_{1-6}$ alkyl and the substituted $C_{2-10}$ heteroaryl are each independently one or more of the following groups: deuterium, halogen, cyano, $C_{1-6}$ alkyl, $C_{2-8}$ alkenyl, $C_{2-8}$ alkynyl, —OR$^{920}$, —SR$^{921}$, —C(O)OR$^{922}$, —COR$^{923}$, —C(O)NH$_2$, —NR$^{924}$R$^{925}$, $C_{3-10}$ cycloalkyl, $C_{2-8}$ heterocycloalkyl, $C_{1-6}$ aryl or $C_{2-10}$ heteroaryl; R$^{920}$, R$^{921}$, R$^{922}$, R$^{923}$, R$^{924}$ and R$^{925}$ are each independently hydrogen or $C_{1-6}$ alkyl;

R$^{91}$, R$^{92}$, R$^{93}$ and R$^{94}$ are independently one or more of the following groups: hydrogen, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{1-6}$ aryl or $C_{2-10}$ heteroaryl; R$^{95}$ and R$^{96}$ are independently hydrogen or $C_{1-6}$ alkyl;

R$^{97}$ and R$^{98}$ are independently hydroxyl, hydrogen, substituted or unsubstituted Cue alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

in R$^{97}$ and R$^{98}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl, and substituted $C_{2-10}$ heteroaryl are each independently one or more of the following groups: deuterium, halogen, cyano, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, —OR$^{101}$, —SR$^{102}$, —NR$^{b103}$R$^{b104}$, —C(O)R$^{105}$, —C(O)OR$^{106}$, —OC(O)R$^{107}$, —OC(O)OR$^{108}$, —C(O)NR$^{b109}$R$^{b1010}$, —N(R$^{1011}$)C(O)OR$^{1012}$, S(O)R$^{1013}$, —S(O)$_2$R$^{1014}$, —S(O)$_2$NR$^{b1015}$R$^{b1016}$, —N(R$^{1017}$)C(O)OR$^{1018}$, —OC(O)NR$^{b1019}$R$^{b1020}$, or —N(R$^{1021}$)S(O)$_2$R$^{1022}$; when there are multiple substituents, the substituents are the same or different; R$^{101}$, R$^{102}$, R$^{b103}$, R$^{b104}$, R$^{105}$, R$^{106}$, R$^{107}$, R$^{108}$, R$^{b109}$, R$^{b1010}$, R$^{1011}$, R$^{1012}$, R$^{1013}$, R$^{1014}$, R$^{b1015}$, R$^{b1016}$, R$^{1017}$, R$^{1018}$, R$^{b1019}$, R$^{b1020}$, R$^{1021}$ and R$^{1022}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

or R$^1$ and R$^2$ together with the carbon atom to which they are attached form substituted or unsubstituted 4-8 membered carbocycle containing a double bond, or a substituted or unsubstituted 4-8 membered heterocycle, and the heteroatoms in the 4-8 membered heterocycle are one or more of O, S and N, and the number of the heteroatoms is 1, 2, 3 or 4;

substituents in the substituted 4-8 membered carbocycle and the substituted 4-8 membered heterocycle are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —OR$^{111}$, —SR$^{112}$, —C(O)OR$^{113}$, —COR$^{114}$, —C(O)NH$_2$, $C_{3-10}$ cycloalkyl, $C_{2-8}$ heterocycloalkyl, $C_{6-20}$ aryl or $C_{2-10}$ heteroaryl; R$^{111}$, R$^{112}$, R$^{113}$ and R$^{114}$ are each independently hydrogen or $C_{1-6}$ alkyl;

in each of the above letters and groups, the heteroatoms in the substituted or unsubstituted $C_{2-8}$ heterocycloalkyl or the $C_{2-8}$ heterocycloalkyl are one or more of N, O and S, and the number of the heteroatoms is 1, 2, 3 or 4; the heteroatoms in the substituted or unsubstituted $C_{2-10}$ heteroaryl or the $C_{3-10}$ heteroaryl are one or more of N, O and S, and the number of the heteroatoms is 1, 2, 3 or 4; when there are multiple heteroatoms, the heteroatoms are the same or different;

or in the above groups or substituents, when NR$^X$R$^Y$ is present, then R$^X$ and R$^Y$ together with the nitrogen atom to which they are attached form substituted or unsubstituted 3-8 membered heterocyclyl; the heteroatoms in the 3-8 membered heterocyclyl are N, N and O, N and S, or N, O and S; the number of the heteroatoms is 1, 2, 3 or 4; the substituents in the substituted 3-8 membered heterocyclyl are one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —OR$^{a81}$, —SR$^{a82}$, —C(O)OR$^{a83}$, —COR$^{a84}$, —C(O)NH$_2$, $C_{3-10}$ cycloalkyl, $C_{2-8}$ heterocycloalkyl, $C_{6-20}$ aryl or $C_{2-10}$ heteroaryl; R$^{a81}$, R$^{a82}$, R$^{a83}$ and R$^{a84}$ are each independently hydrogen or $C_{1-6}$ alkyl.

In a preferred embodiment of the present invention, when

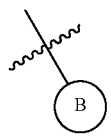

is

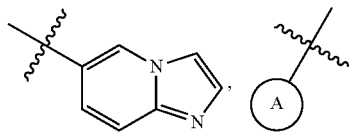

is not

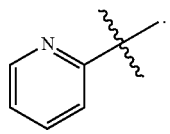 [SMILES: *c1ccccn1]

In the present invention, —NR$^X$R$^Y$ is for example: NR$^{a3}$R$^{a4}$, —NR$^{a8}$R$^{a9}$, —NR$^{a63}$R$^{a64}$, —NR$^{a69}$R$^{a610}$, —NR$^{a615}$R$^{a616}$, —NR$^{a617}$R$^{a618}$, NR$^{a622}$R$^{a623}$, —NR$^{a73}$R$^{a74}$, —NR$^{a79}$R$^{a710}$, —NR$^{a715}$R$^{a716}$, —NR$^{a717}$R$^{a718}$, —NR$^{a722}$R$^{a723}$, —NR$^{b1}$R$^{b2}$, —NR$^{b3}$R$^{b4}$, —NR$^{b5}$R$^{b6}$, —NR$^{b7}$R$^{b8}$, —NR$^{93}$R$^{94}$, —NR$^{97}$R$^{98}$, —NR$^{924}$R$^{925}$, —NR$^{b103}$R$^{b104}$, —NR$^{b109}$R$^{b1010}$, —NR$^{b1015}$R$^{b1016}$ or —NR$^{b1019}$R$^{b1020}$.

In the present invention, the term $C_{1-6}$ alkyl in the substituted or unsubstituted $C_{1-6}$ alkyl and the term $C_{1-6}$ alkyl are independently $C_{1-4}$ alkyl. The $C_{1-4}$ alkyl is preferably methyl, ethyl, n-propyl, isopropyl, n-butyl, isobutyl, or tert-butyl.

In the present invention, the term $C_{2-8}$ alkenyl in the substituted or unsubstituted $C_{2-8}$ alkenyl and the term $C_{2-8}$ alkenyl are independently preferably $C_{2-4}$ alkenyl. The $C_{2-4}$ alkenyl is preferably vinyl, propenyl, allyl,

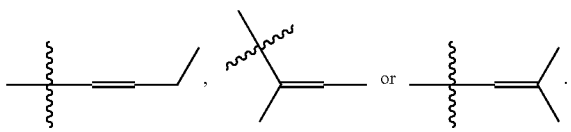

In the present invention, the term $C_{2-8}$ alkynyl in the substituted or unsubstituted $C_{2-8}$ alkynyl and the term $C_{2-8}$ alkynyl are independently preferably $C_{2-4}$ alkynyl. The $C_{2-4}$ alkynyl is preferably ethynyl, propynyl, butynyl or 3-methylpropynyl.

In the present invention, the term $C_{3-10}$ cycloalkyl in the substituted or unsubstituted $C_{3-10}$ cycloalkyl and the term $C_{3-10}$ cycloalkyl are independently preferably cyclopropyl, cyclobutyl, cyclopentyl, cyclohexyl, cycloheptyl, cyclooctyl, cyclononyl, cyclodecyl or bicyclic cycloalkyl such as bicyclo[3.1.1]heptyl, bicyclo[2.2.1]heptyl, bicyclo[2.2.2]octyl, Bicyclo[3.2.2]nonyl, bicyclo[3.3.1]nonyl or bicyclo[4.2.1]nonyl.

In the present invention, the term $C_{2-8}$ heterocycloalkyl in the substituted or unsubstituted $C_{2-8}$ heterocycloalkyl and the term $C_{2-8}$ heterocycloalkyl are independently preferably azetidinyl, azepanyl, aziridine, diazacycloheptyl, 1,3-dioxanyl, 1,3-dioxopenyl, 1,3-dithiopentyl, 1,3-dithianyl, imidazolinyl, imidazolidinyl, isothiazolidinyl, isothiazolyl, isoxazolinyl, morpholinyl, oxadiazolinyl, oxadiazole alkyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxothiomorpholinyl, thiopyranyl, trithianyl, 2,3-dihydrobenzofuran-2-yl, 2,3-dihydrobenzofuran-3-yl, dihydroindole-1-yl, indoline-2-yl, dihydroindole-3-yl, 2,3-dihydrobenzothiophen-2-yl, decahydroquinolinyl, decahydroisoquinolinyl, octahydro-1H-indolyl or octahydrobenzofuranyl.

In the present invention, the term $C_{4-8}$ cycloalkenyl in the substituted or unsubstituted $C_{4-8}$ cycloalkenyl and the term $C_{4-8}$ cycloalkenyl are independently preferably cyclobutenyl, cyclopentenyl, cyclohexenyl, cycloheptenyl, cyclooctenyl, norbornenyl or bicyclo[2.2.2]octenyl.

In the present invention, the term $C_{6-20}$ aryl in the substituted or unsubstituted $C_{6-20}$ aryl or the term $C_{6-20}$ aryl is independently preferred phenyl, naphthyl, anthryl, phenanthryl, azulenyl, indan-1-yl, indan-2-yl, indan-3-yl, indan-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalene-2-yl, dihydronaphthalene-3-yl, dihydronaphthalene-4-yl, dihydronaphthalene-1-yl, 5,6,7,8-tetrahydronaphthalene-1-yl, 5,6,7,8-tetrahydronaphthalene-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-benzofuran-2-one-5-yl, 2H-benzofuran-2-one-6-yl, 2H-benzofuran-2-one-7-yl, 2H-benzofuran-2-one-8-yl, isoindoline-1,3-dione-4-yl, isoindoline-1,3-dione-5-yl, inden-1-one-4-yl, inden-1-one-5-yl, inden-1-one-6-yl, inden-1-one-7-yl, 2,3-dihydrobenzo[b][1,4]dioxan-5-yl, 2,3-dihydrobenzo[b][1,4]dioxan-6-yl, 2H-benzo[b][1,4]oxazepine 3(4H)-keto-5-yl, 2H-benzo[b][1,4]oxazepine 3(4H)-one-6-yl, 2H-benzo[b][1,4]oxazepine 3(4H)-keto-7-yl, 2H-benzo[b][1,4]oxazepine 3(4H)-one-8-yl, benzo[d]oxazepine-2(3H)-one-5-yl, benzo[d]oxazepine-2(3H)-one-6-yl, benzo[d]oxazepine-2(3H)-one-7-yl, benzo[d]oxazepine-2(3H)-one-8-yl, quinazoline-4(3H)-one-5-yl, quinazoline-4(3H)-one-6-yl, quinazoline-4(3H)-one-7-yl, quinazoline-4(3H)-one-8-yl, quinoxaline-2(1H)-one-5-yl, quinoxaline-2(1H)-one-6-yl, quinoxaline-2(1H)-one-7-yl, quinoxaline-2(1H)-one-8-yl, benzo[d]thiazole-2(3H)-one-4-yl, benzo[d]thiazole-2(3)-one-5-yl, benzo[d]thiazole-2(3H)-one-6-yl or benzo[d]thiazole-2(3H)-one-7-yl.

In the present invention, the term $C_{2-10}$ heteroaryl in the substituted or unsubstituted $C_{2-10}$ heteroaryl and the term $C_{2-10}$ heteroaryl are independently preferably furanyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzothiazolyl, cinnolinyl, 5,6-dihydroquinolin-2-yl, 5,6-dihydroquinolin-1-yl, furopyridinyl, indazolyl, indolyl, isoquinolinyl, naphthyridinyl, purinyl, quinolinyl, 5,6,7,8-tetrahydroquinoline-2-yl, 5,6,7,8-tetrahydroquinoline-3-yl, 5,6,7,8-tetrahydroquinoline-4-yl, 5,6,7,8-tetrahydroisoquinoline-1-yl, thienopyridyl, 4,5,6,7-tetrahydro[c][1,2,5]oxadiazolyl or 6,7-dihydropyro [c][1,2,5]oxadiazole-4(5H)keto.

In a preferred embodiment of the present invention, one of $R^1$ and $R^2$ is hydrogen, or substituted or unsubstituted $C_{1-6}$ alkyl, and the other is hydrogen, cyano, sulfonyl, substituted or unsubstituted $C_{1-6}$ alkyl, —C(O)OR$^{91}$, —COR$^{92}$,

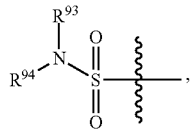

—S(O)R$^{95}$, —S(O)$_2$R$^{96}$, —C(O)NR$^{97}$R$^{98}$, or substituted or unsubstituted $C_{2-10}$ heteroaryl; or $R^1$ and $R^2$ together with the carbon atom to which they are attached form substituted or unsubstituted 4-8 membered carbocycle containing a double bond, or a substituted or unsubstituted 4-8 membered heterocycle; wherein, definitions of R$^{91}$, R$^{92}$, R$^{93}$, R$^{94}$, R$^{95}$, R$^{96}$, R$^{97}$ and R$^{98}$ are the same as described above; definitions of the substitutions in the substituted $C_{1-6}$ alkyl, the substituted $C_{2-10}$ heteroaryl, the substituted 4-8 membered carbocycle and the substituted 4-8 membered heterocycle are the same as described above.

In a preferred embodiment of the present invention, one of $R^1$ and $R^2$ is hydrogen, and the other is hydrogen, cyano, substituted or unsubstituted $C_{1-6}$ alkyl, —C(O)OR$^{91}$ or —C(O)NR$^{97}$R$^{98}$; or $R^1$ and $R^2$ together with the carbon atom to which they are attached form substituted or unsubstituted 4-8 membered carbocycle containing a double bond; wherein $R^{91}$ is hydrogen or $C_{1-6}$ alkyl; $R^{97}$ and $R^{98}$ are independently hydrogen, or substituted or unsubstituted $C_{1-6}$ alkyl; or $R^{97}$ and $R^{98}$ together with the nitrogen atom to which they are attached form substituted or unsubstituted 3-8 membered heterocyclyl; wherein in $R^1$ or $R^2$, definitions of the substitutions in the substituted $C_{1-6}$ alkyl, the substituted 4-8 membered carbocycle and the substituted 4-8 membered heterocycle are the same as described above; in $R^{97}$ or $R^{98}$, definitions of the substituents in the substituted $C_{1-6}$ alkyl or the substituted 3-8 membered heterocyclyl are the same as described in above.

In a preferred embodiment of the present invention, one of $R^1$ and $R^2$ is hydrogen, and the other is hydrogen, $C_{1-6}$ alkyl, —C(O)OR$^{91}$ or —C(O)NR$^{97}$R$^{98}$; or $R^1$ and $R^2$ together with the carbon atom to which they are attached form 4-8 membered carbocycle containing a double bond; wherein $R^{91}$, $R^{97}$ and $R^{98}$ are independently hydrogen or $C_{1-6}$ alkyl; or $R^{97}$ and $R^{98}$ together with the nitrogen atom to which they are attached form 3-8 membered heterocyclyl; Preferably, $R^1$ is hydrogen, and $R^2$ is hydrogen, $C_{1-6}$ alkyl, —C(O)OR$^{91}$ or —C(O)NR$^{97}$R$^{98}$; R$^{91}$, R$^{97}$ and R$^{98}$ are independently hydrogen or $C_{1-6}$ alkyl.

In a preferred embodiment of the present invention, $R^1$ and $R^2$ are both hydrogen;

Or $R^1$ is hydrogen and $R^2$ is

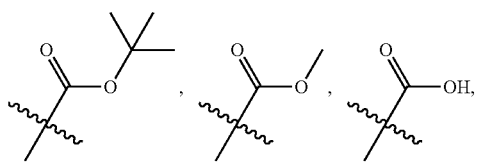

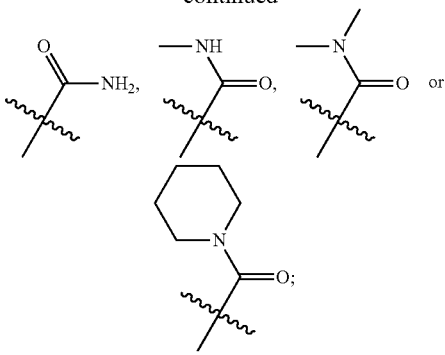

or $R^1$ and $R^2$ together with the carbon atom to which they are attached form cyclohexene.

In a preferred embodiment of the present invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —NR$^{a3}$R$^{a4}$, —OR$^{a5}$, —SR$^{a6}$, —C(O)OR$^{a7}$, —C(O)NR$^{a8}$R$^{a9}$, —COR$^{a10}$, substituted or unsubstituted $C_{1-6}$ alkyl, substituted or unsubstituted $C_{2-8}$ heterocycloalkyl, substituted or unsubstituted $C_{6-20}$ aryl, or substituted or unsubstituted $C_{2-10}$ heteroaryl; wherein, the definitions of R$^{a3}$, R$^{a4}$, R$^{a5}$, R$^{a6}$, R$^{a7}$, R$^{a8}$, R$^{a9}$ and R$^{a10}$ are the same as described above; definitions of the substitutions in the substituted $C_{1-6}$ alkyl, substituted $C_{2-8}$ heterocycloalkyl, substituted $C_{6-20}$ aryl or substituted $C_{2-10}$ heteroaryl are the same as described above.

In a preferred embodiment of the present invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, —OR$^{a5}$, or substituted or unsubstituted $C_{1-6}$ alkyl;

$R^{a5}$ is $C_{1-6}$ alkyl; the substituents in the substituted $C_{1-6}$ alkyl are one or more of the following groups: deuterium or halogen.

In a preferred embodiment of the present invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, trifluoromethyl, difluoromethyl, methyl, deuterated methyl or methoxy.

In a preferred embodiment of the present invention, 1 or 2 positions in ring A are not hydrogen.

In a preferred embodiment of the present invention, ring A is preferably

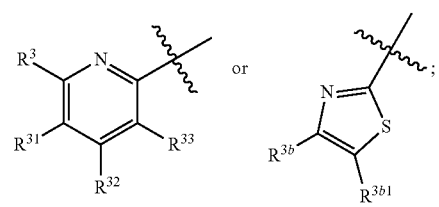

wherein $R^3$ and $R^{33}$ are independently preferably hydrogen, halogen, —OR$^{a5}$, or substituted or unsubstituted $C_{1-6}$ alkyl, but not hydrogen at the same time; $R^{3b}$ is hydrogen, halogen, —OR$^{a5}$, or substituted or unsubstituted $C_{1-6}$ alkyl; a definition of $R^{a5}$ is the same as described above; definitions of the substitutions in the substituted $C_{1-6}$ alkyl are the same as described above; $R^{31}$, $R^{32}$ and $R^{3b1}$ are hydrogen.

In a preferred embodiment of the present invention,

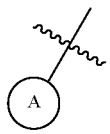

is preferably

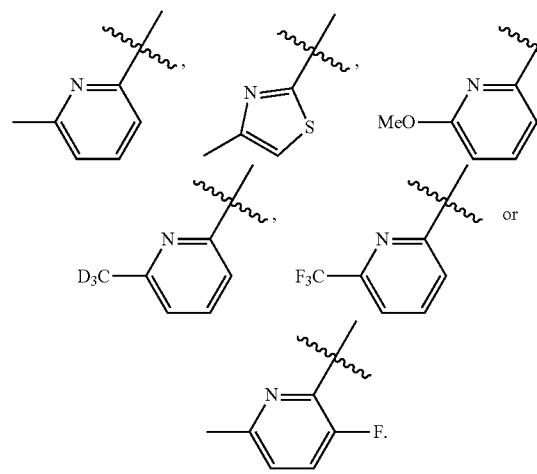

In a preferred embodiment of the present invention, $R^4$ is hydrogen, $C_{1-6}$ alkyl or $C_{3-10}$ cycloalkyl.

In a preferred embodiment of the present invention, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are hydrogen.

In a preferred embodiment of the present invention, $R^6$, $R^{6a}$, $R^{6b}$, $R^{6c}$, $R^{6d}$ and $R^{6e}$ are each independently hydrogen, halogen, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, cyano, —OR61, —SR62, —NRa63R$^{a64}$, —C(O)R$^{65}$, —C(O)OR$^{66}$, —OC(O)R$^{67}$, —OC(O)OR$^{68}$, —C(O)NR$^{a69}$R$^{a610}$, —N(R$^{611}$)C(O)R$^{612}$, —S(O)R$^{613}$, —S(O)$_2$R$^{614}$, —S(O)$_2$NR$^{a615}$R$^{a616}$, —OC(O)NR$^{a617}$R$^{a618}$, —N(R$^{619}$)C(O)OR$^{620}$, —N(R$^{621}$)C(O)NR$^{a622}$R$^{a623}$, —N(R$^{624}$)S(O)$_2$R$^{625}$ or —OP(O)(OR$^{626}$)$_2$; definitions of $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are the same as described above; definitions of the substitutions in the substituted $C_{1-6}$ alkyl, substituted $C_{2-5}$ heterocycloalkyl, substituted $C_{6-20}$ aryl or substituted $C_{2-10}$ heteroaryl are the same as described above.

In a preferred embodiment of the present invention, $R^6$, $R^{6a}$, $R^{6b}$, $R^{6c}$, $R^{6d}$ and $R^{6e}$ are each independently hydrogen, halogen, cyano, substituted or unsubstituted $C_{1-6}$ alkyl, substituted or unsubstituted $C_{2-5}$ heterocycloalkyl, substituted or unsubstituted $C_{6-20}$ aryl, substituted or unsubstituted $C_{3-10}$ heteroaryl, cyano, —OR$^{61}$, —SR$^{62}$, —C(O)R$^{65}$, —C(O)OR$^{66}$ or —C(O)NR$^{a69}$R$^{a610}$; definitions of $R^{61}$, $R^{62}$, $R^{65}$, $R^{66}$, $R^{a69}$ and $R^{a610}$ are the same as described above; definitions of the substitutions in the substituted $C_{1-6}$ alkyl, substituted $C_{2-8}$ heterocycloalkyl, substituted $C_{6-20}$ aryl or substituted $C_{3-10}$ heteroaryl are the same as described above.

In a preferred embodiment of the present invention, $R^6$, $R^{6a}$, $R^{6b}$, $R^{6c}$, $R^{6d}$ and $R^{6e}$ are each independently cyano, —C(O)OR$^{66}$ or —C(O)NR$^{a69}$R$^{a610}$; $R^{66}$ is preferably $C_{1-6}$ alkyl; $R^{a69}$ and $R^{a610}$ are each independently hydrogen, substituted or unsubstituted $C_{1-6}$ alkyl, substituted or unsubstituted $C_{3-10}$ cycloalkyl or —OR$^{627}$; definitions of the substitutions in the substituted $C_{1-6}$ alkyl or the substituted $C_{3-10}$ cycloalkyl are the same as described above; a definition of $R^{627}$ is the same as described above.

In a preferred embodiment of the present invention, $R^6$, $R^{6a}$, $R^{6b}$, $R^{6c}$, $R^{6d}$ and $R^{6e}$ are each independently cyano, —C(O)OR$^{66}$ or —C(O)NR$^{a69}$R$^{a610}$; $R^{66}$ is $C_{1-6}$ alkyl; $R^{a69}$ and $R^{a610}$ are each independently hydrogen, substituted or unsubstituted $C_{1-6}$ alkyl, $C_{3-10}$ cycloalkyl or —OR$^{627}$; the substituents in the substituted $C_{1-6}$ alkyl are preferably $C_{2-5}$ heterocycloalkyl

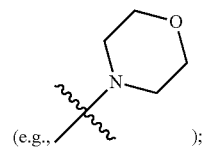

(e.g., );

$R^{627}$ is preferably $C_{2-5}$ heterocycloalkyl

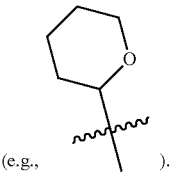

(e.g., ).

In a preferred embodiment of the present invention, $R^6$, $R^{6a}$, $R^{6b}$, $R^{6c}$, $R^{6d}$ and $R^{6e}$ are independently —C(O)NR$^{a69}$R$^{a610}$; definitions of $R^{a69}$ and $R^{a610}$ are the same as described above.

In a preferred embodiment of the present invention, $R^6$, $R^{6a}$, $R^{6b}$, $R^{6c}$, $R^{6d}$ and $R^{6e}$ are each independently CN, —C(=O)NH$_2$, —C(=O)(OEt),

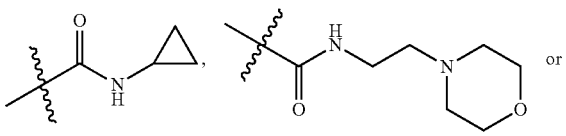

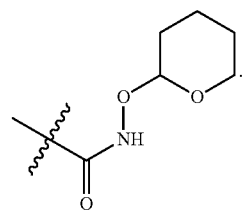

In a preferred embodiment of the present invention, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen.

In a preferred embodiment of the present invention,

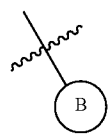

is preferably

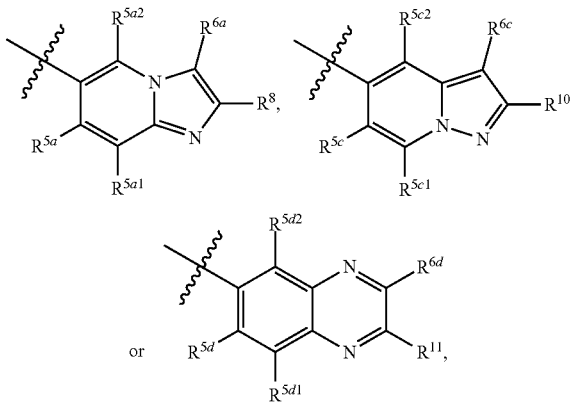

and further preferably

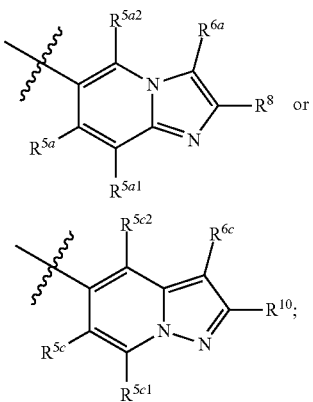

wherein $R^{5a}, R^{5a1}, R^{5a2}, R^{5c}, R^{5c1}, R^{5c2}, R^{5d}, R^{5d1}, R^{5d2}, R^8, R^{10}$ and $R^{11}$ are preferably hydrogen; $R^{6a}, R^{6c}$ and $R^{6d}$ are each independently cyano, $C_{2-10}$ heteroaryl, —C(O)OR$^{66}$ or —C(O)NR$^{a69}$R$^{a610}$; wherein definitions of $C_{2-10}$ heteroaryl, $R^{66}, R^{a69}$ and $R^{a610}$ are the same as described above.

In a preferred embodiment of the present invention,

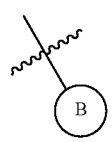

is preferably

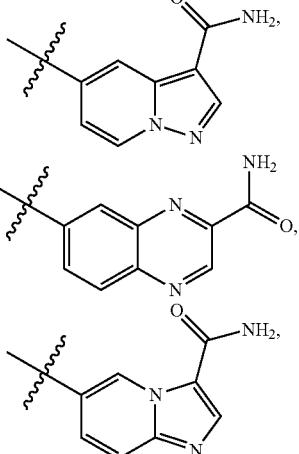

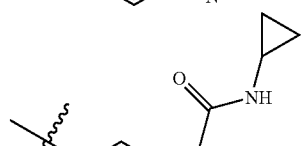

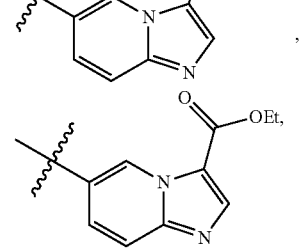

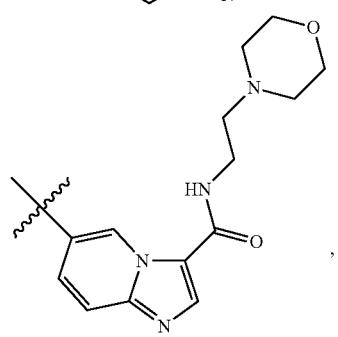

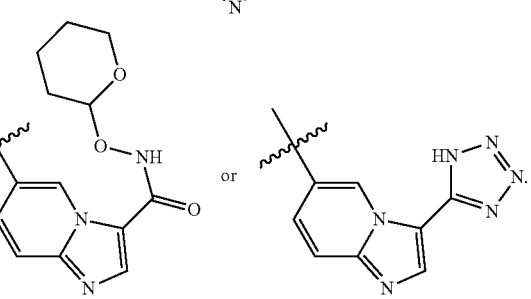

In a preferred embodiment of the present invention,
one of $R^1$ and $R^2$ is hydrogen, or substituted or unsubstituted $C_{1-6}$ alkyl, and the other is hydrogen, cyano, sulfonyl, substituted or unsubstituted $C_{1-6}$ alkyl, —C(O)OR$^{91}$, —COR$^{92}$,

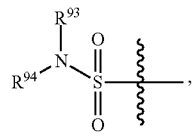

—S(O)R$^{95}$, —S(O)$_2$R$^{96}$, —C(O)NR$^{97}$R$^{98}$, or substituted or unsubstituted $C_{2-10}$ heteroaryl; or $R^1$ and $R^2$ together with the carbon atom to which they are attached form substituted or unsubstituted 4-8 membered carbocycle containing a double bond, or a substituted or unsubstituted 4-8 membered heterocycle; wherein, definitions of $R^{91}$, $R^{92}$, $R^{93}$, $R^{94}$, $R^{95}$, $R^{96}$, $R^{97}$ and $R^{98}$ are the same as described above; definitions of the substitutions in the substituted $C_{1-6}$ alkyl, the substituted $C_{2-10}$ heteroaryl, the substituted 4-8 membered carbocycle and the substituted 4-8 membered heterocycle are the same as described above;

in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —NR$^{a3}$R$^{a4}$, —OR$^{35}$, —SR$^{a6}$, —C(O)OR$^{a7}$, —C(O)NR$^{a8}$R$^{a9}$, —COR$^{a10}$, substituted or unsubstituted $C_{1-6}$ alkyl, substituted or unsubstituted $C_{2-8}$ heterocycloalkyl, substituted or unsubstituted $C_{6-20}$ aryl, or substituted or unsubstituted $C_{2-10}$ heteroaryl; wherein, the definitions of $R^{a3}$, $R^{a4}$, $R^{a5}$, $R^{a6}$, $R^{a7}$, $R^{a8}$, $R^{a9}$ and $R^{a10}$ are the same as described above; definitions of the substitutions in the substituted $C_{1-6}$ alkyl, substituted $C_{2-8}$ heterocycloalkyl, substituted $C_{6-20}$ aryl or substituted $C_{2-10}$ heteroaryl are the same as described above;

$R^4$ is hydrogen, $C_{1-6}$ alkyl or $C_{3-10}$ cycloalkyl;

$R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are hydrogen;

and $R^6$, $R^{6a}$, $R^{6b}$, $R^{6c}$, $R^{6d}$ and $R^{6e}$ are each independently hydrogen, halogen, cyano, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, cyano, —OR$^{61}$, —SR$^{62}$, —C(O)R$^{65}$, —C(O)OR$^{66}$ or —C(O)NR$^{a69}$R$^{a610}$; definitions of $R^{61}$, $R^{62}$, $R^{65}$, $R^{66}$, $R^{a69}$ and $R^{a610}$ are the same as described above; definitions of the substitutions in the substituted $C_{1-6}$ alkyl, substituted $C_{2-8}$ heterocycloalkyl, substituted $C_{6-20}$ aryl or substituted $C_{2-10}$ heteroaryl are the same as described above.

In a preferred embodiment of the present invention,
one of $R^1$ and $R^2$ is hydrogen, and the other is hydrogen, cyano, substituted or unsubstituted $C_{1-6}$ alkyl, —C(O)OR$^{91}$ or —C(O)NR$^{97}$R$^{98}$; or $R^1$ and $R^2$ together with the carbon atom to which they are attached form substituted or unsubstituted 4-8 membered carbocycle containing a double bond; wherein $R^{91}$ is hydrogen or $C_{1-6}$ alkyl; $R^{97}$ and $R^{98}$ are independently hydrogen, or substituted or unsubstituted $C_{1-6}$ alkyl; or $R^{97}$ and $R^{98}$ together with the nitrogen atom to which they are attached form substituted or unsubstituted 3-8 membered heterocyclyl; wherein in $R^1$ or $R^2$, definitions of the substitutions in the substituted $C_{1-6}$ alkyl, the substituted 4-8 membered carbocycle and the substituted 4-8 membered heterocycle are the same as described above; in $R^{97}$ or $R^{98}$, definitions of the substituents in the substituted $C_{1-6}$ alkyl or the substituted 3-8 membered heterocyclyl are the same as described in above;

in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, —OR$^{a5}$, or substituted or unsubstituted $C_{1-6}$ alkyl; $R^{a5}$ is $C_{1-6}$ alkyl; the substituents in the substituted $C_{1-6}$ alkyl are one or more of the following groups: deuterium or halogen;

$R^4$ is hydrogen, $C_{1-6}$ alkyl or $C_{3-10}$ cycloalkyl;

$R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are hydrogen;

and $R^6$, $R^{6a}$, $R^{6b}$, $R^{6c}$, $R^{6d}$ and $R^{6e}$ are each independently cyano, —C(O)OR$^{66}$ or —C(O)NR$^{a69}$R$^{a610}$; wherein $R^{66}$ is $C_{1-6}$ alkyl; $R^{a69}$ and $R^{a610}$ are each independently hydrogen, substituted or unsubstituted $C_{1-6}$ alkyl, substituted or unsubstituted $C_{3-10}$ cycloalkyl or —OR$^{627}$; definitions of the substitutions in the substituted $C_{1-6}$ alkyl or the substituted $C_{3-10}$ cycloalkyl are the same as described above; a definition of $R^{627}$ is the same as described above.

In a preferred embodiment of the present invention,
one of $R^1$ and $R^2$ is hydrogen, and the other is hydrogen, $C_{1-6}$ alkyl, —C(O)OR$^{91}$ or —C(O)NR$^{97}$R$^{98}$; or $R^1$ and $R^2$ together with the carbon atom to which they are attached form 4-8 membered carbocycle containing a double bond; wherein $R^{91}$, $R^{97}$ and $R^{98}$ are independently hydrogen or $C_{1-6}$ alkyl; or $R^{97}$ and $R^{98}$ together with the nitrogen atom to which they are attached form 3-8 membered heterocyclyl;

$R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, trifluoromethyl, difluoromethyl, methyl, deuterated methyl or methoxy; 1 or 2 positions in ring A are not hydrogen;

$R^4$ is hydrogen, $C_{1-6}$ alkyl or $C_{3-10}$ cycloalkyl;

$R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are hydrogen;

and $R^6$, $R^{6a}$, $R^{6b}$, $R^{6c}$, $R^{6d}$ and $R^{6e}$ are each independently cyano, —C(O)OR$^{66}$ or —C(O)NR$^{a69}$R$^{a610}$; wherein $R^{66}$ is $C_{1-6}$ alkyl; $R^{a69}$ and $R^{a610}$ are each independently hydrogen, substituted or unsubstituted $C_{1-6}$ alkyl, $C_{3-10}$ cycloalkyl or —OR$^{627}$; the substituents in the substituted $C_{1-6}$ alkyl are $C_{2-8}$ heterocycloalkyl

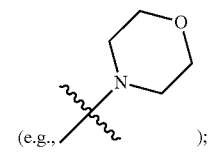 [SMILES: *N1CCOCC1]

(e.g., );

$R^{627}$ is $C_{2-8}$ heterocycloalkyl

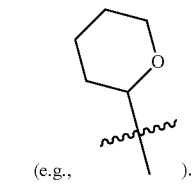

(e.g., ).

In a preferred embodiment of the present invention,
$R^1$ is hydrogen, and $R^2$ is hydrogen, $C_{1-6}$ alkyl, —C(O)OR$^{91}$ or —C(O)NR$^{97}$R$^{98}$; $R^{91}$, $R^{97}$ and $R^{98}$ are independently hydrogen or $C_{1-6}$ alkyl;

and ring A is

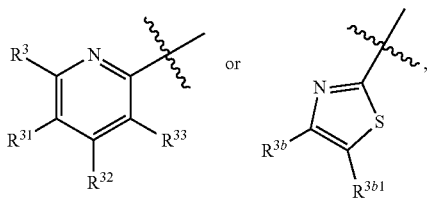

wherein R³ and R³³ are independently hydrogen, halogen, —OR$^{a5}$, or substituted or unsubstituted C$_{1-6}$ alkyl, but not hydrogen at the same time; R$^{3b}$ is hydrogen, halogen, —OR$^{a5}$, or substituted or unsubstituted C$_{1-6}$ alkyl; a definition of R$^{a5}$ is the same as described above; definitions of the substitutions in the substituted C$_{1-6}$ alkyl are the same as described above; R$^{31}$, R$^{32}$ and R$^{3b1}$ are hydrogen;
and

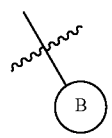

is

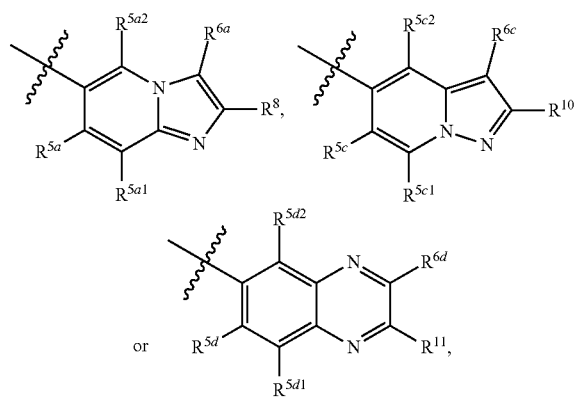

further preferably

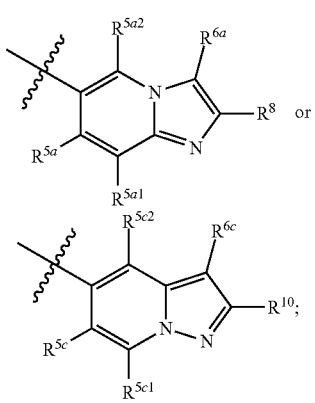

wherein R$^{5a}$, R$^{5a1}$, R$^{5a2}$, R$^{5c}$, R$^{5c1}$, R$^{5c2}$, R$^{5d}$, R$^{5d1}$, R$^{5d2}$, R$^{8}$, R$^{10}$ and R$^{11}$ are hydrogen; R$^{6a}$, R$^{6c}$ and R$^{6d}$ are each independently cyano, C$_{2-10}$ heteroaryl, —C(O)OR$^{66}$ or —C(O)NR$^{a69}$R$^{a610}$; wherein definitions of C$_{2-10}$ heteroaryl, R$^{66}$, R$^{a69}$ and R$^{a610}$ are the same as described above.

In a preferred embodiment of the present invention,
R¹ and R² are both hydrogen;
or R¹ is hydrogen and R² is

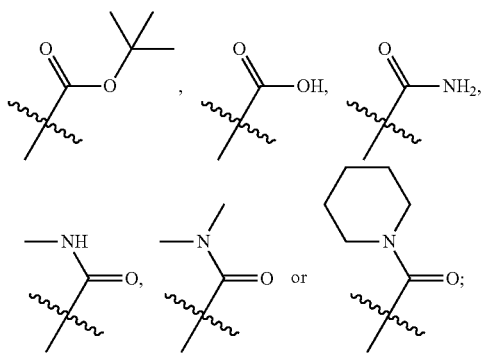

or R¹ and R² together with the carbon atom to which they are attached form cyclohexene;

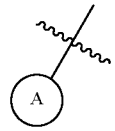

is

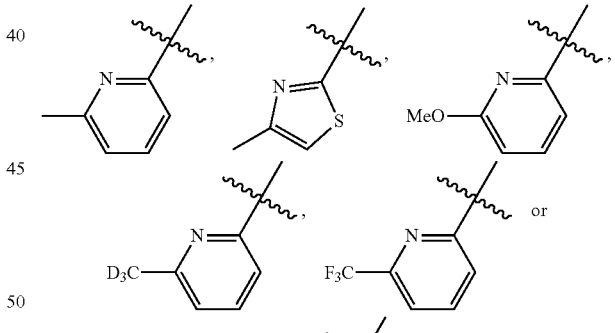

and

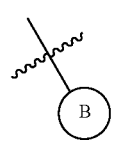

is

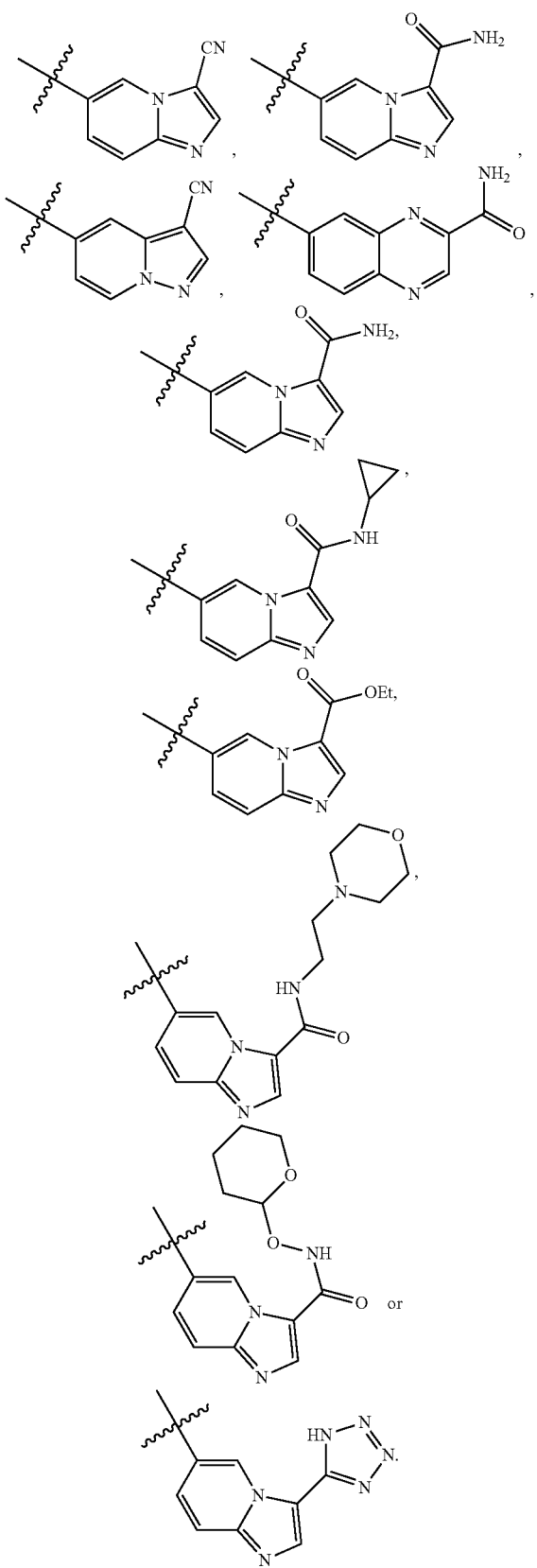

In a preferred embodiment of the present invention, when $R^1$ or $R^2$ is —C(O)NR$^{917}$R$^{918}$, and $R^6$, $R^{6a}$, $R^{6b}$, $R^{6c}$, $R^{6d}$ or $R^{6e}$ is —C(O)NR$^{a69}$R$^{a610}$, then —C(O)NR$^{917}$R$^{918}$ and —C(O)NR$^{a69}$R$^{a610}$ are not —C(O)NH$_2$ at the same time; or —C(O)NR$^{a69}$R$^{a610}$ is —C(O)NH$_2$, and —C(O)NR$^{917}$R$^{918}$ is not —C(O)NHCH$_3$.

In a preferred embodiment of the present invention, when $R^1$ or $R^2$ is —C(O)OR$^{98}$, and $R^6$, $R^{6a}$, $R^{6b}$, $R^{6c}$, $R^{6d}$ or $R^{6e}$ is —C(O)NR$^{a69}$R$^{a610}$, then —C(O)NR$^{a69}$R$^{a610}$ is —C(O)NH$_2$, and —C(O)OR$^{98}$ is not —COOH.

In a preferred embodiment of the present invention, when $R^1$ or $R^2$ is —C(O)NR$^{97}$R$^{98}$, and $R^6$, $R^{6a}$, $R^{6b}$, $R^{6c}$, $R^{6d}$ or $R^{6e}$ is —CN, then —C(O)NR$^{97}$R$^{98}$ is not

In the present invention, the aromatic heterocyclic substituted olefin compound represented by general formula I is preferably any one of the following compounds:

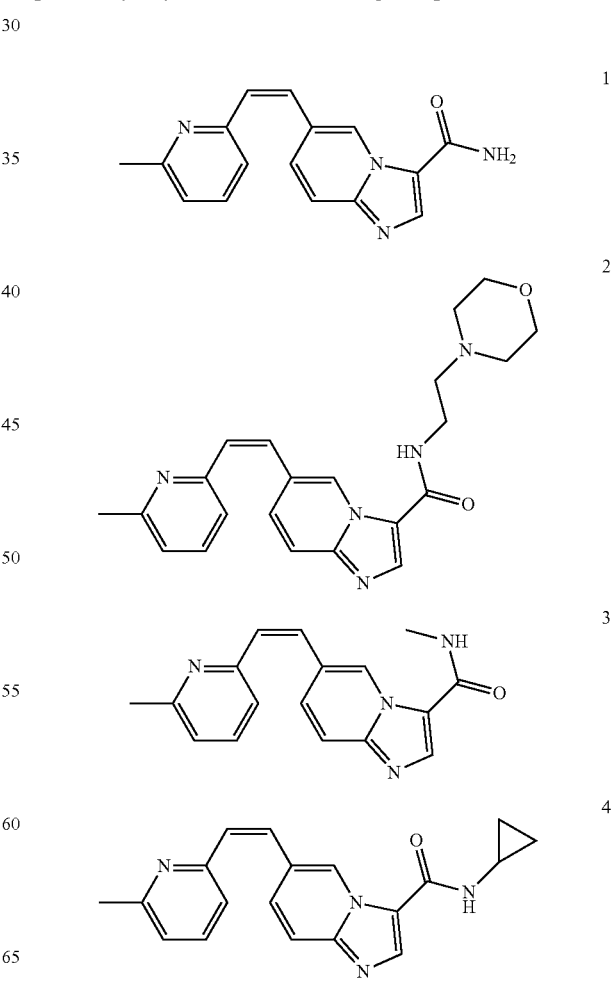

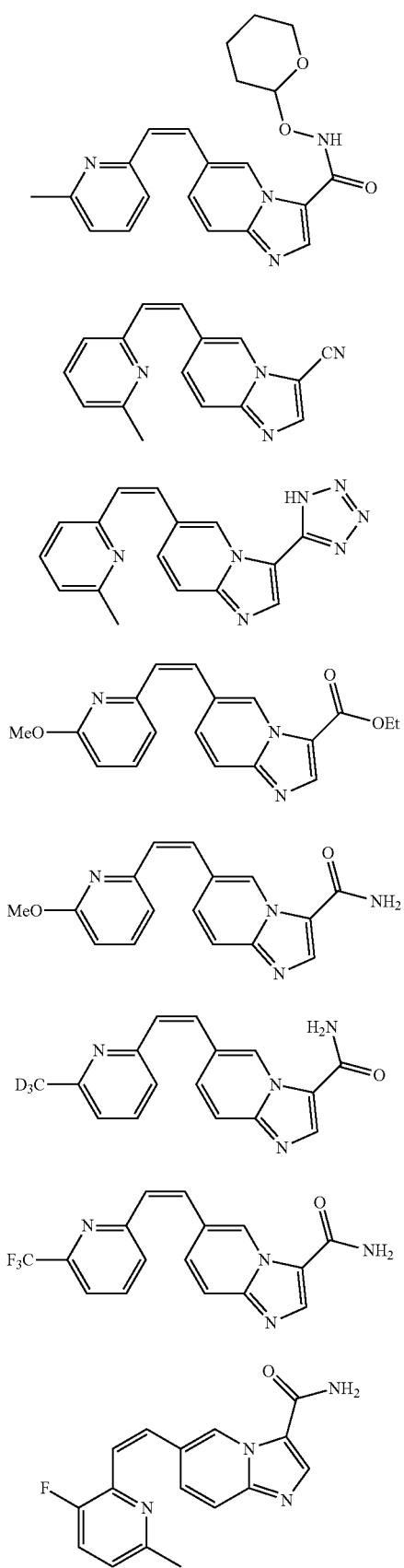
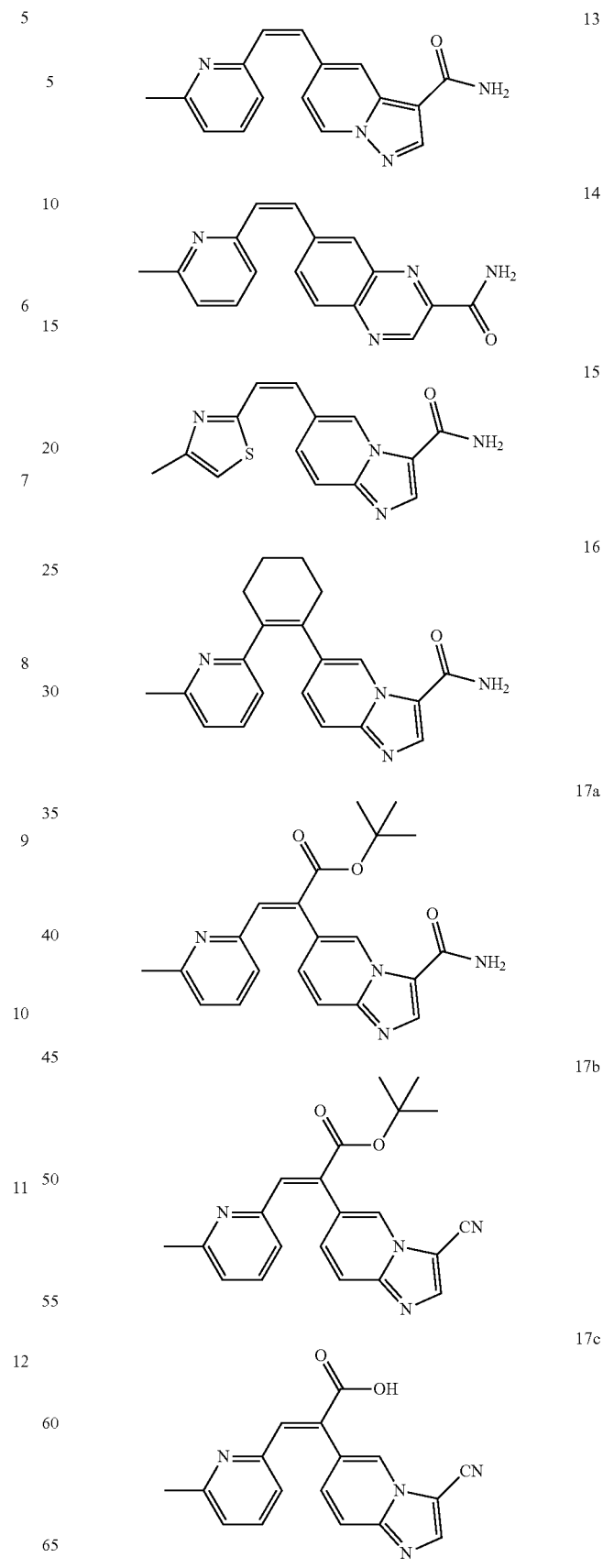

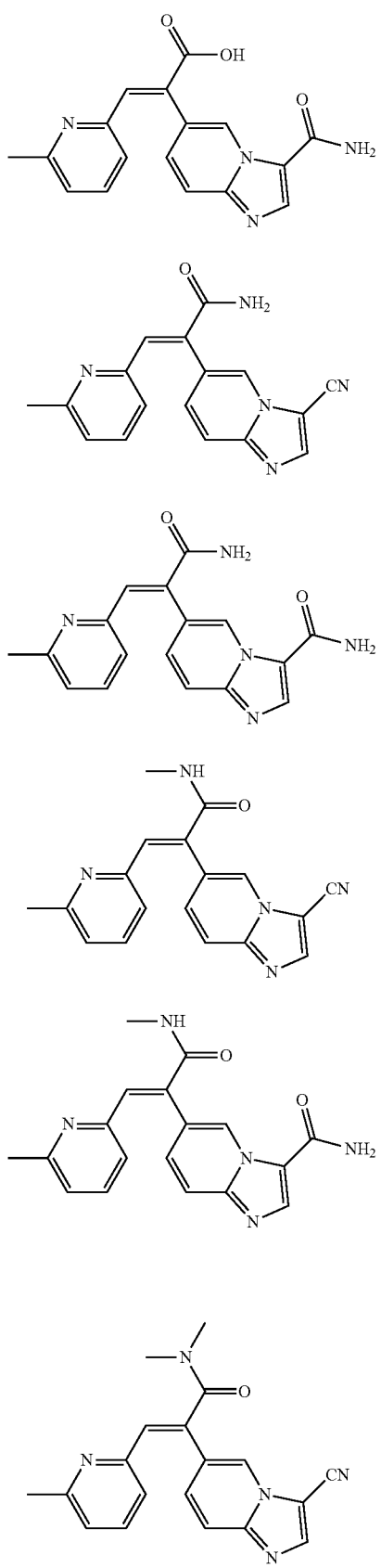
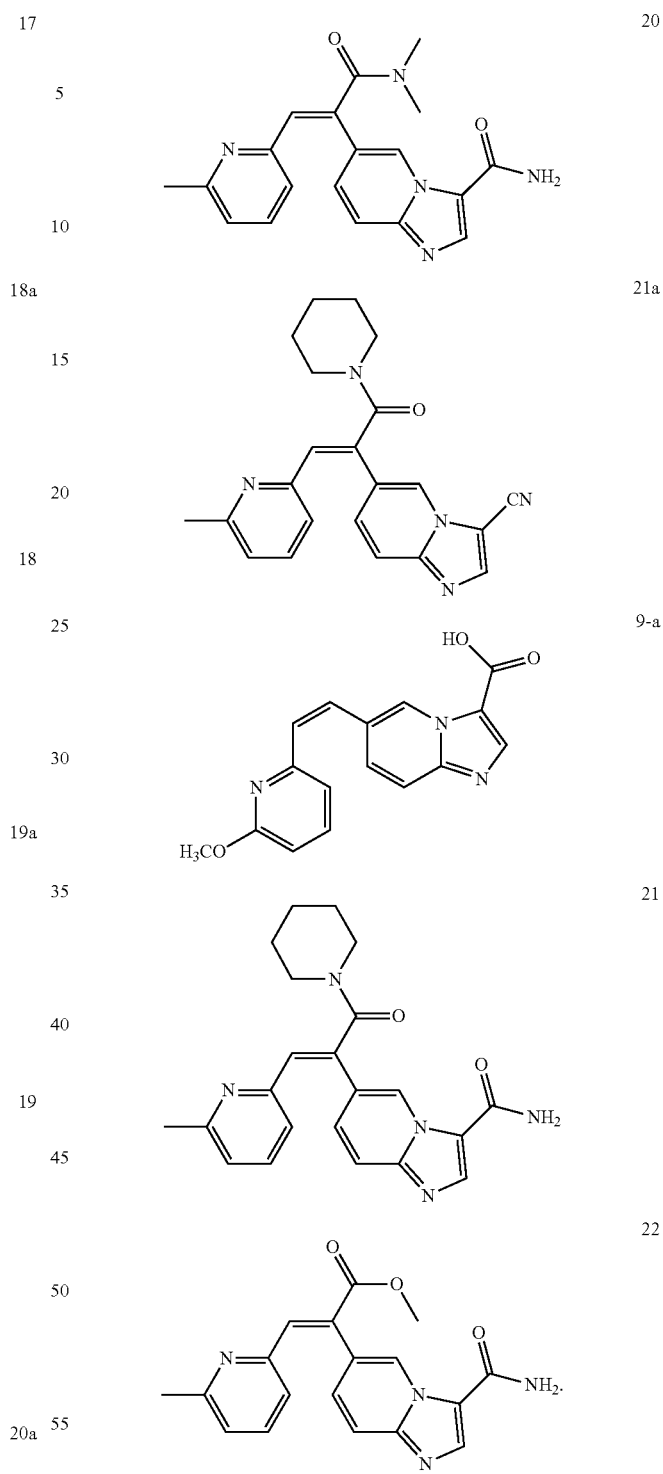
The present invention also provides a method for preparing the aromatic heterocyclic substituted olefin compound represented by general formula I, comprising method I or method II:
method I comprises the following steps: conducting a coupling reaction of compound II-A with compound II-2 as shown below;

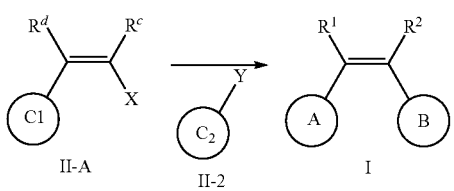

one of X and Y is halogen, such as Cl, Br or I; the other is an organotin reagent such as a tri-n-butyltin reagent, or an organoboron reagent such as boric acid or pinacol borate; one of ring C1 and ring C2 is ring A, and the other is ring B; one of $R^d$ and $R^c$ is $R^1$, and the other is $R^2$; when ring C1 is ring A, then $R^d$ is $R^1$; definitions of $R^1$, $R^2$, ring A and ring B are the same as described above;

method II comprises the following steps:

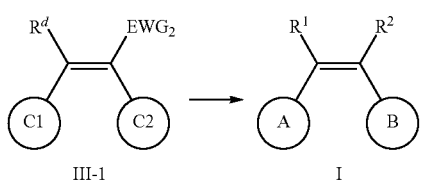

one of ring C1 and ring C2 is ring A, and the other is ring B; one of $R^d$ and $R^c$ is $R^1$, and the other is $R^2$; when ring C1 is ring A, then $R^d$ is $R^1$; definitions of $R^1$, $R^2$, ring A and ring B are the same as described above; $EWG_2$ is an electron withdrawing group, such as cyano, ester, carboxy, alkylcarbonyl, sulfonyl, aminosulfonyl, alkylaminoformyl, —S(O)$R^{613}$, —S(O)$_2$R$^{614}$ or

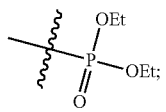 [SMILES: *P(=O)(OCC)OCC]

definitions of $R^{613}$ and $R^{614}$ are the same as described above.

when $R^1$ and $R^2$ are hydrogen, the aromatic heterocyclic substituted olefin compound represented by general formula I can be prepared by the following method, which comprises the following steps: hydrogenolyzing compound I-1 under the action of a palladium reagent;

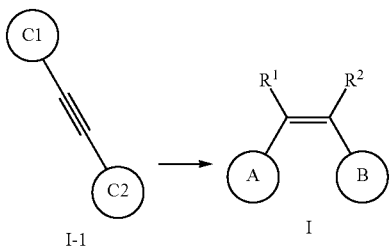

one of ring C1 and ring C2 is ring A, and the other is ring B; wherein, definitions of ring A and ring B are the same as described above.

Wherein some compounds can be synthesized by the method of route 1. Route 1 comprises the following steps: conducting a coupling reaction of compound I-5 with trimethylsilyl (TMS) acetylene to obtain compound I-4, removing a TMS protecting group from compound I-4 to obtain compound I-3, conducting a coupling reaction of compound I-3 with compound I-2 to obtain compound I-1, and hydrogenolyzing compound I-1 under the action of a passivated palladium reagent to obtain the aromatic heterocyclic substituted olefin compound represented by general formula I.

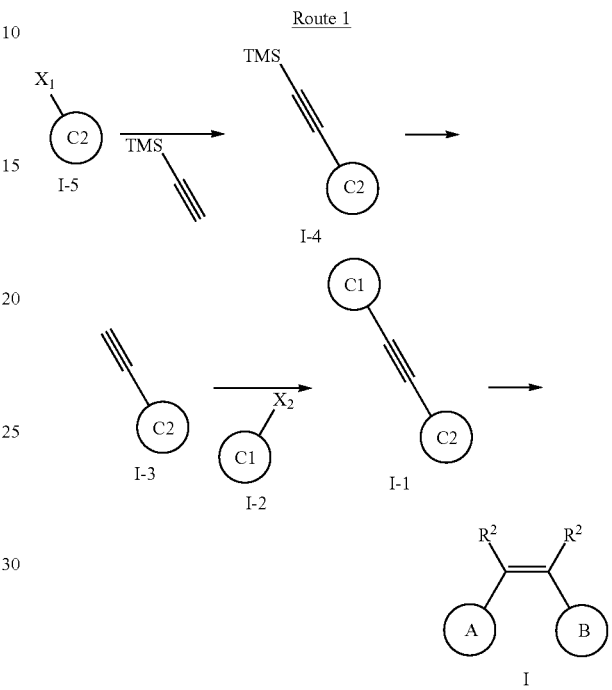

wherein $R^1$ and $R^2$ are hydrogen, and $X_1$ and $X_2$ are independently Cl, Br or I. one of ring C1 and ring C2 is ring A, and the other is ring B; definitions ring A and ring B are the same as described above;

For example,

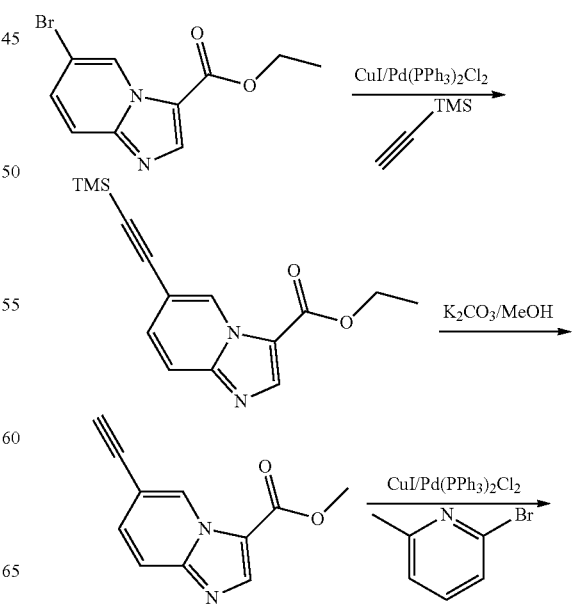

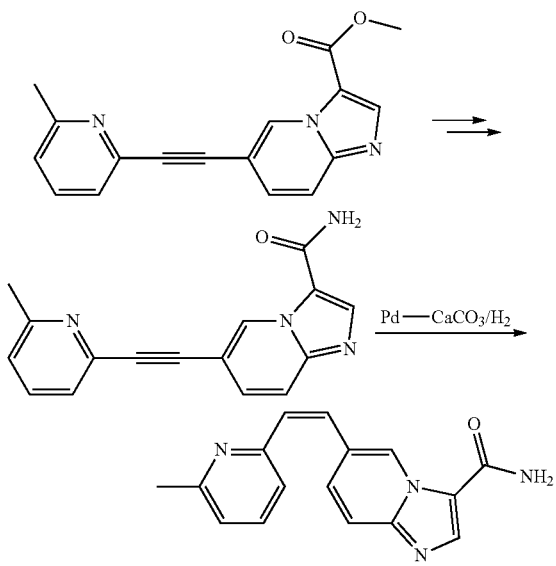

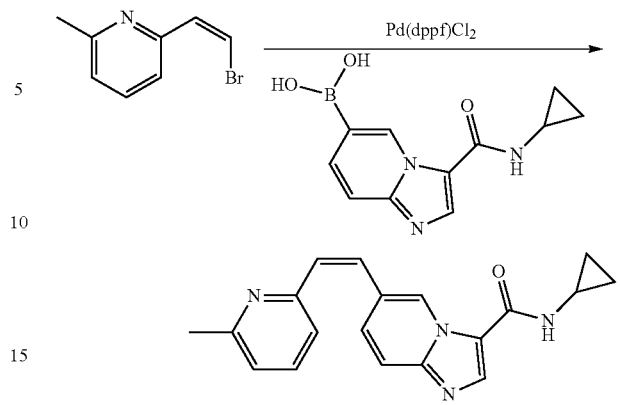

and the other compounds can be synthesized by the method of route 2. Route 2 comprises the following steps: conducting a wittig reaction of compound II-3 with bromomethyltriphenylphosphonium bromide under the action of a base to obtain compound II-1, and conducting a coupling reaction of compound II-1 with compound II-2 under catalysis of a palladium reagent to obtain the aromatic heterocyclic substituted olefin compound represented by general formula I.

Route 2:

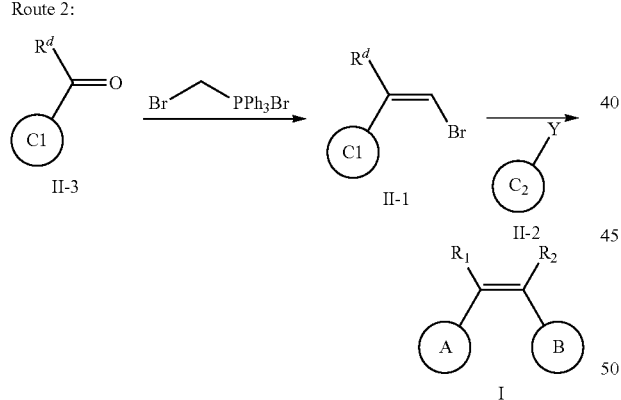

wherein $R^2$ is hydrogen, and Y is an organotin reagent such as a tri-n-butyltin reagent, or an organoboron reagent such as boric acid or pinacol borate; one of ring C1 and ring C2 is ring A, and the other is ring B; $R^d$ is $R^1$ or $R^2$; when ring C1 is ring A, then $R^d$ is $R^1$; definitions of $R^1$, ring A and ring B are the same as described above.

For example,

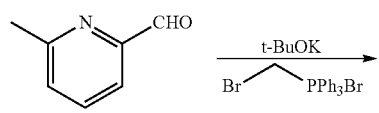

and the other compounds are synthesized by the method of route 3. Route 3 comprises the following steps: conducting a condensation reaction of compound III-4 with compound III-5 under the action of a base to obtain compound III-2, conducting a coupling reaction of compound III-2 with compound III-3 under catalysis of a palladium reagent to obtain compound III-1, and further converting compound III-1 to obtain the aromatic heterocyclic substituted olefin compound represented by general formula I.

Route 3

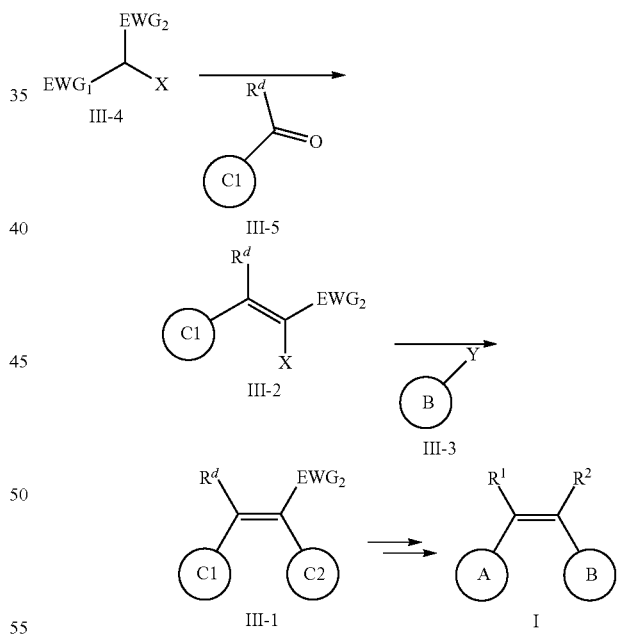

wherein one of X and Y is halogen, such as Cl, Br or I; the other is an organotin reagent such as a tri-n-butyltin reagent, or an organoboron reagent such as boric acid or pinacol borate; one of ring C1 and ring C2 is ring A, and the other is ring B; one of $R^d$ and $R^c$ is $R^1$, and the other is $R^2$; when ring C1 is ring A, then $R^d$ is $R^1$; definitions of $R^1$, $R^2$, ring A and ring B are the same as described above. EWG1 and EWG2 are independently electron withdrawing groups, such as cyano, ester, carboxy, alkylcarbonyl, sulfonyl, aminosulfonyl, alkylaminoformyl, —S(O)$R^{613}$, —S(O)$_2R^{614}$ or

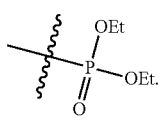 [SMILES: *P(=O)(OCC)OCC]

Y is an organotin reagent such as a tri-n-butyltin reagent, or an organoboron reagent such as boric acid or pinacol borate, definitions of $R^{613}$ and $R^{614}$ are the same as described above.

For example,

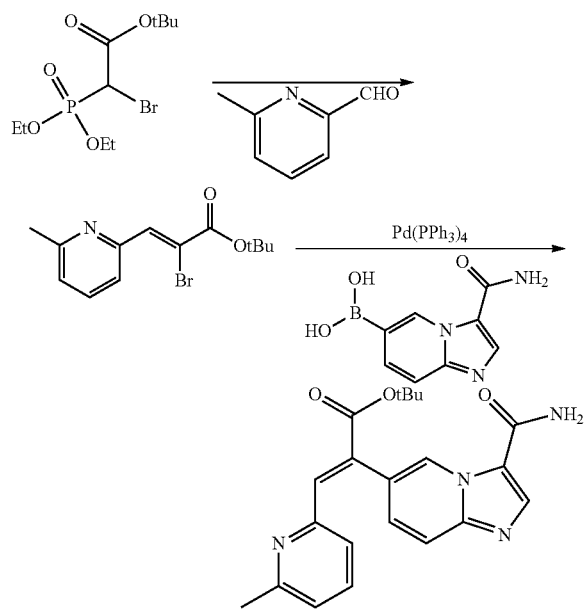

there are also some compounds synthesized by the method of route 4. Route 4 comprises the following steps: conducting a coupling reaction of compound IV-4 with compound IV-3 to synthesize compound IV-1, and further conducting a coupling reaction of compound IV-1 with compound IV-2 to obtain the aromatic heterocyclic substituted olefin compound represented by general formula I.

Route 4

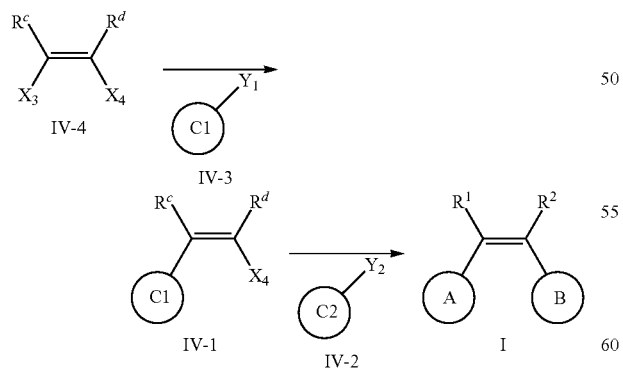

wherein $X_3$ and $X_4$ are independently Cl, Br or I. $Y^1$ and $Y^2$ are independently an organotin reagent such as a tri-n-butyltin reagent, or an organoboron reagent such as boric acid or pinacol borate, one of ring C1 and ring C2 is ring A, and the other is ring B; one of $R^d$ and $R^c$ is $R^1$, and the other is $R^2$; when ring C1 is ring A, then $R^d$ is $R^1$; definitions of $R^1$, $R^2$, ring A and ring B are the same as described above.

For example,

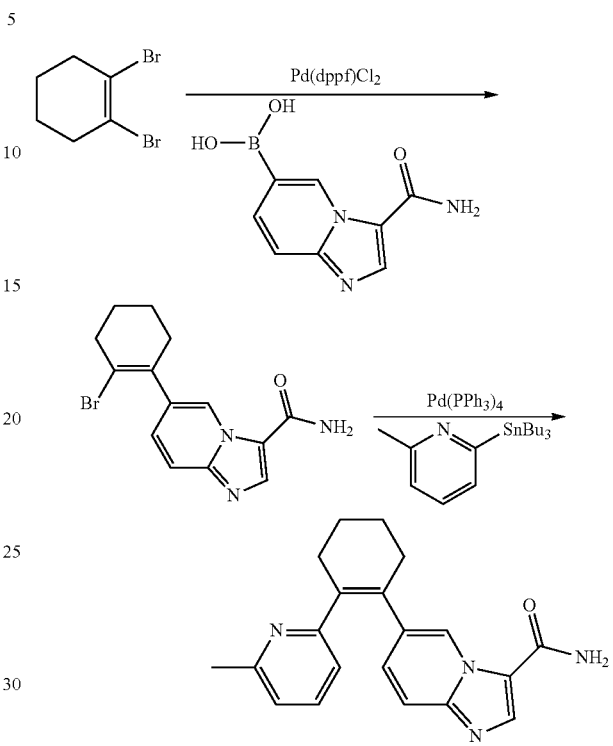

the conditions and steps adopted for the chemical reactions involved in the various reaction routes described in the present invention can be carried out with reference to the conventional conditions and steps of such reactions in the art, and specific reference may be made to the literatures: R. Larock, *Comprehensive Organic Transformations*, VCH Publishers (1989); T. W. Greene and P. G. M. Wuts, *Protective Groups in Organic Synthesis*, $3^{rd}$ ED., John Wiley and Sons (1999); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and subsequent versions. The present application cites the entire contents of the above literatures. In addition, other target compounds of the present invention the compound obtained by the above method can also be obtained from the compound obtained by the above method through modifying the peripheral position by referring to the related method of the above literatures.

The present invention also provides any one of the following intermediate compounds:

1-a

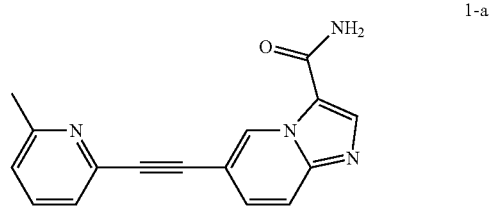

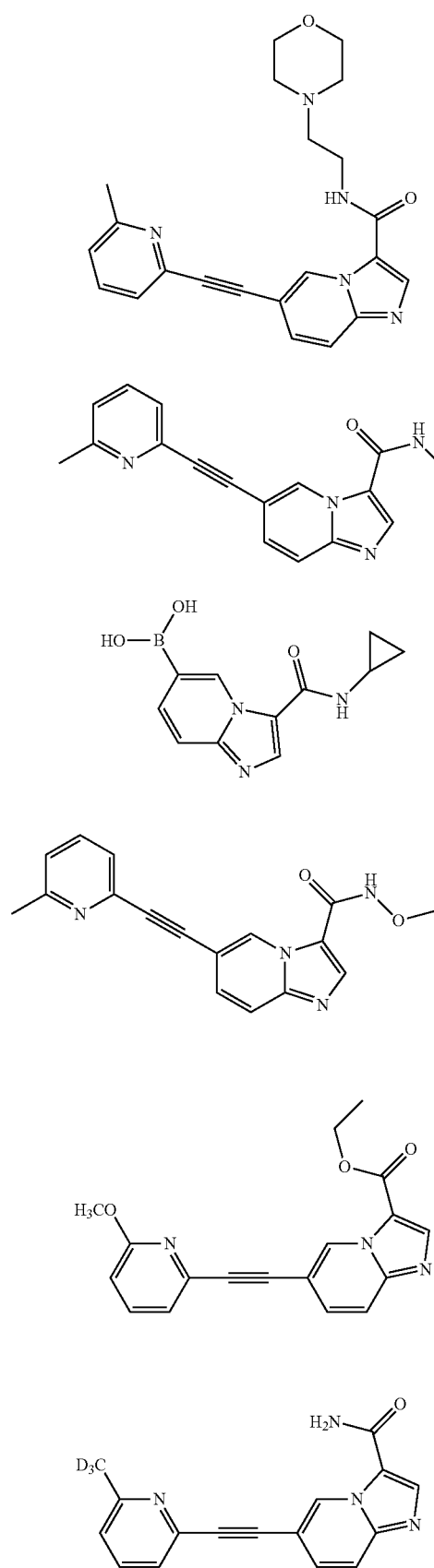
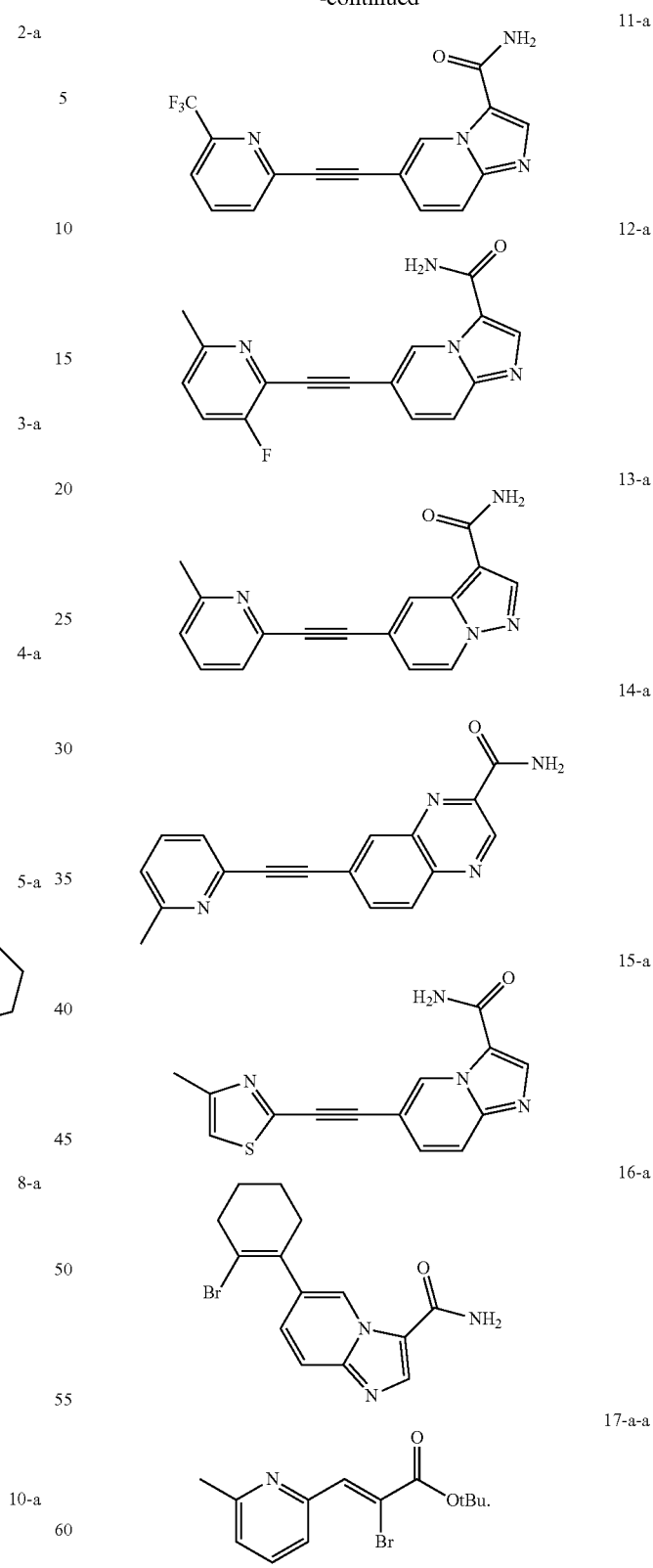
At least one aromatic heterocyclic substituted olefin compound prepared according to the above method or a pharmaceutically acceptable salt thereof can be purified by column chromatography, high performance liquid chromatography, crystallization, or other appropriate conditions. The conditions and steps of the purification methods such as column chromatography, high performance liquid chromatography and crystallization can be selected according to conventional conditions and steps in the art.

The compounds described herein include, but are not limited to, their optical isomers, racemates, and other mixtures. In these cases, single enantiomers or diastereomers, such as optically active structures, can be obtained by asymmetric synthesis or resolution from racemic mixtures or diastereomer mixtures. For the resolution of racemic mixtures or diastereomeric mixtures, it can be separated by traditional methods, such as crystallization using a resolution reagent; it can also be separated by chromatography.

For example, chiral high performance liquid chromatography (HPLC) columns. The compound described herein exist in various tautomers, and the term "compound" includes all tautomeric forms of the compound. The compound here also includes its different crystal forms, including polycrystals and clathrates. Similarly, the term "salt" also includes all its optical isomers, racemates, and other mixtures, tautomers, and crystal forms.

The present invention also provides use of the aromatic heterocyclic substituted olefin compound represented by general formula I or the pharmaceutically acceptable salt thereof in the manufacture of an ALK5 inhibitor or in the manufacture of a medicament for treating and/or preventing ALK5-mediated diseases.

The "ALK5-mediated diseases" include, but are not limited to: one or more of cancer, organ fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, arteriosclerosis, and tumor metastasis and growth, preferably cancer and/or organ fibrosis. The cancer includes, but is not limited to, colon cancer, pancreatic cancer, breast cancer, prostate cancer, lung cancer, brain cancer, ovarian cancer, cervical cancer, testicular cancer, kidney cancer, head or neck cancer, bone cancer, skin cancer, rectal cancer, liver cancer, colon cancer, esophageal cancer, gastric cancer, pancreatic cancer, thyroid cancer, bladder cancer, lymphoma, leukemia and melanoma. The organ fibrosis includes, but is not limited to, renal fibrosis, liver fibrosis and lung fibrosis.

The present invention also provides a pharmaceutical composition, comprising a prophylactically and/or therapeutically effective dose of one or more of the aromatic heterocyclic substituted olefin compound represented by general formula I and the pharmaceutically acceptable salt thereof, and a pharmaceutically acceptable carrier.

In the present invention, the "prophylactically and/or therapeutically effective dose" means (i) an amount of the compound of the present invention that prevents and/or treats the specific disease or condition described in the application, (ii) an amount of the compound of the present invention that attenuates, improves or eliminates one or more symptoms of the specific disease or condition described in the application, or (iii) an amount of the compound of the present invention that prevents or delays the onset of one or more symptoms of the specific disease or condition described in the application. The dose for treating human patients may be 0.0001 mg/kg to 50 mg/kg, most usually 0.001 mg/kg to 10 mg/kg weight, for example in the range of 0.01 mg/kg to 1 mg/kg. Such a dose can be given, for example, 1 to 5 times a day.

According to the therapeutic purpose, the pharmaceutical composition can be made into various types of unit dosage forms, such as tablets, pills, powders, liquids, suspensions, emulsions, granules, capsules, suppositories and injections (solutions and suspensions), and preferably tablets, pills, granules, capsules, etc.

In order to shape a pharmaceutical composition in a tablet form, any excipient known and widely used in the art may be used. For example, carriers such as lactose, white sugar, sodium chloride, glucose, urea, starch, calcium carbonate, kaolin, crystalline cellulose, and silicic acid; binders, such as water, ethanol, propanol, ordinary syrups, glucose solutions, starch solutions, gelatin solutions, carboxymethyl cellulose, shellac, methyl cellulose and potassium phosphate, polyvinylpyrrolidone; disintegrants, such as dry starch, sodium alginate, agar powders and kelp powders, sodium bicarbonate, calcium carbonate, fatty acid esters of polyethylene sorbitan, sodium lauryl sulfate, monoglyceryl stearate, starch and lactose; disintegration inhibitors, such as white sugar, glycerol tristearate, coconut oil and hydrogenated oil; adsorption accelerators, such as quaternary ammonium bases and sodium lauryl sulfate; wetting agents, such as glycerin and starch; adsorbents, such as starch, lactose, kaolin, bentonite and colloidal silicic acid; and lubricants, such as pure talc, stearate, boric acid powders and polyethylene glycol. Ordinary coating materials can also be used to make sugar coated tablets, gelatin coated tablets, enteric tablets, film coated tablets, bilayer tablets, and multilayer tablets as needed.

In order to shape a pharmaceutical composition in a pill form, any excipient known and widely used in the art can be used, for example, carriers such as lactose, starch, coconut oil, hardened vegetable oil, kaolin and talc; binders, such as gum arabic powders, tragacanth powders, gelatin and ethanol; disintegrants, such as agar and kelp powders.

In order to shape a pharmaceutical composition in a suppository form, any excipient known and widely used in the art can be used, for example, polyethylene glycol, coconut oil, higher alcohols, esters of higher alcohols, gelatin and semi synthetic glyceride.

In order to prepare a pharmaceutical composition in an injection form, a solution or suspension can be sterilized (preferably with an appropriate amount of sodium chloride, glucose or glycerin, etc.) to make an injection that is isotonic with blood. When preparing an injection, any carrier commonly used in the art may also be used, for example, water, ethanol, propylene glycol, ethoxylated isostearyl alcohol, polyoxylated isostearyl alcohol and fatty acid esters of polyethylene sorbitan. In addition, common dissolving agents, buffers and analgesics may also be added.

In the present invention, an administration method of the pharmaceutical composition is not particularly limited. Various formulations may be selected for administration according to the patient's age, gender and other conditions and symptoms. For example, tablets, pills, solutions, suspensions, emulsions, granules or capsules are administered orally; Injections may be administered alone or mixed with an injection fluid (such as a glucose solution and an amino acid solution) for intravenous injection; Suppositories are administered to the rectum.

Unless otherwise stated, the following terms appearing in the specification and claims of the present invention have the following meanings:

a single dash, "-", or double dash, "=" can be added before and/or after the term of the present invention to indicate a bond sequence of the bond between the named substituent and its parent part; a single dash represents a single bond, and a double dash represents a pair of single bonds in the case of a double bond or a spiro substituent.

When there is no single dash or double dash, it may be considered that a single bond is formed between the substituent and its parent part; In addition, substituents are read "from left to right" unless otherwise indicated. For example, $C_{1-6}$ alkoxycarbonyloxy and —OC(O)$C_{1-6}$ alkyl represent the same function; similarly, arylalkyl, arylalkyl-, and -alkylaryl represent the same function.

The term "alkyl" in the present invention refers to a branched and straight chain saturated aliphatic hydrocarbyl containing 1 to 6 carbon atoms, such as methyl, ethyl, n-propyl, isopropyl, n-butyl, tert-butyl, isobutyl, pentyl, hexyl and their various isomers. "$C_{x1-y1}$" alkyl with a defined carbon number range in the present invention (x1 and y1 are integers), such as "$C_{1-6}$ alkyl", has the same definition except that the carbon number range is different from the "alkyl" carbon number definition range in this paragraph.

When "alkyl" serves as a linking group between two other groups, it may also be straight or branched chain, and examples include, but are not limited to, $CH_2$—, —$CH_2CH_2$—, —$CH_2CH_2CHC(CH_3)$—, —$CH_2CH_2(CH_2CH_3)CH_2$—.

The term "cycloalkyl" in the present invention refers to monocyclic or bicyclic cycloalkyl. Monocyclic cycloalkyl is a cyclic hydrocarbyl containing 3 to 10 carbon atoms. These groups may be saturated or unsaturated, but are not aromatic. In certain embodiments, cycloalkyl is fully saturated. Bicyclic cycloalkyl is abridged monocyclic cycloalkyl or fused bicyclic cycloalkyl. The bridged monocyclic cycloalkyl contains a monocyclic cycloalkyl ring in which two non-adjacent carbon atoms of the monocyclic cycloalkyl ring are connected by an alkylene bridge between one to three additional carbon atoms (i.e., a bridged group in the form of —$(CH_2)_w$—, where w is 1, 2 or 3). The fused bicyclic cycloalkyl includes a monocyclic cycloalkyl ring fused to phenyl, monocyclic cycloalkyl, monocyclic cycloalkenyl, monocyclic heterocyclyl, or monocyclic heteroaryl. The bridged or fused bicyclic cycloalkyl is connected to the parent molecular moiety through any carbon atom contained in the monocyclic cycloalkyl ring. Cycloalkyl may be optionally substituted with one or two groups as independent oxo or thio.

The term "cycloalkenyl" in the present invention refers to monocyclic or bicyclic cycloalkenyl. Monocyclic cycloalkenyl is a cyclic hydrocarbyl containing 3 to 8 carbon atoms, which are unsaturated (i.e., containing at least one cyclic carbon-carbon double bond), but are not aromatic. The bicyclic cycloalkenyl ring is a bridged monocyclic ring or a fused bicyclic ring. The bridged monocyclic ring contains a monocyclic cycloalkenyl ring, in which two non-adjacent carbon atoms of the monocyclic ring are connected by an alkylene bridge between one to three additional carbon atoms (i.e., a bridged group in the form of —$(CH_2)_w$—, where w is 1, 2 or 3). The fused bicyclic cycloalkenyl ring system includes a monocyclic cycloalkenyl ring fused to phenyl, monocyclic cycloalkyl, monocyclic cycloalkenyl, monocyclic heterocyclyl, or monocyclic heteroaryl. The bridged or fused bicyclic cycloalkenyl is connected to the parent molecular moiety through any carbon atom contained in the monocyclic cycloalkenyl ring. Cycloalkenyl may be optionally substituted with one or two groups as independent oxo or thio.

The term "alkoxy" in the present invention refers to cyclic or acyclic alkyl having the number of carbon atoms connected by an oxygen bridge. Thus, "alkoxy" includes the above definitions of alkyl and cycloalkyl.

The term "alkylthio" in the present invention refers to cyclic or acyclic alkyl having the number of carbon atoms connected by a sulfur bridge. Thus, "alkylthio" includes the above definitions of alkyl and cycloalkyl.

The term "alkenyl" in the present invention refers to straight chain, branched chain, or cyclic non-aromatic hydrocarbyl containing the specified number of carbon atoms and at least one carbon-carbon double bond. There is preferably one carbon-carbon double bond, and up to four non-aromatic carbon-carbon double bonds may be present. Thus, "$C_{2-8}$ alkenyl" refers to alkenyl having 2 to 8 carbon atoms. The straight chain, branched chain, or cyclic portion of alkenyl may contain a double bond, and if it is indicated as a substituted alkenyl, it may be substituted.

The term "alkynyl" in the present invention refers to straight chain, branched chain, or cyclic hydrocarbyl containing the specified number of carbon atoms and at least one carbon-carbon triple bond. There can be up to three carbon-carbon triple bonds. Thus, "$C_{2-8}$ alkynyl" refers to alkynyl having 2 to 8 carbon atoms. "$C_{2-6}$ alkynyl" refers to alkynyl having 2 to 6 carbon atoms.

The term "aryl" in the present invention refers to monocyclic aryl or an aromatic bicyclic system containing at least one benzene ring or a bicyclic system containing only carbon atoms. The bicyclic aryl may be phenyl fused to a monocyclic cycloalkyl, monocyclic cycloalkenyl, or monocyclic heterocyclic. The bicyclic aryl is attached to the parent molecule through any carbon atom contained in the phenyl portion of the bicyclic system or any carbon atom with naphthyl or azulenyl. The fused monocyclic cycloalkyl or monocyclic heterocyclyl portion of the bicyclic aryl may be optionally substituted with one or two oxo and/or thio. In certain embodiments, the bicyclic aryl is (i) naphthyl or (ii) phenyl ring fused to 5- or 6-membered monocyclic cycloalkyl, 5- or 6-membered monocyclic cycloalkenyl, or 5- or 6-membered monocyclic heterocyclyl, where the fused cycloalkyl, cycloalkenyl and heterocyclyl may be optionally substituted with one or two groups as independent oxo or thio.

The term "cyano" in the present invention refers to —CN.

The term "carboxy" in the present invention refers to —COOH.

The term "sulfonyl" in the present invention refers to —SOOOH.

The term "halogen" In the present invention refers to fluorine, chlorine, bromine or iodine.

The term "heteroaryl" in the present invention refers to monocyclic heteroaryl or a bicyclic system containing at least one heteroaryl ring. The monocyclic heteroaryl may be a 5- or 6-membered ring. The 5 membered ring is composed of two double bonds and one, two, three or four nitrogen atoms and an oxygen atom or sulfur atom. The 6 membered ring is composed of three double bonds and one, two, three, or four nitrogen atoms. The 5- or 6-membered heteroaryl is connected to the parent molecule through any carbon atom or nitrogen atom contained in the heteroaryl. The bicyclic heteroaryl is composed of monocyclic heteroaryl fused to phenyl, monocyclic cycloalkyl, monocyclic cycloalkenyl, monocyclic heterocyclyl, or monocyclic heteroaryl. The cycloalkyl or heterocyclyl portion of the fused bicyclic heteroaryl may be optionally substituted with one or two groups that are independent oxo or thio. When the bicyclic heteroaryl contains fused cycloalkyl, cycloalkenyl or heterocyclyl ring, the bicyclic heteroaryl is connected to the parent molecule through any carbon or nitrogen atom contained in the monocyclic heteroaryl portion of the bicyclic system. When the bicyclic heteroaryl is monocyclic heteroaryl fused to a benzene ring or monocyclic heteroaryl, the bicyclic heteroaryl is connected to the parent molecule through any carbon atom or nitrogen atom in the bicyclic system. In certain embodiments, the fused bicyclic heteroaryl is 5- or 6-membered monocyclic heteroaryl fused to a phenyl ring, 5- or 6-membered monocyclic cycloalkyl, 5- or 6-membered monocyclic cycloalkenyl, 5- or 6-membered monocyclic heterocyclyl, or 5- or 6-membered monocyclic heteroaryl, where the fused cycloalkyl, cycloalkenyl and heterocyclyl may be optionally substituted with one or two groups as independent oxo or thio.

The term "heterocyclyl" or "heterocycle" in the present invention refers to a monocyclic heterocycle or a bicyclic heterocycle. The monocyclic heterocycle is a 3-, 4-, 5-, 6- or 7-membered ring containing at least one heteroatom selected from O, N and S, where the ring is saturated or unsaturated, but not aromatic. The monocyclic heterocycle is connected to the parent molecule through any carbon atom or nitrogen atom contained in the monocyclic heterocycle. The bicyclic heterocycle is the monocyclic heterocycle fused to phenyl, monocyclic cycloalkyl, monocyclic cycloalkenyl, monocyclic heterocyclyl or monocyclic heteroaryl. The bicyclic heterocycle is connected to the parent molecule through any carbon or nitrogen atom contained in the monocyclic heterocyclic portion of the bicyclic system. In certain embodiments, the bicyclic heterocyclyl is 5- or 6-membered monocyclic heterocyclyl ring fused to a phenyl ring, 5- or 6-membered monocyclic cycloalkyl, 5- or 6-membered monocyclic cycloalkenyl, 5- or 6-membered monocyclic heterocyclyl, or 5- or 6-membered monocyclic heteroaryl, wherein the bicyclic heterocyclyl may be optionally substituted with one or two groups as independent oxo or thio.

The term "hydroxyl" in the present invention refers to —OH.

The term "nitro" in the present invention refers to —NO$_2$.

It is understood by those of ordinary skill in the art that any group contains one or more substituents, but does not include synthetically unfeasible and/or inherently unstable substituents with an unrealistically high steric hindrance.

The term "pharmaceutically acceptable salts" in the present invention refer to pharmaceutically acceptable salts and solvates formed with acids or bases. Such pharmaceutically acceptable salts include, but are not limited to, salts formed with inorganic acids, such as hydrochloride, phosphate, diphosphate, hydrobromide, sulfate, sulfinate, nitrate, and similar salts; also include salts formed with organic acids, such as malate, maleate, fumarate, tartrate, succinate, citrate, acetate, lactate, sulfonate, p-toluenesulfonate, 2-hydroxy ethyl sulfonate, benzoate, salicylate, stearate and alkanoate such as acetate, HOOC—(CH$_2$)n-COOH, where n is 0-4 salts, and similar salts. Similarly, pharmaceutically acceptable cations include, but are not limited to, sodium, potassium, calcium, aluminum, lithium, and ammonium. Those skilled in the art can recognize various synthetic methods that may be used to prepare non-toxic pharmaceutically acceptable salts.

In the present invention, the "solvate" such as "hydrate" is formed by the interaction of a solvent and a compound. The term "compound" should include solvates of compounds (including hydrates of compounds). Similarly, "salt" also includes salt solvates (such as salt hydrates). Suitable solvates are pharmaceutically acceptable, such as hydrates, which include monohydrates and hemihydrates.

On the basis of not departing from common knowledge in the art, the above-mentioned various preferred conditions can be combined in any manner, such that various preferred examples of the present invention are obtained.

Reagents and raw materials used in the present invention are all commercially available.

In the present invention, the room temperature refers to the ambient temperature, which is 10° C. to 35° C.

The present invention has the following positive improvement effects: The aromatic heterocyclic substituted olefin compound of the present invention is an ALK5 inhibitor, which can be used for the treatment of diseases, such as cancer, renal fibrosis, liver fibrosis, lung fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, arteriosclerosis, and tumor metastasis and growth.

DETAILED DESCRIPTION OF THE PREFERRED EMBODIMENT

The reagents and raw materials (except intermediates) used in the present invention are all commercially available. In the present invention, the room temperature refers to the ambient temperature, which is 10° C. to 35° C. Overnight refers to 8 to 15 hours. Reflux is the reflux temperature of the solvent under normal pressure.

The following is a list of abbreviations used in the examples:
DMF N,N-dimethylformamide
HATU 2-(7-azobenzotriazole)-tetramethylurea hexafluorophosphate
EDCI 1-(3-dimethylaminopropyl)-3-ethylcarbodiimide hydrochloride
HOBt 1-hydroxybenzotriazole
DIPEA diisopropylethylamine
Pd(PPh$_3$)$_4$ palladium tetraphenylphosphine
Pd(dppf)Cl$_2$ [1,1'-bis(diphenylphosphino)ferrocene]palladium di chloride dichloromethane complex
Pd(PPh$_3$)$_2$Cl$_2$ dichlorobis(triphenylphosphine)palladium
LiHMDS bis-(trimethylsilyl) lithium amide
TBAF tetrabutylammonium fluoride
TMS trimethyl silyl In the following examples, the coupling constant of hydrogen on the carbon-carbon double bond in the nuclear magnetic data are used to determine whether the prepared compound is in a cis-configuration (Z) or a trans-configuration (E). In general, the coupling constant between two hydrogen on the double bond of the E configuration compound is significantly greater than the coupling constant between two hydrogen on the double bond of the corresponding Z type compound. In the present invention, for the obtained E type compound, taking comparative compounds 23 and 24 as an example, the coupling constant of two hydrogens on the carbon-carbon double bond is about 16. For the obtained corresponding Z-type compound, i.e., compounds 1 and 3, the coupling constant of two hydrogens on the carbon-carbon double bond is about 12.5.

Synthetic Route of Compound 1

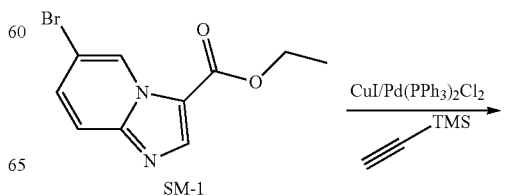

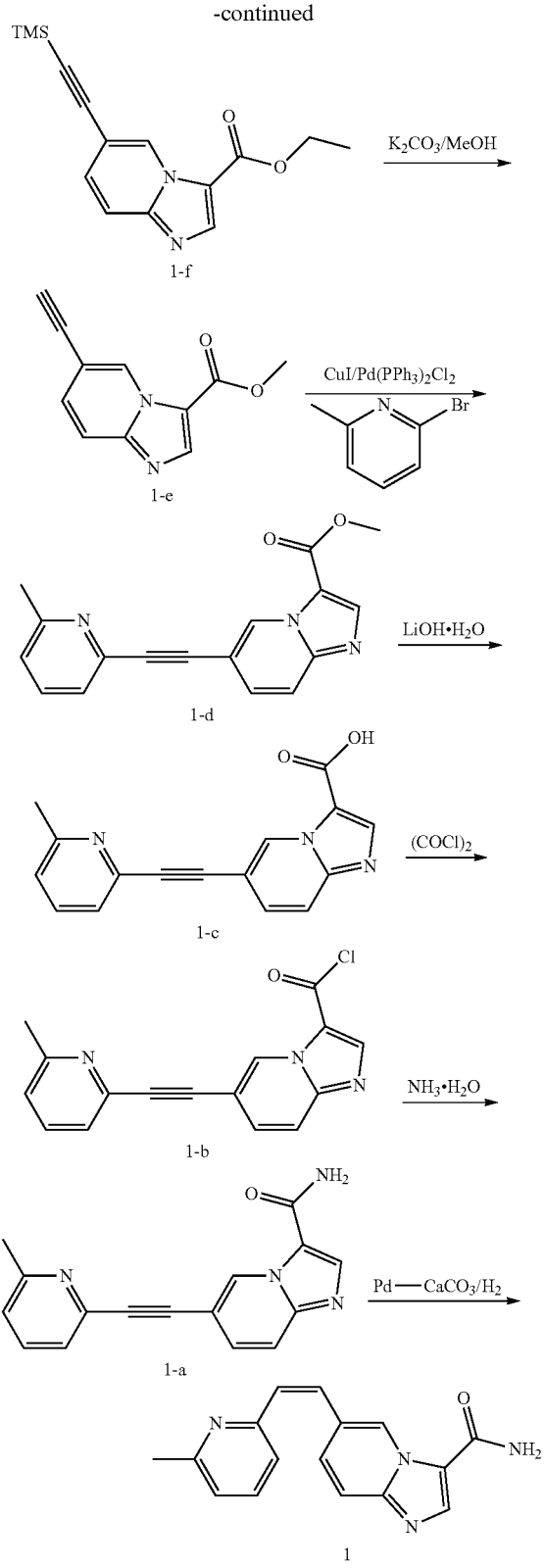

The reaction mixture was replaced with N$_2$ and reacted at 20° C. for 2 hours. After the reaction was completed, the reaction mixture was concentrated to remove organic solvents, added with water (30 mL), and extracted with ethyl acetate (30 mL). The organic phase was washed successively with water and a saturated aqueous sodium chloride solution, and dried over anhydrous sodium sulfate. The mixture was filtered and subjected to rotary evaporation. A crude product was purified by column chromatography (PE:EA=4:1) to obtain compound 1-f (1.34 g, 63%) as a yellow solid. LC-MS (ESI): m/z=287.3 [M+H]$^+$.

Synthesis of Compound 1-e

Potassium carbonate (1.8 g, 13 mmol) was added to a solution of compound 1-f (1.24 g, 4.33 mmol) in methanol (20 mL) and dichloromethane (20 mL), and the mixture was stirred at room temperature for 2 hours. The reaction mixture was concentrated to remove organic solvents, added with water (20 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation to obtain compound 1-e (435 mg, 50%) as a yellow solid. LC-MS (ESI): m/z=201.3 [M+H]$^+$.

Synthesis of Compound 1-d 1-e (435 mg, 2.17 mmol), 2-bromo-6-methylpyridine (374 mg, 2.17 mmol), bis(triphenylphosphine) palladium dichloride (152 mg, 0.217 mmol), and cuprous iodide (41 mg, 0.217 mmol) and triethylamine (15 mL) were added to a reaction flask. The reaction mixture was replaced with N$_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (DCM:MeOH=20:1) to obtain compound 1-d (476 mg, 75%) as a yellow solid. LC-MS (ESI): m/z=292.0 [M+H]$^+$.

Synthesis of Compound 1-c

Compound 1-d (200 mg, 0.69 mmol), tetrahydrofuran (6 mL), methanol (6 mL), water (3 mL), and lithium hydroxide monohydrate (144 mg, 3.43 mmol) were added to a reaction flask. After the mixture was stirred overnight at room temperature, it was added with dilute hydrochloric acid to adjust the pH to 6 to 7, and extracted with ethyl acetate (30 mL×3). The organic phase was washed successively with water and a saturated aqueous sodium chloride solution, and dried over anhydrous sodium sulfate. The mixture was filtered and subjected to rotary evaporation to obtain a crude compound 1-c (101 mg, 53%). LC-MS (ESI): m/z=278.1 [M+H]$^+$.

Synthesis of Compound 1-b

Oxalyl chloride (3 mL) was slowly added to a solution of compound 1-c (101 mg, 0.36 mmol) in dichloromethane (6 mL) under an ice bath, and then another drop of DMF was added. After the mixture was stirred at room temperature overnight, it was concentrated to obtain a crude compound 1-b (138 mg).

Synthesis of Compound 1-a

A solution of compound 1-b (138 mg, 0.36 mmol) in dichloromethane (6 mL) was slowly added to aqueous ammonia (6 mL) under an ice bath, and the mixture was stirred at room temperature for 10 minutes. The mixture was concentrated. A crude product was purified by Prep-TLC Synthesis of Compound 1-f SM-1 (2 g, 7.4 mmol), trimethylsilylacetylene (0.73 g, 7.4 mmol), bis(triphenylphosphine) palladium dichloride (104 mg, 0.148 mmol), and cuprous iodide (28 mg, 0.148 mmol) and triethylamine (15 mL) were added to a reaction flask.

(developing agent DCM:MeOH=10:1) to obtain compound 1-a (45 mg, 45%) as a white solid. LC-MS (ESI): m/z=277.1 [M+H]+; 1H NMR (400 MHz, MeOD): δ 9.85 (s, 1H), 8.35 (s, 1H), 7.80 (t, J=7.8 Hz, 1H), 7.76 (dd, J=9.3, 0.9 Hz, 1H), 7.68 (dd, J=9.3, 1.7 Hz, 1H), 7.53 (d, J=7.7 Hz, 1H), 7.35 (d, J=7.7 Hz, 1H), 2.58 (s, 3H).

Synthesis of Compound 1

Pd—CaCO3 (10 mg) was added to a solution of compound 1-a (38 mg, 0.14 mmol) in ethyl acetate (8 mL) at room temperature. The reaction solution was evacuated and replaced with H2 several times, and the mixture was stirred at room temperature for 2 hours. The mixture was filtered and concentrated. A crude was purified by Prep-HPLC to obtain compound 1 (10 mg, 26%) as a white solid. LC-MS (ESI): m/z=279.1 [M+H]+; 1H NMR (400 MHz, MeOD): δ 9.47-9.57 (m, 1H), 8.25 (s, 1H), 7.59 (t, J=7.8 Hz, 1H), 7.52 (dd, J=9.2, 0.8 Hz, 1H), 7.33 (dd, J=8.8, 2.0 Hz, 1H), 7.16 (d, J=7.6 Hz, 1H), 7.11 (d, J=7.6 Hz, 1H), 6.87 (d, J=12.4 Hz, 1H), 6.82 (d, J=12.4 Hz, 1H), 2.50 (s, 3H). Wherein 6.87 (d, J=12.4 Hz, 1H), 6.82 (d, J=12.4 Hz, 1H) is the compound displacement and coupling constant of the hydrogen on the carbon-carbon double bond.

Synthetic Route of Compound 2

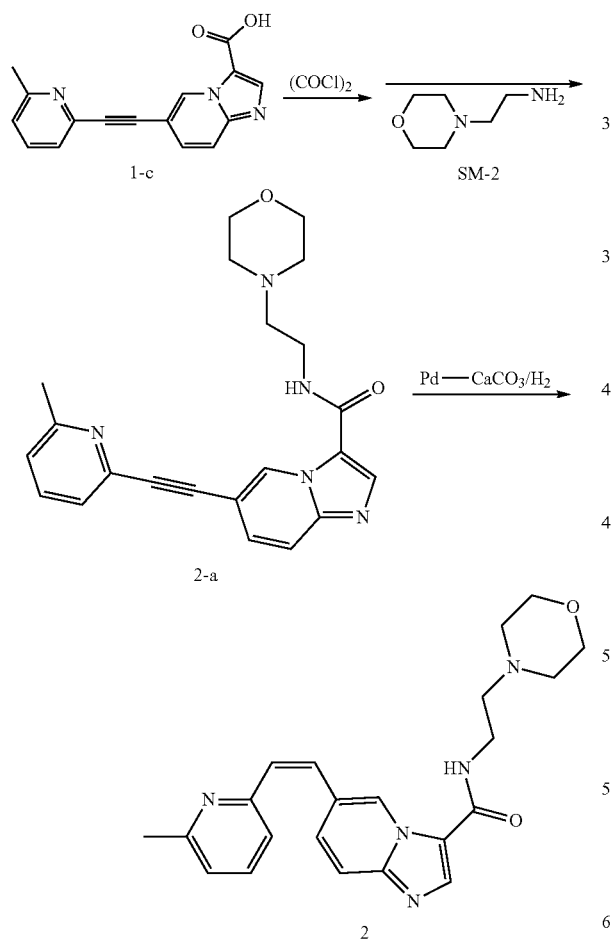

1 hour, it was concentrated, and added with dichloromethane (10 mL). A solution of SM-2 (93.9 mg, 0.72 mmol) in dichloromethane (10 mL) was slowly added to the solution under an ice bath, and the mixture was stirred overnight at room temperature. The next day, the mixture was concentrated. A crude product was purified by Prep-TLC (DCM:MeOH=10:1) to obtain compound 2-a (60 mg, 43%) as a white solid, LC-MS (ESI): m/z=390.1 [M+H]+.

Synthesis of Compound 2

Quinoline (40 mg, 0.3 mmol) and Pd—CaCO3 (20 mg) were added to a solution of compound 2-a (60 mg, 0.15 mmol) in ethyl acetate/methanol (v/v=2/1, 5 mL) at room temperature. The reaction solution was evacuated and replaced with H2 several times, and the mixture was stirred at room temperature for 2 hours. The mixture was filtered and concentrated. A crude was purified by Prep-HPLC to obtain compound 2 (20 mg, 33%) as a white solid. LC-MS (ESI): m/z=392.2 [M+H]+; 1H NMR (500 MHz, MeOD): δ 9.52 (s, 1H), 8.19 (s, 1H), 7.60 (t, J=7.5 Hz, 1H), 7.52 (d, J=9.5 Hz, 1H), 7.33 (dd, J=9.5 Hz, 1.5 Hz, 1H), 7.17 (d, J=8 Hz, 1H), 7.12 (d, J=8 Hz, 1H), 6.85 (d, J=12.5 Hz, 1H), 6.83 (d, J=12.5 Hz, 1H), 3.72-3.74 (m, 4H), 3.54-3.58 (m, 2H), 2.61-2.64 (m, 2H), 2.55-2.60 (m, 4H), 2.51 (s, 3H). Wherein 6.85 (d, J=12.5 Hz, 1H), 6.83 (d, j=12.5 Hz, 1H) is the compound displacement and coupling constant of the hydrogen on the carbon-carbon double bond.

Synthetic Route of Compound 3

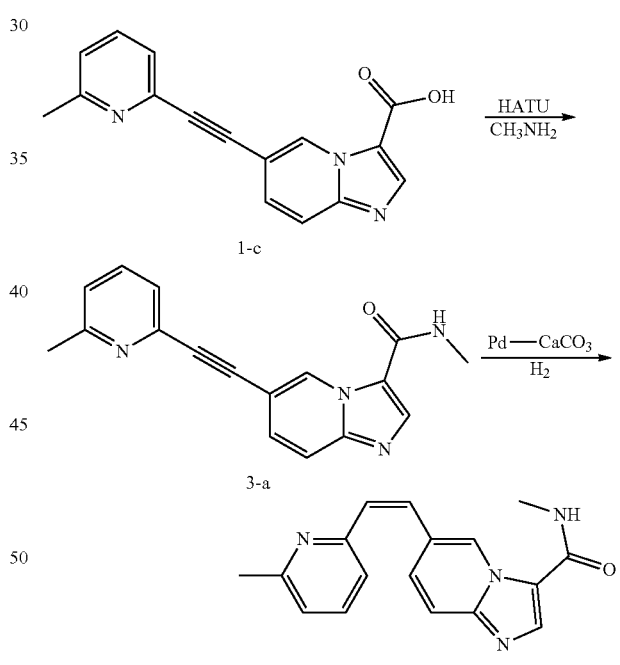

Synthesis of Compound 2-a

Oxalyl chloride (1 mL) was slowly added to a solution of compound 1-c (100 mg, 0.36 mmol) in dichloromethane (10 mL) under an ice bath, and then another drop of DMF was added. After the mixture was stirred at room temperature for Synthesis of Compound 3-a 1-c (100 mg, 0.36 mmol), DMF (8 mL), a methylamine tetrahydrofuran solution (2.0 M, 0.36 mL), HATU (274 mg, 0.72 mmol), and triethylamine (0.25 mL, 1.8 mmol) were added. The mixture was reacted at room temperature for 4 hours. After the reaction was completed, the mixture was added with water (100 mL), and extracted with ethyl acetate (30 mL×3). The organic phase was washed successively with water, a saturated aqueous sodium chloride solution, and dried over anhydrous sodium sulfate. The mixture was filtered and subjected to rotary evaporation. A crude product was purified by column chromatography (DCM:MeOH=20:1) to obtain compound 3-a (70 mg, 67%) a yellow solid. LC-MS (ESI): m/z=291.1 [M+H]$^+$.

Synthesis of Compound 3

Pd—CaCO$_3$ (30 mg) was added to a solution of compound 3-a (70 mg, 0.24 mmol) in pyridine (10 mL) at room temperature. The reaction solution was evacuated and replaced with H$_2$ several times, and the mixture was stirred overnight at room temperature. The mixture was filtered and concentrated. A crude was purified by Prep-HPLC to obtain compound 3 (20 mg, 31%) as a white solid. LC-MS (ESI): m/z=293.0 [M+H]$^+$; $^1$H NMR (500 MHz, MeOD): δ 9.51 (s, 1H), 8.14 (s, 1H), 7.59 (t, J=7.8 Hz, 1H), 7.50 (d, J=9.3 Hz, 1H), 7.31 (dd, J=9.3, 1.7 Hz, 1H), 7.17 (d, J=7.7 Hz, 1H), 7.11 (d, J=7.8 Hz, 1H), 6.86 (d, J=12.5 Hz, 1H), 6.82 (d, J=12.5 Hz, 1H), 2.92 (s, 3H), 2.50 (s, 3H). Wherein 6.86 (d, J=12.5 Hz, 1H), 6.82 (d, J=12.5 Hz, 1H) is the compound displacement and coupling constant of the hydrogen on the carbon-carbon double bond.

Synthetic Route of Compound 4

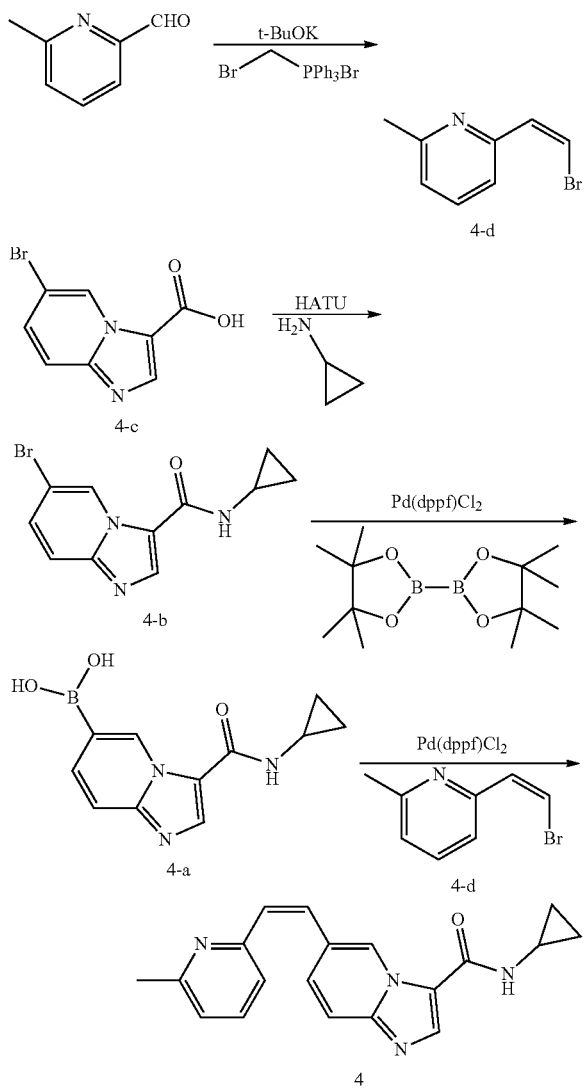

Synthesis of Compound 4-d

A solution of compound bromomethyltriphenylphosphonium bromide (2.16 g, 4.95 mmol) in tetrahydrofuran (10 mL) was cooled to −78° C. with a dry ice acetone bath under nitrogen protection, and potassium tert-butoxide (0.56 g, 4.95 mmol) was slowly added. The resulting mixture was reacted at −78° C. for 1 hour, and then 6-methyl-2-pyridinecarboxaldehyde (0.5 g, 4.95 mmol) was added dropwise. After the addition was completed, the mixture was kept at the temperature and stirred for 5 hours. The mixture was slowly heated to room temperature and stirred overnight. The next day, the reaction solution was diluted with petroleum ether, filtered, and concentrated. A crude product was purified by column chromatography (petroleum ether/ethyl acetate=10:1) to obtain compound 4-d (500 mg, 51%). LC-MS (ESI): m/z=197.9 [M+H]$^+$; $^1$H NMR (500 MHz, DMSO-d$_6$): δ 7.73-7.75 (m, 2H), 7.26 (d, J=8 Hz, 1H), 7.22 (dd, J=7.5 Hz, 2 Hz, 1H), 6.90 (d, J=8 Hz, 1H), 2.48 (s, 3H).

Synthesis of Compound 4-c

Compound 4-c was synthesized according to the method of WO 2015/157093.

Synthesis of Compound 4-b

Compound 4-c (0.3 g, 1.24 mmol), DCM (3 mL), THF (20 mL), and HATU (943 mg, 2.48 mmol) were added to a reaction flask. After the mixture was stirred at room temperature for half an hour, cyclopropylamine (0.13 mL, 1.88 mmol) and DIPEA (1.08 mL, 6.2 mmol) were added, and the mixture was stirred at room temperature for 4 hours.

The reaction mixture was concentrated, added with water, and extracted with ethyl acetate (30 mL×2). The organic phase was dried over anhydrous sodium sulfate. The mixture was filtered and subjected to rotary evaporation. A crude product was purified by column chromatography (DCM:MeOH=50:1) to obtain crude compound 4-b (350 mg) as yellow oil. LC-MS (ESI): m/z=280.0[M+H]$^+$.

Synthesis of Compound 4-a 4-b (0.35 g, 1.24 mmol), bis(pinacolato)diboron (381 mg, 1.5 mmol), Pd(dppf)Cl$_2$ (92 mg, 0.125 mmol), potassium acetate (245 mg, 2.5 mmol), 1,4-dioxane (20 mL) and toluene (4 mL) were added to a reaction flask. The reaction mixture was replaced with N$_2$ and reacted overnight at 90° C. After the reaction was completed, the mixture was concentrated to remove organic solvents. A crude product was purified by column chromatography (DCM:MeOH=20:1) to obtain compound 4-a (0.3 g, 97%) as a black solid. LC-MS (ESI): m/z=246.1 [M+H]$^+$.

Synthesis of Compound 4

4-a (300 mg, 1.22 mmol), 4-d (241 mg, 1.22 mmol), Pd(dppf)Cl$_2$ (89 mg, 0.122 mmol), sodium carbonate (259 mg, 2.44 mmol) 1,4-dioxane (15 mL) and water (3 mL) were added to a reaction flask. The reaction mixture was replaced with N$_2$ and reacted overnight at 90° C. After the reaction was completed, the mixture to remove organic solvents. A crude product was purified by column chromatography (DCM:MeOH=20:1) and Prep-HPLC to obtain compound 4 (20 mg, 5%). LC-MS (ESI): m/z=319.0 [M+H]$^+$; $^1$H NMR (500 MHz, MeOD): δ 9.51 (s, 1H), 8.16 (s, 1H), 7.56 (t, J=7.8 Hz, 1H), 7.48 (d, J=9.3 Hz, 1H), 7.29 (dd, J=9.3, 1.6 Hz, 1H), 7.14 (d, J=7.7 Hz, 1H), 7.08 (d, J=7.7 Hz, 1H), 6.83 (d, J=12.5 Hz, 1H), 6.79 (d, J=12.5 Hz, 1H), 2.82 (m, 1H), 2.48 (s, 3H), 0.84-0.80 (m, 2H), 0.71-0.59 (m, 2H). Wherein 6.83 (d, J=12.5 Hz, 1H), 6.79 (d, J=12.5 Hz, 1H) is the compound displacement and coupling constant of the hydrogen on the carbon-carbon double bond.

Synthetic Route of Compound 5

Synthetic Route of Compound 6

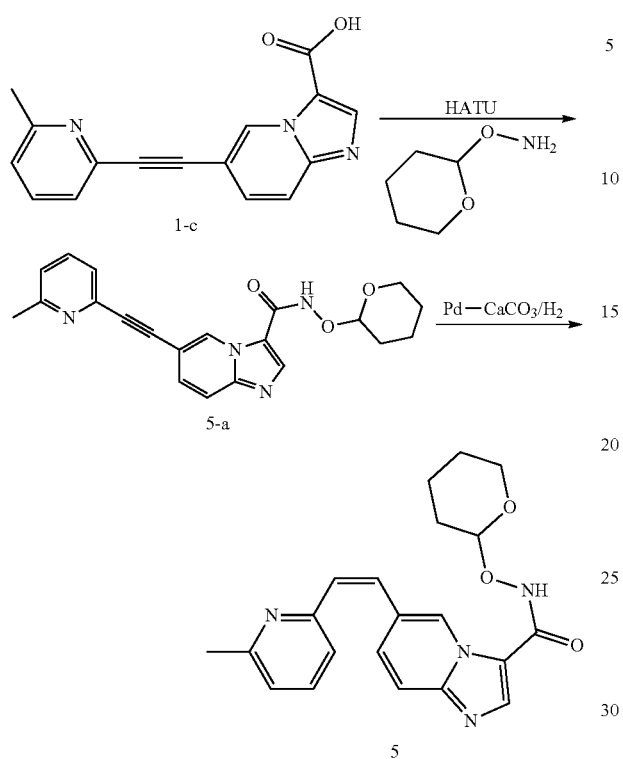

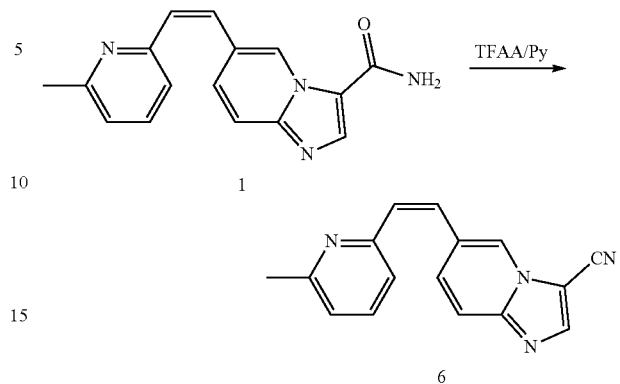

Synthesis of Compound 6

Pyridine (180 mg, 2.28 mmol) and trifluoroacetic anhydride (241 mg, 1.15 mmol) were added to a solution of compound 1 (0.16 g, 0.57 mmol) in THF (5 mL) and DCM (5 mL), and the mixture was stirred at room temperature for 2 hours. The mixture was concentrated, dissolved in ethyl acetate (30 mL), washed with 1 M hydrochloric acid solution and saturated sodium bicarbonate solution. The organic phase was dried over anhydrous sodium sulfate. The mixture was filtered and subjected to rotary evaporation.

A crude product was purified by column chromatography (DCM:MeOH=30:1) and Prep-HPLC to obtain compound 6 (30 mg, 20%) as a white solid. LC-MS (ESI): m/z=261.1 [M+H]$^+$; $^1$H NMR (500 MHz, MeOD): δ 8.86 (s, 1H), 8.26 (s, 1H), 7.70-7.60 (m, 2H), 7.47 (dd, J=9.4, 1.6 Hz, 1H), 7.22 (d, J=7.7 Hz, 1H), 7.17 (d, J=7.7 Hz, 1H), 6.90 (d, J=12.5 Hz, 1H), 6.86 (d, J=12.5 Hz, 1H), 2.54 (s, 3H). Wherein 6.90 (d, J=12.5 Hz, 1H), 6.86 (d, J=12.5 Hz, 1H) is the compound displacement and coupling constant of the hydrogen on the carbon-carbon double bond.

Synthetic Route of Compound 7

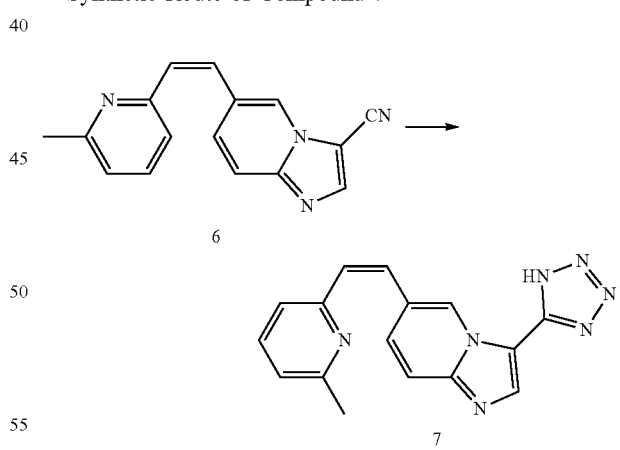

Synthesis of Compound 5-a

Compound 1-c (0.55 g, 1.98 mmol), DMF (10 mL), THF (20 mL) and HATU (1.5 g, 3.96 mmol) were added to a reaction flask. After the mixture was stirred at room temperature for half an hour, o-(tetrahydro-2hydro-pyran-2-yl) hydroxylamine (0.23 g, 1.98 mmol) and triethylamine (0.6 g, 5.94 mmol) were added. After the mixture was stirred at room temperature overnight, it was concentrated, added with water, and extracted with ethyl acetate (30 mL×3). The organic phase was dried over anhydrous sodium sulfate. The mixture was filtered and subjected to rotary evaporation. A crude product was purified by Prep-TLC (DCM:MeOH=20:1) to obtain compound 5-a (200 mg, 27%). LC-MS (ESI): m/z=377.0 [M+H]$^+$.

Synthesis of Compound 5

Pd—CaCO$_3$ (100 mg) was added to a solution of compound 5-a (38 mg, 0.10 mmol) in pyridine (10 mL) at room temperature. The reaction solution was evacuated and replaced with H$_2$ several times, and the mixture was stirred overnight at room temperature. The mixture was filtered and concentrated. A crude was purified by Prep-HPLC to obtain compound 5 (5 mg, 13%) as a white solid. LC-MS (ESI): m/z=379.0 [M+H]$^+$; $^1$H NMR (500 MHz, MeOD): δ 9.43 (s, 1H), 8.18 (s, 1H), 7.60 (t, J=7.8 Hz, 1H), 7.55 (d, J=9.4 Hz, 1H), 7.37 (dd, J=9.3, 1.5 Hz, 1H), 7.18 (d, J=7.7 Hz, 1H), 7.13 (d, J=7.8 Hz, 1H), 6.83 (d, J=12.5 Hz, 1H), 6.79 (d, J=12.5 Hz, 1H), 5.05 (s, 1H), 4.14 (t, J=10.7 Hz, 1H), 3.66 (d, J=11.6 Hz, 1H), 2.87 (s, 1H), 2.50 (s, 3H), 2.01-1.69 (m, 5H). Wherein 6.83 (d, J=12.5 Hz, 1H), 6.79 (d, J=12.5 Hz, 1H) is the compound displacement and coupling constant of the hydrogen on the carbon-carbon double bond.

Synthesis of Compound 7

Compound 6 (28 mg, 0.11 mmol), DMF (6 mL), azido-trimethylsilane (25 mg, 0.22 mmol), and ammonium fluoride (12 mg, 0.33 mmol) were added to a reaction flask. After the mixture was stirred at 70° C. for 4 hours, it was subjected to rotary evaporation and purify by Prep-HPLC to obtain compound 7 (3 mg, 9%) as a white solid. LC-MS (ESI): m/z 304.0[M+H]$^+$; $^1$H NMR (500 MHz, MeOD): δ 9.51 (s, 1H), 8.12 (s, 1H), 7.60 (t, J=7.8 Hz, 1H), 7.51 (d, J=9.3 Hz, 1H), 7.26 (dd, J=9.4, 1.6 Hz, 1H), 7.17 (dd, J=7.7, 4.1 Hz, 2H), 6.96 (d, J=12.5 Hz, 1H), 6.85 (d, J=12.5 Hz, 1H), 2.47 (s, 3H). Wherein 6.96 (d, J=12.5 Hz, 1H), 6.85 (d, J=12.5 Hz, 1H) is the compound displacement and coupling constant of the hydrogen on the carbon-carbon double bond.

Synthetic Route of Compound 8

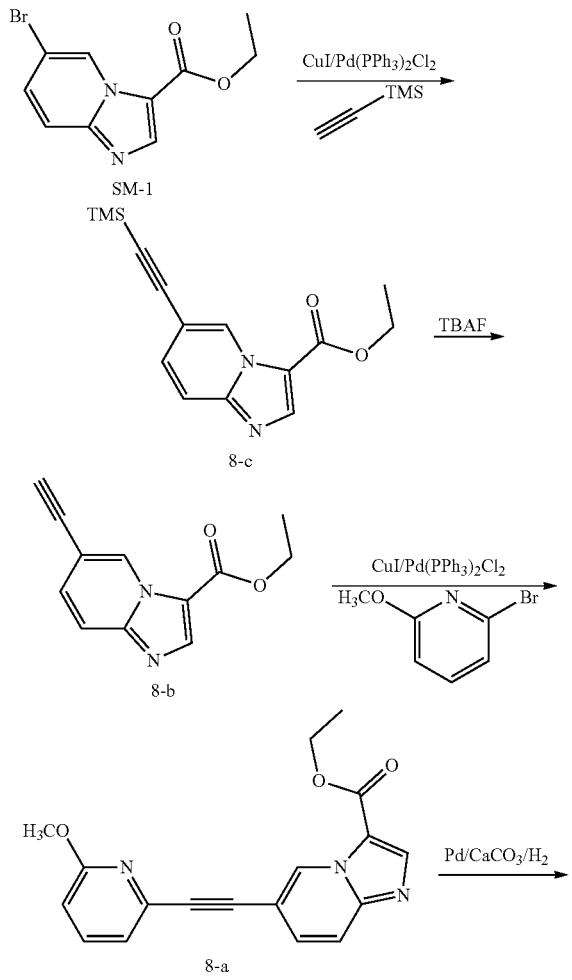

Synthesis of Compound 8-c

A mixture of compounds SM-1 (5.4 g, 20 mmol), trimethylsilylacetylene (4 g, 40 mmol), PdCl$_2$(PPh$_3$)$_2$ (1.4 g, 2 mmol), cuprous iodide (0.38 g, 2 mmol) and triethylamine (100 mL) was reacted at room temperature for 12 hours under a nitrogen atmosphere. The mixture was subjected to rotary evaporation to remove the organic phase, and purified by column chromatography (EA:PE=1:5) to obtain compound 8-c (2.86 g, 50%) as a yellow solid. LC-MS (ESI): m/z=287.0 [M+H]$^+$.

Synthesis of Compound 8-b 8-c (2.86 g, 10 mmol) was added to THF (100 mL), and a TBAF solution (1 M, 20 mmol, 20 mL) was added. The mixture was stirred at room temperature for 2 hours. After the reaction was completed, the mixture was concentrated under reduced pressure to remove organic solvents, and water (1000 mL) and DCM (500 mL) were added. The liquid was separated, subjected to rotary evaporation to remove the organic phase, and purified by column chromatography (EA:PE=1:5 then 1:3) to obtain compound 8-c (1.6 g, 75%) as a yellow solid. LC-MS (ESI): m/z=215.1 [M+H]$^+$.

Synthesis of Compound 8-a 8-b (1.1 g, 5.1 mmol), and 2-bromo-6-methoxypyridine (1.1 g, 5.85 mmol) were added to triethylamine (20 mL) and cuprous iodide (0.1 g, 0.5 mmol) and PdCl$_2$(PPh$_3$)$_2$ (0.35 g, 0.5 mmol) were added. The mixture was stirred at room temperature for 3 hours. After the reaction was completed, the mixture was concentrated under reduced pressure to remove organic solvents, and water (100 mL) and DCM (50 mL) were added. The mixture was purified by column chromatography (PE/EA=5/1) to obtain compound 8-a (0.86 g, 5,2%). LCMS (ESI): m/z=322.0 [M+H]$^+$.

Synthesis of Compound 8

Compound 8-a (0.64 g, 2.0 mmol), Pd/CaCO$_3$ (0.1 g) and pyridine (10 mL) were mixed at room temperature. After replaced with hydrogen, the mixture was stirred at room temperature for 16 hours, filtered, concentrated, and subjected to column chromatography (PE/EA=5/1) to obtain solid 8 (0.36 g, 56%). LC-MS (ESI): m/z=324.1 [M+H]$^+$; $^1$H NMR (500 MHz, CDCl$_3$): δ 9.31 (s, 1H), 8.27 (s, 1H), 7.59 (d, J=9.5 Hz, 1H), 7.56 (s, 1H), 7.43-7.53 (m, 2H), 6.81 (d, J=6.0 Hz, 1H), 6.71 (d, J=12.5 Hz, 1H), 6.68 (d, J=12.5 Hz, 1H), 6.60 (d, J=8.5 Hz, 1H), 4.40 (q, J=7.0 Hz, 2H), 3.53 (s, 3H), 1.40 (t, J=7.0 Hz, 3H). Wherein 6.71 (d, J=12.5 Hz, 1H), 6.68 (d, J=12.5 Hz, 1H) is the compound displacement and coupling constant of the hydrogen on the carbon-carbon double bond.

Synthetic Route of Compound 9

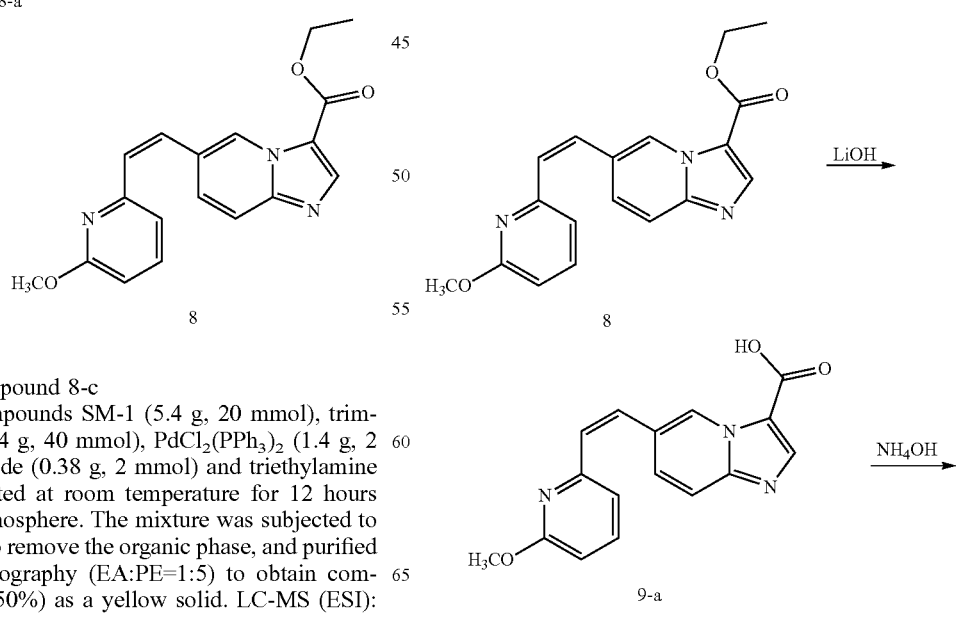

-continued

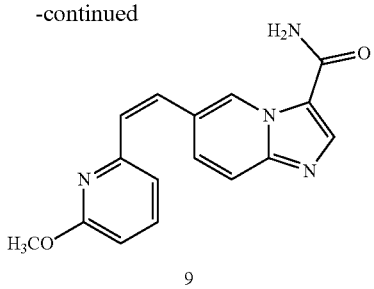

9

Synthesis of Compound 9-a 8 (0.323 g, 1.0 mmol) was added to methanol (2 mL) and THF (8 mL), and lithium hydroxide monohydrate (0.42 g, 10 mmol) aqueous solution was added. The mixture was stirred at room temperature for 2 hours. After the reaction was completed, the mixture was concentrated under reduced pressure to remove organic solvents, water (50 mL) and DCM (10 mL) were added. The liquid was separated, and the organic layer was discarded. The water layer was cooled to 0° C. and neutralized with hydrochloric acid (2 M) to pH 6 to 7. A brown precipitate was filtered off and dried to obtain compound 9-a (0.19 g, 64%). LCMS (ESI): m/z=296.0 [M+H]$^+$.

Synthesis of Compound 9

A mixture of 9-a (0.15 g, 0.5 mmol) was dissolved in dichloromethane (100 mL). Under an ice bath, oxalyl chloride (5 mL) was added to the solution and DMF (0.5 mL) was slowly added to the reaction solution. After the reaction solution was heated to room temperature, the reaction was continued for 6 hours. The reaction solution was concentrated under reduced pressure to dryness, and then diluted with dichloromethane (40 mL). Under an ice bath, the solution was slowly added dropwise to aqueous ammonia (50 mL), reacted at 0° C. for 10 minutes, and then heated to room temperature and stirred for 2 hours. The mixture was concentrate to remove the methylene chloride solution, and then water (60 mL) was added to the aqueous phase to dilute and stir vigorously for 1 hour. The mixture was filtered, washed and dried to obtain compound 9 (0.06 g, 41%) as a white solid. LC-MS (ESI): m/z=295.0 [M+H]$^+$; $^1$H NMR (500 MHz, MeOD): δ 9.56 (s, 1H), 8.27 (s, 1H), 7.50-7.64 (m, 3H), 6.90 (d, J=7.5 Hz, 1H), 6.79 (d, J=12.5 Hz, 1H), 6.74 (d, J=12.5 Hz, 1H), 6.63 (d, J=8.5 Hz, 1H), 3.45 (s, 3H). Wherein 6.79 (d, J=12.5 Hz, 1H), 6.74 (d, J=12.5 Hz, 1H) is the compound displacement and coupling constant of the hydrogen on the carbon-carbon double bond.

Synthetic Route of Compound 10

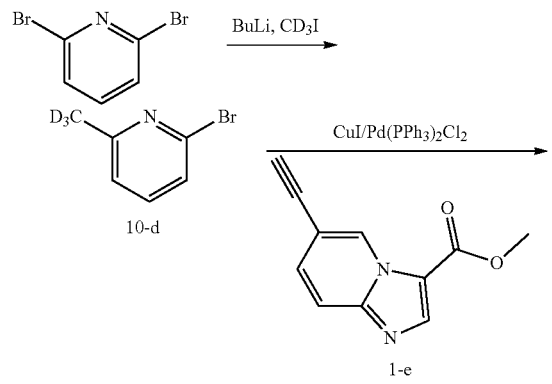

Synthesis of Compound 10-d 2,6-Dibromopyridine (1 g, 4.22 mmol) was dissolved in tetrahydrofuran (10 mL) and cooled to −78° C., and then n-butyllithium (2.5 M, 2.03 mL, 5.07 mmol) was slowly added. The reaction solution was reacted at low temperature for half an hour, added with deuterated methyl iodide (0.32 mL, 5.07 mmol), and heated to normal temperature and stirred for another hour. The reaction solution was quenched with water (10 mL), and extracted with ethyl acetate (10 mL×3). The organic phase was combined, and dried over anhydrous sodium sulfate. The mixture was filtered, and concentrated to obtain compound 10-d (0.5 g, 67%) as a brown liquid. LC-MS (ESI): m/z=175.0 [M+H]$^+$.

Synthesis of Compound 10-c 1-e (200 mg, 1 mmol), 10-d (192 mg, 1.1 mmol), bis(triphenylphosphine) palladium dichloride (70 mg, 0.1 mmol), cuprous iodide (19 mg, 0.1 mmol) and triethylamine (15 mL) were added to a reaction flask. The reaction mixture was replaced with N$_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (PE:EA=1:1) to obtain compound 10-c (60 mg, 20%) as a yellow solid. LC-MS (ESI): m/z=295.0 [M+H]$^+$.

-continued

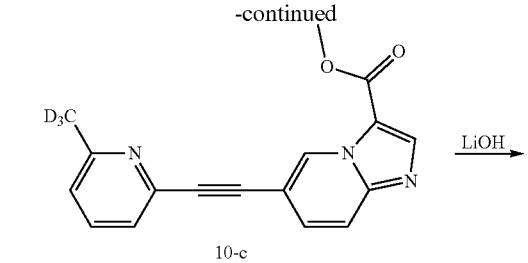
10-c

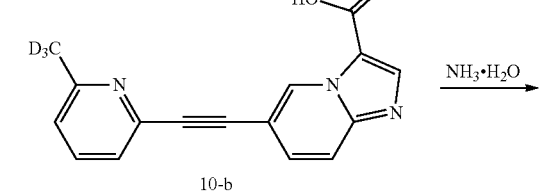
10-b

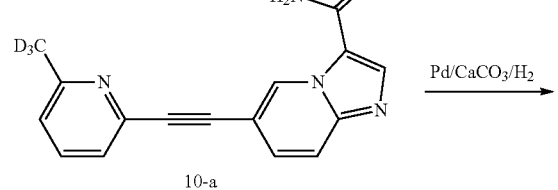
10-a

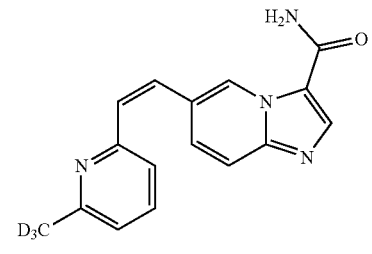
10

Synthesis of Compound 10-b

Compound 10-c (60 mg, 0.2 mmol), tetrahydrofuran (6 mL), methanol (6 mL), water (3 mL), and lithium hydroxide monohydrate (34.2 mg, 0.8 mmol) were added to a reaction flask. After the mixture was stirred at room temperature overnight, it was added with dilute hydrochloric acid to adjust the pH to 6 to 7, and extracted with ethyl acetate (30 mL×3). The organic phase was washed successively with water, saturated aqueous sodium chloride solution, and dried over anhydrous sodium sulfate. The mixture was filtered and subjected to rotary evaporation to obtain a crude compound 10-b (30 mg, 53%). LC-MS (ESI): m/z=281.1 [M+H]$^+$.

Synthesis of Compound 10-a

Oxalyl chloride (1 mL) was slowly added to a solution of compound 10-b (30 mg, 0.11 mmol) in dichloromethane (10 mL) under an ice bath, and then another drop of DMF was added. The mixture was stirred at room temperature for 1 hour, and concentrated to obtain a crude. The above crude product in dichloromethane (10 mL) was added slowly to aqueous ammonia (5 mL) under an ice bath. The mixture was stirred overnight at room temperature and concentrated. The crude product was purified by Prep-TLC (DCM:MeOH=10:1) to obtain compound 10-a (15 mg, 50%) as a white solid. LC-MS (ESI): m/z=280.2 [M+H]$^+$.

Synthesis of Compound 10

Pd—CaCO$_3$ (10 mg) was added to a solution of compound 10-a (15 mg, 0.05 mmol) in pyridine (10 mL) at room temperature. The reaction solution was evacuated and replaced with H$_2$ several times. The mixture was stirred overnight at room temperature, filtered and concentrated. The crude product was purified by Prep-HPLC to obtain compound 10 (5 mg, 33%) as a white solid. LC-MS (ESI): m/z=282.1 [M+H]$^+$; $^1$H NMR (500 MHz, MeOD): δ 9.54 (s, 1H), 8.25 (s, 1H), 7.60 (t, J=8.0 Hz, 1H), 7.53 (d, J=9.0 Hz, 1H), 7.35 (d, J=8.0 Hz, 1H), 7.17 (d, J=7.5 Hz, 1H), 7.12 (d, J=7.5 Hz, 1H), 6.88 (d, J=12 Hz, 1H), 6.83 (d, J=12 Hz, 1H). Wherein 6.88 (d, J=12 Hz, 1H), 6.83 (d, J=12 Hz, 1H) is the compound displacement and coupling constant of the hydrogen on the carbon-carbon double bond.

Synthetic Route of Compound 11

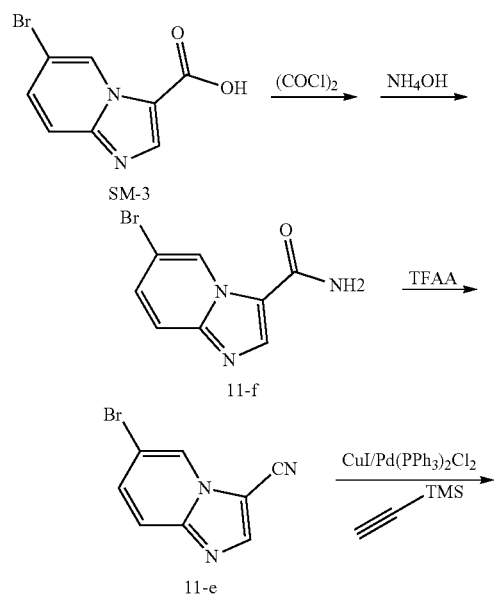

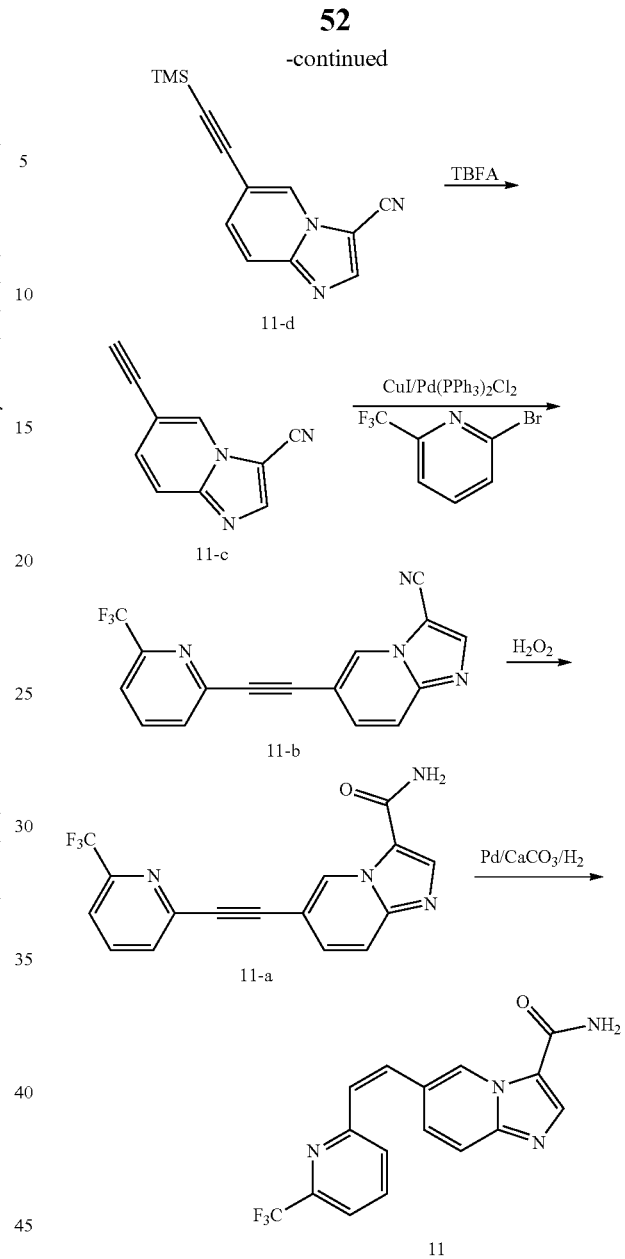

Synthesis of Compound 11-f

SM-3 (500 mg, 2.07 mmol) was dissolved in dichloromethane (10 mL). Under an ice bath, oxalyl chloride (1 mL) and a drop of DMF were slowly added to the solution. The reactants were heated to room temperature and reacted for 60 minutes. The reactants were concentrated under reduced pressure and diluted with dichloromethane (5 mL). Under an ice bath, aqueous ammonia (5 mL) was slowly added dropwise. The reaction mixture was reacted at 0° C. for 10 minutes, and then heated to room temperature and stirred overnight. The liquid was separated and the aqueous layer was extracted with dichloromethane. The organic phases were combined, washed with water and brine, and dried over anhydrous sodium sulfate. Compound 11-f (300 mg, 60%) was obtained as a white solid by concentration. LC-MS (ESI): m/z=239.9 [M+H]$^+$.

Synthesis of Compound 11-e 11-f (100 mg, 0.42 mmol) was dissolved in dioxane (10 mL). Under an ice bath, pyridine (0.34 mL, 4.2 mmol) was added to the solution, and after stirring for 5 minutes, trifluoroacetic anhydride (0.29 mL, 2.08 mmol) was slowly added dropwise. The reactants were heated to room temperature and stirred for 5 hours. After the reaction was completed, water was added to quench the reaction, and the organic solvents was removed by concentration under reduced pressure. The mixture was dissolved in ethyl acetate, washed with water, washed with saturated brine, dried over anhydrous sodium sulfate, and concentrated to obtain compound 11-e (80 mg, 86%) as a white solid. LC-MS (ESI): m/z=221.9 [M+H]$^+$.

Synthesis of Compound 11-d 11-e (0.5 g, 2.25 mmol), trimethylsilylacetylene (0.24 g, 2.48 mmol), bis(triphenylphosphine) palladium dichloride (31.6 mg, 0.045 mmol), cuprous iodide (8.6 mg, 0.045 mmol) and triethylamine (15 mL) were added to a reaction flask. The reaction mixture was replaced with N$_2$ and reacted at 20° C. for 2 hours. After the reaction was completed, the reaction mixture was concentrated to remove organic solvents, added with water (30 mL), and extracted with ethyl acetate (30 mL). The organic phase was washed successively with water and a saturated aqueous sodium chloride solution, and dried over anhydrous sodium sulfate. The mixture was filtered and subjected to rotary evaporation. A crude product was purified by column chromatography (PE:EA=4:1) to obtain compound 11-d (0.5 g, 92%) as a yellow solid. LC-MS (ESI): m/z=240.1 [M+H]$^+$.

Synthesis of Compound 11-c

A solution of tetrabutylammonium fluoride in tetrahydrofuran (1M, 6.68 mL, 6.68 mmol) was added to a solution of compound 11-d (0.5 g, 2.09 mmol) in tetrahydrofuran (10 mL). The mixture was stirred at room temperature for 2 hours, concentrated to remove organic solvents, added with water (20 mL), and extracted with ethyl acetate (30 mL×2). The organic phase was washed successively with water, saturated aqueous sodium chloride solution, and dried over anhydrous sodium sulfate. The mixture was filtered and subjected to rotary evaporation. A crude product was purified by silica gel column chromatography (PE:EA=4:1) to obtain compound 11-c (250 mg, 72%) as a yellow solid. LC-MS (ESI): m/z=168.1 [M+H]$^+$.

Synthesis of Compound 11-b 11-c (250 mg, 1.50 mmol), 2-bromo-6-trifluoromethylpyridine (371.8 mg, 1.65 mmol), bis(triphenylphosphine) palladium dichloride (21 mg, 0.03 mmol), cuprous iodide (5.7 mg, 0.03 mmol) and tri ethyl amine (15 mL) were added to a reaction flask. The reaction mixture was replaced with N$_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (PE:EA=3:1) to obtain compound 11-b (100 mg, 21%) as a yellow solid. LC-MS (ESI): m/z=313.0 [M+H]$^+$.

Synthesis of Compound 11-a

Compound 11-b (60 mg, 0.19 mmol), potassium carbonate (4 mg, 0.029 mmol), and dimethyl sulfoxide (2 mL) were added to a reaction flask. Under an ice bath, H$_2$O$_2$ (26.1 mg, 0.77 mmol) was added dropwise. After the addition was completed, the mixture was stirred overnight at room temperature. The next day, the mixture was filtered, and the filter cake was washed with water and dried to obtain compound 11-a (50 mg, 79%) as a white solid. LC-MS (ESI): m/z=331.0 [M+H]$^+$.

Synthesis of Compound 11

Pd—CaCO$_3$ (20 mg) was added to a solution of compound 11-a (50 mg, 0.15 mmol) in pyridine (10 mL) at room temperature. The reaction solution was evacuated and replaced with H$_2$ several times, and the mixture was stirred overnight at room temperature, filtered and concentrated. A crude was purified by Prep-HPLC to obtain compound 11 (20 mg, 40%) as a white solid. LC-MS (ESI): m/z=333.1 [M+H]$^+$; $^1$H NMR (500 MHz, MeOD): δ 9.52 (s, 1H), 8.27 (s, 1H), 7.93 (t, J=8.5 Hz, 1H), 7.64 (d, J=7.5 Hz, 1H), 7.50-7.57 (m, 3H), 6.98 (d, J=12.5 Hz, 1H), 6.90 (d, J=12.5 Hz, 1H). Wherein 6.98 (d, J=12.5 Hz, 1H), 6.90 (d, J=12.5 Hz, 1H) is the compound displacement and coupling constant of the hydrogen on the carbon-carbon double bond.

Synthetic Route of Compound 12

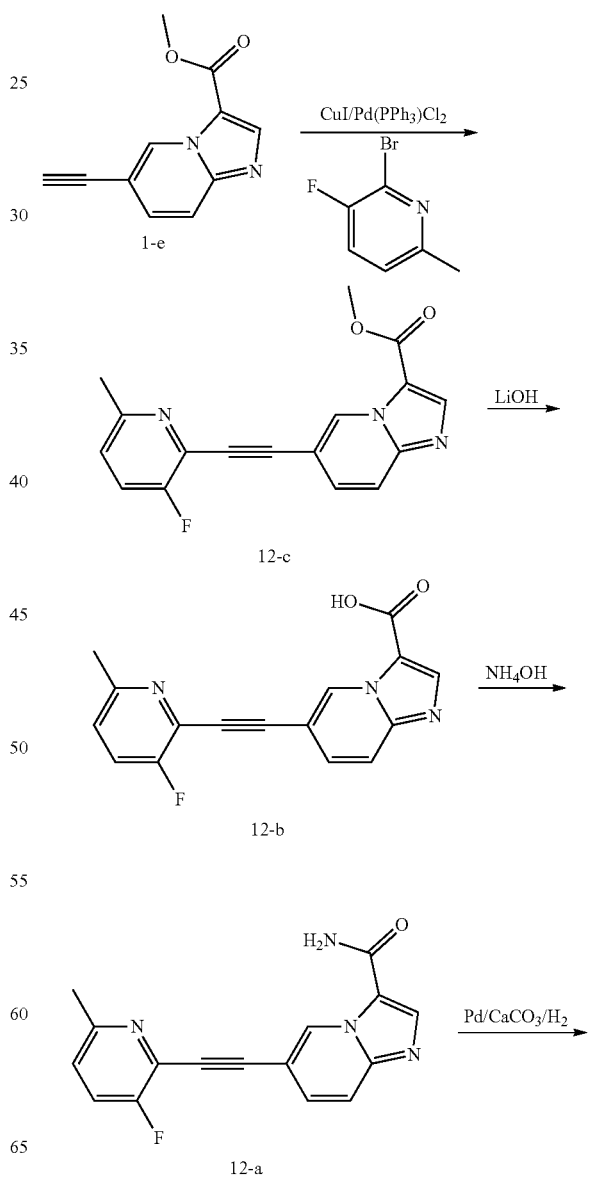

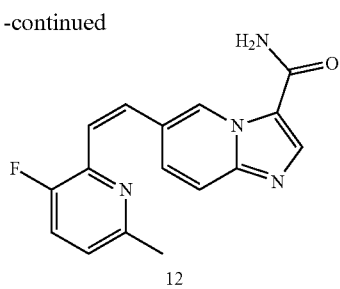

12

Synthesis of Compound 12-c 1-e (400 mg, 2 mmol), 2-bromo-3-fluoro-6-methylpyridine (417 mg, 2.2 mmol), his(triphenylphosphine) palladium dichloride (140 mg, 0.2 mmol), and cuprous iodide (38 mg, 0.2 mmol) and triethylamine (15 mL) were added to a reaction flask. The reaction mixture was replaced with $N_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (PE:EA=1:1) to obtain compound 12-c (400 mg, 65%) as a yellow solid. LC-MS (ESI): m/z=310.0 [M+H]$^+$.

Synthesis of Compound 12-b

Compound 12-c (400 mg, 1.29 mmol), tetrahydrofuran (6 mL), methanol (6 mL), water (3 mL) and lithium hydroxide monohydrate (217 mg, 5.17 mmol) were added to a reaction flask. After the mixture was stirred overnight at room temperature, it was added with dilute hydrochloric acid to adjust the pH to 6 to 7, and extracted with ethyl acetate (30 mL×3). The organic phase was washed successively with water and a saturated aqueous sodium chloride solution, and dried over anhydrous sodium sulfate. The mixture was filtered and subjected to rotary evaporation to obtain a crude compound 12-b (300 mg, 78%). LC-MS (ESI): m/z=296.0 [M+H]$^+$.

Synthesis of Compound 12-a

Oxalyl chloride (1 mL) was slowly added to a solution of compound 12-b (100 mg, 0.34 mmol) in dichloromethane (10 mL) under an ice bath, and then another drop of DMF was added. The mixture was stirred at room temperature for 1 hour, and concentrated to obtain a crude. The above crude product in dichloromethane (10 mL) was added slowly to aqueous ammonia (5 mL) under an ice bath. The mixture was stirred overnight at room temperature and concentrated. The crude product was purified by Prep-TLC (DCM:MeOH=10:1) to obtain compound 12-a (50 mg, 50%) as a white solid. LC-MS (ESI): m/z=295.0 [M+H]$^+$.

Synthesis of Compound 12

Pd—CaCO$_3$ (20 mg) was added to a solution of compound 12-a (50 mg, 0.17 mmol) in pyridine (10 mL) at room temperature. The reaction solution was evacuated and replaced with H$_2$ several times. The mixture was stirred overnight at room temperature, filtered and concentrated. The crude product was purified by Prep-HPLC to obtain compound 12 (17 mg, 40%) as a white solid. LC-MS (ESI): m/z=297.0 [M+H]$^+$; $^1$H NMR (500 MHz, MeOD): δ 9.58 (s, 1H), 8.25 (s, 1H), 7.53 (d, J=9.5 Hz, 1H), 7.46 (t, J=8.5 Hz, 1H), 7.41 (dd, J=9, 1.5 Hz, 1H), 7.25 (dd, J=8.5, 3.5 Hz, 1H), 6.96 (d, J=12.5 Hz, 1H), 6.82 (dd, j=12.5, 2 Hz, 1H), 2.43 (s, 3H). Wherein 6.96 (d, J=12.5 Hz, 1H), 6.82 (dd, J=12.5, 2 Hz, 1H) is the compound displacement and coupling constant of the hydrogen on the carbon-carbon double bond.

Synthetic Route of Compound 13

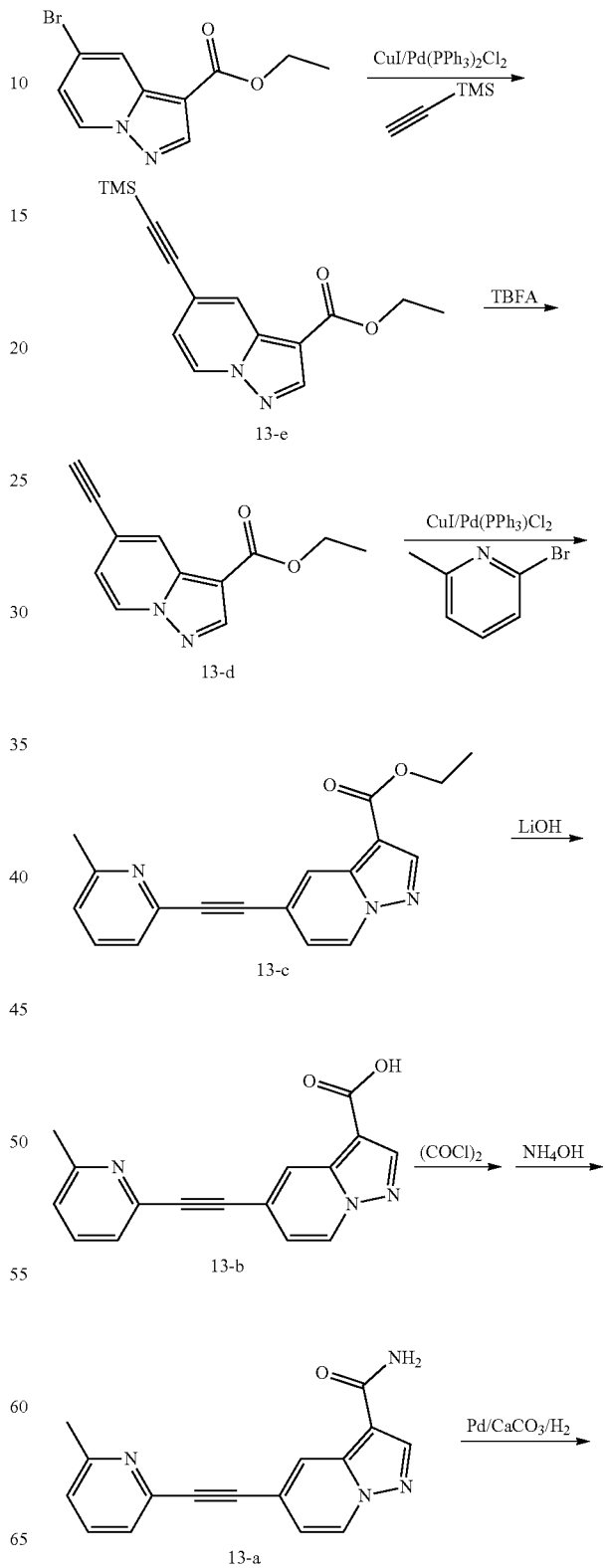

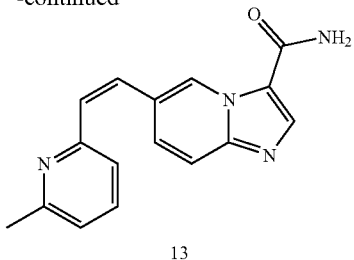

13

Synthesis of Compound 13-e

5-Bromopyrazolo[1,5-A]pyridine-3-carboxylate (2 g, 7.43 mmol), trimethylsilylacetylene (0.8 g, 8.18 mmol), his(triphenylphosphine) palladium dichloride (100 mg, 0.15 mmol), cuprous iodide (30 mg, 0.15 mmol) and triethylamine (15 mL) were added to a reaction flask. The reaction mixture was replaced with $N_2$ and reacted at 20° C. for 2 hours. After the reaction was completed, the reaction mixture was concentrated to remove organic solvents, added with water (30 mL), and extracted with ethyl acetate (30 mL). The organic phase was washed successively with water and a saturated aqueous sodium chloride solution, dried over anhydrous sodium sulfate, filtered, and subjected to rotary evaporation. A crude product was purified by column chromatography (PE:EA=4:1) to obtain compound 13-e (0.8 g, 38%) as a yellow solid. LC-MS (ESI): m/z=287.0 [M+H]$^+$.

Synthesis of Compound 13-d

A solution of tetrabutylammonium fluoride in tetrahydrofuran (1M, 5.6 mL, 5.6 mmol) was added to a solution of compound 13-e (0.8 g, 2.79 mmol) in tetrahydrofuran (10 mL). The mixture was stirred at room temperature for 2 hours, concentrated to remove organic solvents, added with water (20 mL), and extracted with ethyl acetate (30 mL×2). The organic phase was washed successively with water, saturated aqueous sodium chloride solution, and dried over anhydrous sodium sulfate. The mixture was filtered and subjected to rotary evaporation. A crude product was purified by silica gel column chromatography (PE:EA=4:1) to obtain compound 13-d (500 mg, 83%) as a yellow solid. LC-MS (ESI): m/z=215.3 [M+H]$^+$.

Synthesis of Compound 13-c 13-d (500 mg, 2.33 mmol), 2-bromo-6-methylpyridine (441.7 mg, 2.57 mmol), bis(triphenylphosphine) palladium dichloride (32.8 mg, 0.047 mmol), cuprous iodide (9 mg, 0.047 mmol) and triethylamine (15 mL) were added to a reaction flask. The reaction mixture was replaced with $N_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, dried over anhydrous sodium sulfate, filtered, and subjected to rotary evaporation. A crude product was purified by column chromatography (PE:EA=3:1) to obtain compound 13-c (400 mg, 56%) as a yellow solid. LC-MS (ESI): m/z=306.0 [M+H]$^+$.

Synthesis of Compound 13-b

Compound 13-c (400 mg, 1.31 mmol), tetrahydrofuran (6 mL), methanol (6 mL), water (3 mL), and lithium hydroxide monohydrate (220 mg, 5.24 mmol) were added to a reaction flask. After the mixture was stirred at room temperature overnight, it was added with dilute hydrochloric acid to adjust the pH to 6 to 7, and extracted with ethyl acetate (30 mL×3). The organic phase was washed successively with water, saturated aqueous sodium chloride solution, and dried over anhydrous sodium sulfate. The mixture was filtered and subjected to rotary evaporation to obtain a crude compound 13-b (250 mg, 69%). LC-MS (ESI): m/z=278.0 [M+H]$^+$.

Synthesis of Compound 13-a

Oxalyl chloride (1 mL) was slowly added to a solution of compound 13-b (250 mg, 0.9 mmol) in dichloromethane (10 mL) under an ice bath, and then another drop of DMF was added. The mixture was stirred at room temperature for 1 hour, and concentrated to obtain a crude. The above crude product in dichloromethane (10 mL) was added slowly to aqueous ammonia (5 mL) under an ice bath. The mixture was stirred overnight at room temperature and concentrated. The crude product was purified by Prep-TLC (DCM:MeOH=10:1) to obtain compound 13-a (200 mg, 80%) as a white solid. LC-MS (ESI): m/z=277.0 [M+H]$^+$.

Synthesis of Compound 13

Pd—CaCO$_3$ (20 mg) was added to a solution of compound 13-a (40 mg, 0.15 mmol) in pyridine (10 mL) at room temperature. The reaction solution was evacuated and replaced with $H_2$ several times. The mixture was stirred overnight at room temperature, filtered and concentrated. A crude product was purified by Prep-HPLC to obtain compound 13 (20 mg, 49%) as a white solid. LC-MS (ESI): m/z=279.0 [M+H]$^+$; $^1$H NMR (500 MHz, MeOD): δ 8.4-8.43 (m, 2H), 8.18 (s, 1H), 7.58 (t, J=7.5 Hz, 1H), 7.17 (d, J=8 Hz, 1H), 7.12 (d, J=8 Hz, 1H), 6.90 (d, J=12.5 Hz, 1H), 6.85 (d, J=12.5 Hz, 1H), 6.81 (dd, J=7, 2 Hz, 1H), 2.51 (s, 3H). Wherein 6.90 (d, j=12.5 Hz, 1H), 6.85 (d, J=12.5 Hz, 1H) is the compound displacement and coupling constant of the hydrogen on the carbon-carbon double bond.

Synthetic Route of Compound 14

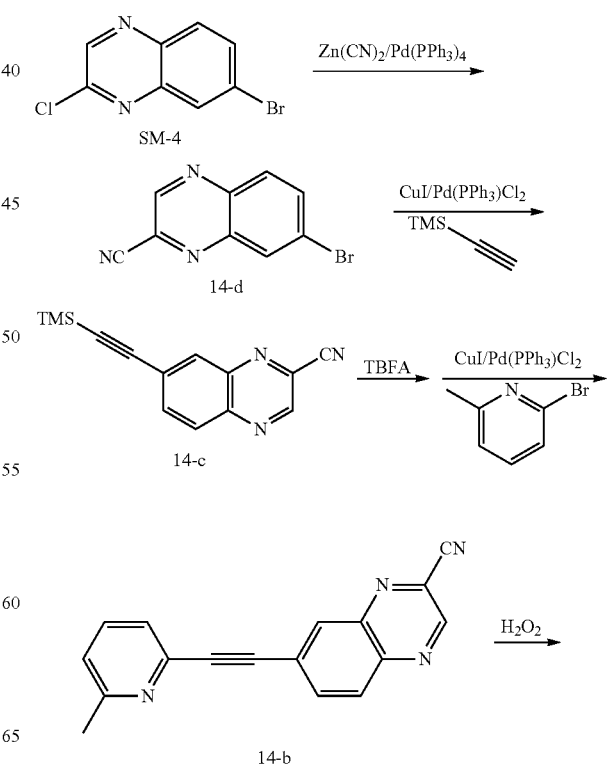

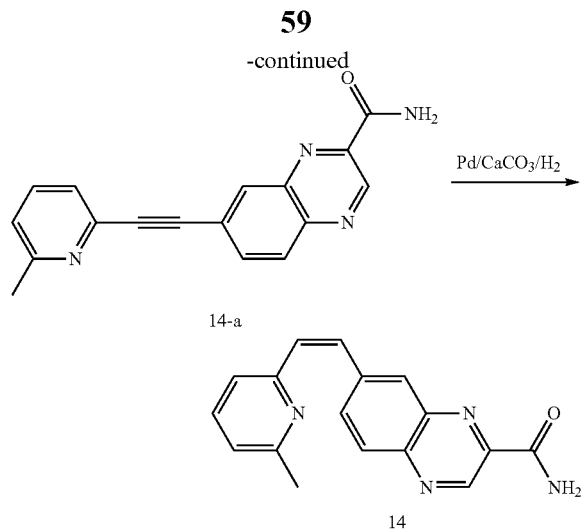

Synthesis of Compound 14-d

Compounds zinc cyanide (602 mg, 5.13 mmol), 7-bromo-2-chloroquinoxaline (2.5 g, 10.27 mmol), tetratriphenylphosphine palladium (1.2 g, 1.03 mmol) and DMF (10 mL) were added to a reaction flask. The reaction solution was replaced with $N_2$ and stirred overnight at 80° C. The reaction solution was diluted with ethyl acetate, washed with water, washed with saturated brine, and dried over anhydrous sodium sulfate. The mixture was filtered and subjected to rotary evaporation. A crude product was separated by silica gel column chromatography (PE:EA=5:1) to obtain compound 14-d (2 g, 83%) as a white solid. LC-MS (ESI): m/z=233.9 [M+H]$^+$.

Synthesis of Compound 14-c 14-d (1 g, 4.27 mmol), trimethylsilylacetylene (0.46 g, 4.7 mmol), bis(triphenylphosphine) palladium dichloride (60 mg, 0.086 mmol), cuprous iodide (16 mg, 0.086 mmol) and triethylamine (15 mL) were added to a reaction flask. The reaction mixture was replaced with $N_2$ and reacted at 20° C. for 2 hours. After the reaction was completed, the reaction mixture was concentrated to remove organic solvents, added with water (30 mL), and extracted with ethyl acetate (30 mL). The organic phase was washed successively with water and a saturated aqueous sodium chloride solution, and dried over anhydrous sodium sulfate. The mixture was filtered and subjected to rotary evaporation. A crude product was purified by column chromatography (PE:EA=10:1) to obtain compound 14-c (0.7 g, 65%) as a yellow solid. LC-MS (ESI): m/z=252.3 [M+H]$^+$.

Synthesis of Compound 14-b 14-c (300 mg, 1.19 mmol), 2-bromo-6-trifluoromethylpyridine (226 mg, 1.3 mmol), bis(triphenylphosphine) palladium dichloride (17 mg, 0.024 mmol), cuprous iodide (4.5 mg, 0.024 mmol) and triethylamine (15 mL) were added to a reaction flask. The mixture was replaced with $N_2$, and a solution of tetrabutylammonium fluoride in tetrahydrofuran (1M, 2.4 mL, 2.4 mmol) was added dropwise. The reaction mixture was reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (PE:EA=2:1) to obtain compound 14-b (120 mg, 37%) as a yellow solid. LC-MS (ESI): m/z=271.0 [M+H]$^+$.

Synthesis of Compound 14-a

Compound 14-b (120 mg, 0.44 mmol), potassium carbonate (9 mg, 0.067 mmol), and dimethyl sulfoxide (2 mL) were added to a reaction flask. Under an ice bath, $H_2O_2$ (60 mg, 1.78 mmol) was added dropwise. After the addition was completed, the mixture was stirred overnight at room temperature. The next day, the mixture was filtered, and the filter cake was washed with water and dried to obtain compound 14-a (100 mg, 78%) as a white solid. LC-MS (ESI): m/z=289.0 [M+H]$^+$.

Synthesis of Compound 14

Pd—$CaCO_3$ (20 mg) was added to a solution of compound 14-a (50 mg, 0.17 mmol) in pyridine (10 mL) at room temperature. The reaction solution was evacuated and replaced with $H_2$ several times. The mixture was stirred overnight at room temperature, filtered and concentrated. A crude product was purified by Prep-HPLC to obtain compound 14 (10 mg, 20%) as a white solid. LC-MS (ESI): m/z=291.0 [M+H]$^+$; $^1$H NMR (500 MHz, MeOD): δ 9.45 (s, 1H), 8.09 (s, 1H), 8.00 (d, J=8.5 Hz, 1H), 7.75 (dd, J=8.5 1.5 Hz, 1H), 7.52 (t, J=7.5 Hz, 1H), 7.16 (d, J=7.5 Hz, 1H), 7.11 (d, J=12.5 Hz, 1H), 7.05 (d, J=7.5 Hz, 1H), 6.91 (d, J=12.5 Hz, 1H), 2.49 (s, 3H). Wherein 7.11 (d, J=12.5 Hz, 1H), 6.91 (d, J=12.5 Hz, 1H) is the compound displacement and coupling constant of the hydrogen on the carbon-carbon double bond.

Synthetic Route of Compound 15

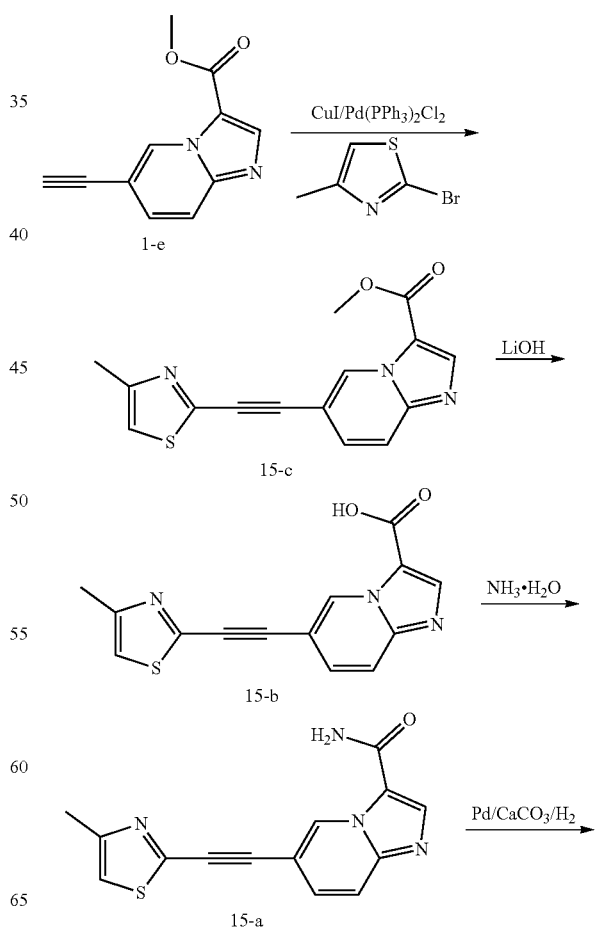

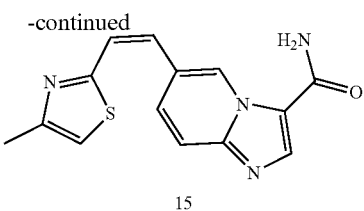

Synthetic Route of Compound 16

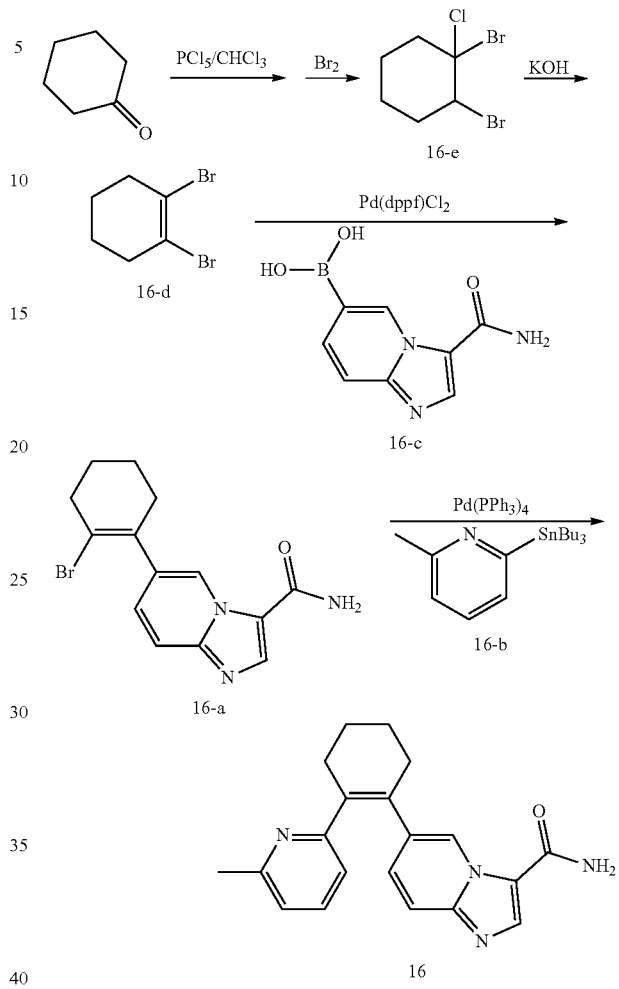

Synthesis of Compound 15-c 1-e (200 mg, 1 mmol), 2-bromo-4-methylthiazole (196 mg, 1.1 mmol), his(triphenylphosphine) palladium dichloride (70 mg, 0.1 mmol), and cuprous iodide (57 mg, 0.3 mmol) and triethylamine (15 mL) were added to a reaction flask. The reaction mixture was replaced with $N_2$ and reacted at 20° C. for 2 hours. After the reaction was completed, the reaction mixture was concentrated to remove organic solvents, added with water (30 mL), and extracted with ethyl acetate (30 mL×2). The organic phase was washed successively with water and a saturated aqueous sodium chloride solution, and dried over anhydrous sodium sulfate. The mixture was filtered and subjected to rotary evaporation. A crude product was purified by column chromatography (PE:EA=2:1) to obtain compound 15-c (150 mg, 51%) as a yellow solid. LC-MS (ESI): m/z=298.0 [M+H]$^+$.

Synthesis of Compound 15-b

Compound 15-c (150 mg, 0.5 mmol), tetrahydrofuran (6 mL), methanol (6 mL), water (3 mL) and lithium hydroxide monohydrate (84.7 mg, 2 mmol) were added to a reaction flask. After the mixture was stirred overnight at room temperature, it was added with dilute hydrochloric acid to adjust the pH to 6 to 7, and extracted with ethyl acetate (30 mL×3). The organic phase was washed successively with water and a saturated aqueous sodium chloride solution, and dried over anhydrous sodium sulfate. The mixture was filtered and subjected to rotary evaporation to obtain a crude compound 15-b (100 mg, 70%), LC-MS (ESI): m/z=283.9 [M+H]$^+$.

Synthesis of Compound 15-a

Oxalyl chloride (1 mL) was slowly added to a solution of compound 15-b (100 mg, 0.35 mmol) in dichloromethane (10 mL) under an ice bath, and then another drop of DMF was added. The mixture was stirred at room temperature for 1 hour, and concentrated to obtain a crude. The above crude product in dichloromethane (10 mL) was added slowly to aqueous ammonia (5 mL) under an ice bath. The mixture was stirred overnight at room temperature and concentrated. The crude product was purified by Prep-TLC (DCM:MeOH=10:1) to obtain compound 15-a (35 mg, 35%) as a white solid, LC-MS (ESI): m/z=283.1 [M+H]$^+$.

Synthesis of Compound 15

Pd—$CaCO_3$ (20 mg) was added to a solution of compound 15-a (35 mg, 0.124 mmol) in pyridine (10 mL) at room temperature. The reaction solution was evacuated and replaced with $H_2$ several times. The mixture was stirred overnight at room temperature, filtered and concentrated. A crude product was purified by Prep-HPLC to obtain compound 15 (20 mg, 56%) as a white solid. LC-MS (ESI): m/z=285.0 [M+H]$^+$; $^1$H NMR (500 MHz, MeOD): δ 9.83 (s, 1H), 8.29 (s, 1H), 7.69 (d, J=9.5 Hz, 1H), 7.56 (dd, J=9.5, 1.5 Hz, 1H), 7.03 (s, 1H), 6.90-6.98 (m, 2H), 2.40 (s, 3H). Wherein 6.90-6.98 (m, 2H) is the displacement of the hydrogen compound on the carbon-carbon double bond.

Synthesis of Compound 16-e

A solution of cyclohexanone (5.88 g, 60 mmol) in chloroform (30 mL) was slowly added dr op wise to a solution of phosphorus pentachloride (13.11 g, 63 mmol) in chloroform (30 mL) under an ice bath. The mixture was slowly heated to room temperature, reacted for 2 hours and then reacted under reflux for 2 hours, then poured into 150 g of ice, and slowly neutralized with solid sodium bicarbonate. After the ice was melted, the organic phase was separated, washed with saturated aqueous sodium bicarbonate solution, and dried over anhydrous sodium sulfate. The mixture was filtered, concentrated, then dissolved in dichloromethane (6 mL), and added dropwise slowly at −5° C. with liquid bromine (6.24 g, 39 mmol). The mixture was stirred at −5° C. for 5 minutes, washed with 10% aqueous sodium thiosulfate solution, and dried over anhydrous sodium sulfate. The mixture was concentrated. A crude was purified by silica gel column chromatography (petroleum ether as eluent) to obtain compound 16-e (10.1 g, 61%) as a white solid.

Synthesis of Compound 16-d

A solution of compound 16-e (10.1 g, 36.5 mmol) in methanol (40 mL) was slowly added to a solution of potassium hydroxide (4.1 g, 73.1 mmol) in methanol (40 mL) under reflux. The mixture was reacted under reflux for 3 hours, then cooled to room temperature, and neutralized with 6 M hydrochloric acid solution. The organic phase was separated, and the aqueous phase was extracted with ethyl acetate (40 mL×3). The organic phases were combined, and dried over anhydrous sodium sulfate. The mixture was concentrated. A crude was purified by silica gel column chromatography (petroleum ether as eluent) to obtain compound 16-d (0.68 g, 7.7%) as a white solid. $^1$H NMR (500 MHz, CDCl$_3$): δ 2.61-2.51 (m, 4H), 1.80-1.70 (m, 4H).

Synthesis of Compound 16-c
Synthesis of Reference Compound 4-a.
Synthesis of Compound 16-a 16-d (0.57 g, 2.38 mmol), 16-c (0.44 g, 2.14 mmol), Pd(dppf)Cl$_2$ (174 mg, 0.238 mmol), sodium carbonate (504 mg, 4.76 mmol) 1,4-dioxane (20 mL) and water (4 mL) were added to a reaction flask. The reaction mixture was replaced with N$_2$ and reacted overnight at 90° C. After the reaction was completed, the mixture was concentrated to remove organic solvents. A crude product was purified by column chromatography (DCM:MeOH=30:1) to obtain compound 16-a (420 mg, 55%) as a yellow solid. LC-MS (ESI): m/z=320.1 [M+H]$^+$.

Synthesis of Compound 16-b

It was prepared according to the method in the literature (Organometallics, 2017, vol. 36, #8, 1541-1549).

Synthesis of Compound 16

16-a (0.38 g, 1.19 mmol), 16-b (2.27 g, 5.94 mmol), Pd(PPh$_3$)$_4$ (137 mg, 0.119 mmol) and toluene (20 mL) were added to a reaction flask. The reaction mixture was replaced with N$_2$ and reacted overnight at 90° C. After the reaction was completed, the mixture was concentrated to remove organic solvents. A crude product was purified by column chromatography (DCM:MeOH=20:1) and Prep-HPLC to obtain compound 16 (40 mg, 10%) as a yellow solid. LC-MS (ESI): m/z=333.3 [M+H]$^+$; $^1$H NMR (500 MHz, MeOD): δ 9.19 (s, 1H), 8.17 (s, 1H), 7.35-7.47 (m, 2H), 7.22 (dd, J=9.5, 2.0 Hz, 1H), 6.99 (d, J=7.5 Hz, 1H), 6.80 (d, J=8.0 Hz, 1H), 2.58 (m, 4H), 2.48 (s, 3H), 1.94 (m, 4H).

Synthetic Route of Compound 17a

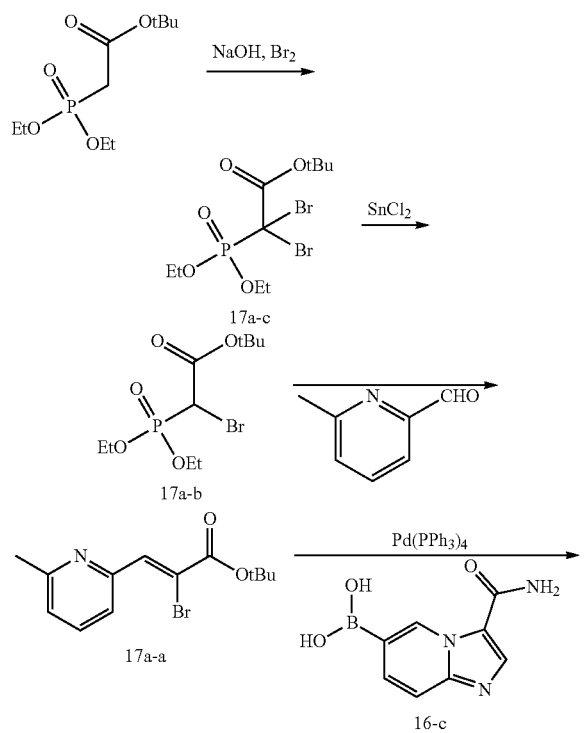

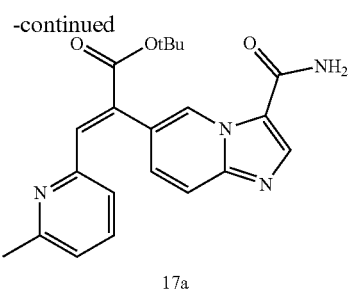

17a

Synthesis of Compound 17a-c

Under an ice bath, bromine (12.8 mL, 0.25 mol) was added slowly to a solution of sodium hydroxide (20 g, 0.5 mol) in water (60 mL). The reaction solution was stirred at 0° C. for 25 minutes, and then tert-butyl diethylphosphonoacetate (12.6 mL, 53.65 mmol) was added dropwise. After the dropwise addition, the reaction solution was extracted with dichloromethane (70 mL×2). The organic phase was washed with water (50 mL×1), and dried over anhydrous sodium sulfate. The mixture was filtered and subjected to rotary evaporation to obtain product 17a-c (20 g, 91%) as colorless oil. $^1$H NMR (500 MHz, CDCl$_3$): δ 4.35-4.41 (m, 4H), 1.54 (s, 9H), 1.39 (t, J=6.5 Hz, 6H).

Synthesis of Compound 17a-b

A solution of stannous chloride dihydrate (5.39 mL, 23.90 mmol) in water (50 mL) was added dropwise slowly to a solution of 17a-c (10 g, 24.39 mmol) in tert-butanol (50 mL) under an ice bath. The white reaction solution was kept at 0° C. and stirred for 15 minutes, and extracted with dichloromethane (50 mL×3). The organic phase was washed with water (50 mL×2), and dried over anhydrous sodium sulfate. The mixture was filtered and subjected to rotary evaporation to obtain product 17a-b (7 g, 87%) as yellowish oil. $^1$H NMR (500 MHz, CDCl$_3$): δ 4.25-4.30 (m, 5H), 1.50 (s, 9H), 1.38 (t, J=7.5 Hz, 6H).

Synthesis of Compound 17a-a

A solution of 17a-b (4.10 g, 12.38 mmol) in tetrahydrofuran (50 mL) was cooled to −78° C. under nitrogen protection, and LiHMDS (1M in THF, 12.38 mL, 12.38 mmol) was slowly added dropwise over 10 minutes, followed by the addition of 6-methyl-2-pyridinecarboxaldehyde (1 g, 8.25 mmol). After the addition was completed, the reaction solution was stirred at a low temperature for 30 minutes and then heated to room temperature for 1.5 hours. The reaction was quenched with water (20 mL), and extracted with ethyl acetate (50 mL×3). The combined organic phase was washed with water (50 mL×1), and dried over anhydrous sodium sulfate. The mixture was filtered and subjected to rotary evaporation. A crude product was purified by silica gel column chromatography (PE:EA=5:1) to obtain 17a-a (2 g, 81%) as colorless oil. LC-MS (ESI): m/z=242.1 [M+H-tBu]+.

Synthesis of Compound 17a

A mixture of compounds 17a-a (2 g, 6.71 mmol), 16-c (10.06 g, 2.06 mmol), Pd(PPh$_3$)$_4$ (0.78 g, 0.67 mmol), sodium carbonate (1.42 g, 13.4 mmol), toluene (10 mL), ethanol (5 mL) and water (5 mL) was heated to 80° C. and reacted overnight under a nitrogen atmosphere. The reactants were cooled to room temperature and concentrated, and separated with a mixture of water (10 mL) and dichloromethane (30 mL). The aqueous phase was extracted with dichloromethane, and the combined organic layer was washed with water, washed with saturated brine, dried, filtered and concentrated. The mixture was subjected to primary separation by silica gel column chromatography (DCM:MeOH=20:1) to obtain a crude. The crude was added with ethyl acetate (10 mL) and heated to reflux and stirred for 30 minutes. After cooling, it was filtered. A small amount of mother liquor was concentrated and separated by high-performance liquid preparation to obtain 17a as a white solid. LC-MS (ESI): m/z=379.2 [M+H]⁺; ¹H NMR (500 MHz, MeOD) δ: 9.79 (s, 1H), 8.32 (s, 1H), 7.84 (dd, J=9.5, 2 Hz, 1H), 7.76 (d, j=9.5 Hz, 1H), 7.73 (t, j=7.5 Hz, 1H), 7.34 (d, j=8 Hz, 1H), 7.22 (d, j=8 Hz, 1H), 7.18 (s, 1H), 2.57 (s, 3H), 1.60 (s, 9H).

Synthetic Route of Compound 17b

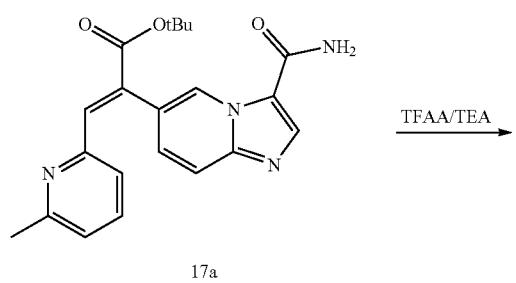

Synthesis of Compound 17b

Under an ice bath, triethylamine (1.1 mL, 7.93 mmol) and trifluoroacetic anhydride (1.1 mL, 7.93 mmol) were added to a solution of 17a (1.5 g, 3.97 mmol) in tetrahydrofuran (10 mL). After the addition was completed, the mixture was heated to room temperature and stirred for 2 hours. After the reaction was completed, the mixture was added with ice water (10 mL), and extracted with ethyl acetate. The combined organic phase was washed with saturated brine, dried over anhydrous sodium sulfate, and concentrated to obtain a light yellow solid 17b (1 g, 70%). LC-MS (ESI): m/z=361.3 [M+H]⁺.

Synthetic Route of Compound 17c

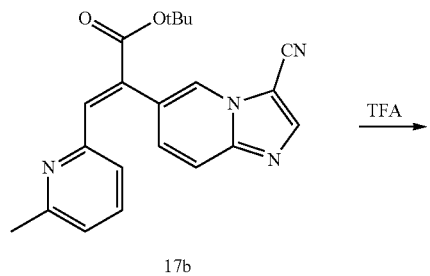

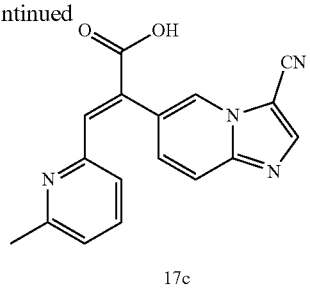

Synthesis of Compound 17c

Trifluoroacetic acid (4 mL) was added to a solution of 17b (1 g, 2.77 mmol) in methylene chloride (20 mL). The resulting reaction solution was stirred at room temperature overnight. After the reaction was completed, the reaction solution was concentrated, carefully neutralized to a pH of about 6 to 7 with a saturated solution of sodium bicarbonate under an ice bath, stirred for half an hour and filtered. The filter cake was washed with water and dried to obtain compound 17c (0.6 g, 71%) as a yellowish solid. LC-MS (ESI): m/z=305.0 [M+H]⁺; ¹H NMR (500 MHz, DMSO-t/d): δ 13.16 (s, 1H), 9.60 (s, 1H), 8.48 (s, 1H), 7.89 (s, 1H), 7.79 (d, J=8.5 Hz, 1H), 7.59 (t, J=5 Hz, 1H), 7.38 (d, J=7.5 Hz, 1H), 7.12-7.16 (m, 2H), 2.17 (s, 3H).

Synthetic Route of Compound 18a

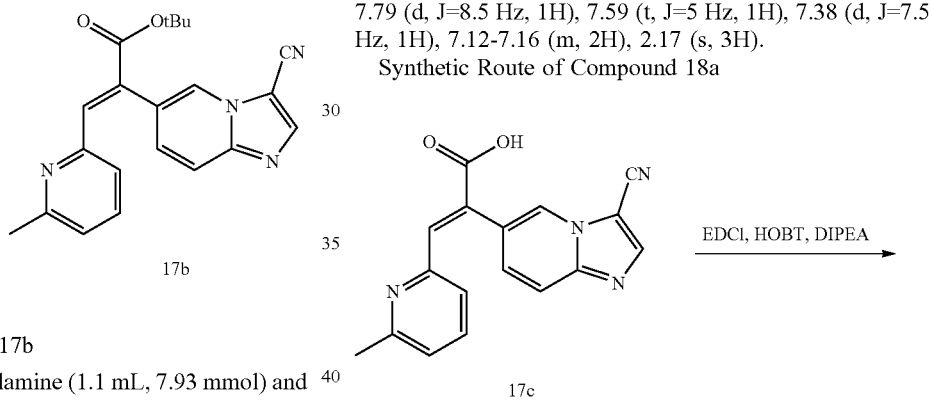

Synthesis of Compound 18a

EDCI (75.6 mg, 0.39 mmol), HOBt (57.7 mg, 0.43 mmol) and DIPEA (127.4 mg, 0.99 mmol) were added to a solution of 17c (100 mg, 0.33 mmol) and ammonium chloride (1.3 g, 0.66 mmol) in DMF (5 mL). The resulting reaction solution was stirred at room temperature overnight. After the reaction was completed, the reaction solution was diluted with water and separated, and the aqueous phase was extracted with dichloromethane. The combined organic phase was washed with saturated brine and dried over anhydrous Na₂SO₄. The mixture was concentrated. A crude product was purified by Prep-TLC (DCM:MeOH=20:1) to obtain compound 18a (60 mg, 60%) as a white solid. LC-MS (ESI): m/z=304.0 [M+H]⁺.

Synthetic Route of Compound 18

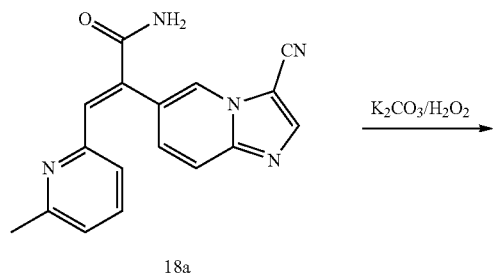

18a

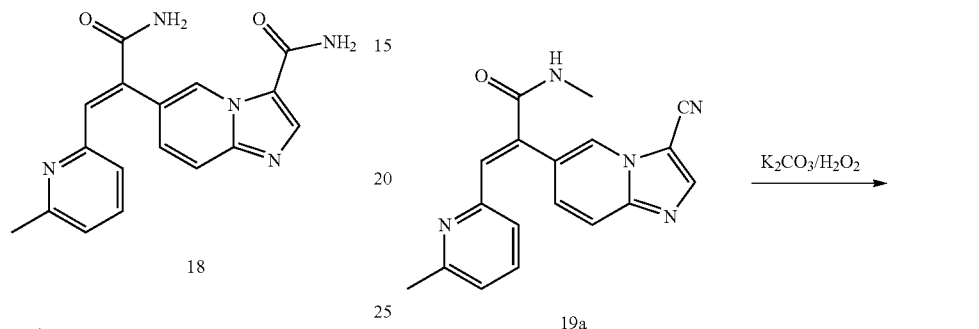

18

Synthesis of Compound 18

Compound 18a (60 mg, 0.2 mmol), potassium carbonate (4 mg, 0.03 mmol), and dimethyl sulfoxide (2 mL) were added to a reaction flask. Under an ice bath, $H_2O_2$ (26.9 mg, 0.79 mmol) was added dropwise. After the addition was completed, the mixture was stirred overnight at room temperature. The next day, the mixture was filtered, and the filter cake was washed with water and dried to obtain compound 18 (35 mg, 55%) as a white solid. LC-MS (ESI): m/z=322.0 [M+H]$^+$; $^1$H NMR (500 MHz, MeOD): δ 9.45 (s, 1H), 8.30 (s, 1H), 7.75 (s, 1H), 7.71 (d, J=9 Hz, 1H), 7.50 (t, J=8 Hz, 1H), 7.35 (dd, J=9.0, 1.5 Hz, 1H), 7.11 (d, J=7.5 Hz, 1H), 6.94 (d, J=8 Hz, 1H), 2.37 (s, 3H).

Synthetic Route of Compound 19a

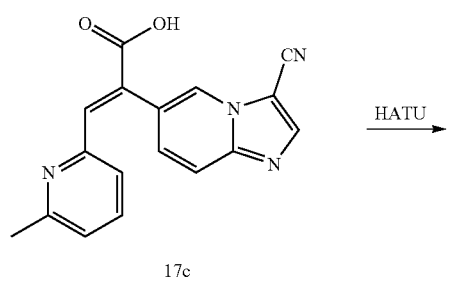

17c

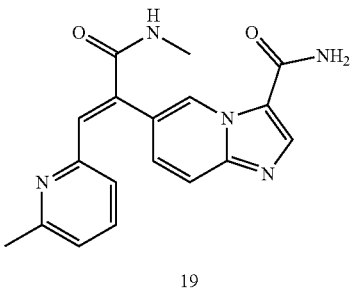

19a

Synthesis of Compound 19a

HATU (125 mg, 0.33 mmol) and DIPEA (64 mg, 0.49 mmol) were added to a solution of 17c (50 mg, 0.16 mmol) and methylamine tetrahydrofuran solution (2M, 0.33 mL, 0.66 mmol) in dichloromethane (10 mL). The resulting reaction solution was stirred at room temperature overnight. After the reaction was completed, the reaction solution was diluted with water and separated, and the aqueous phase was extracted with dichloromethane. The combined organic phase was washed with saturated brine and dried over anhydrous $Na_2SO_4$, and concentrated. A crude product was purified by Prep-TLC (DCM:Methanol=20:1) to obtain the product 19a (30 mg, 58%) as a white solid. LC-MS (ESI): m/z=318.2 [M+H]$^+$.

Synthetic Route of Compound 19

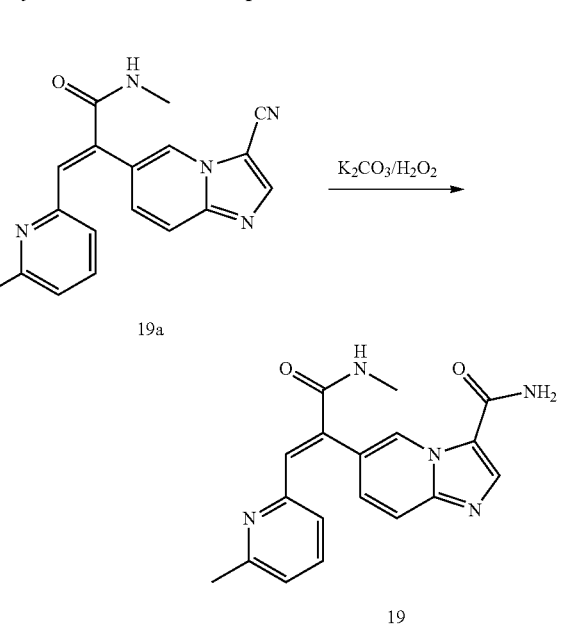

19a

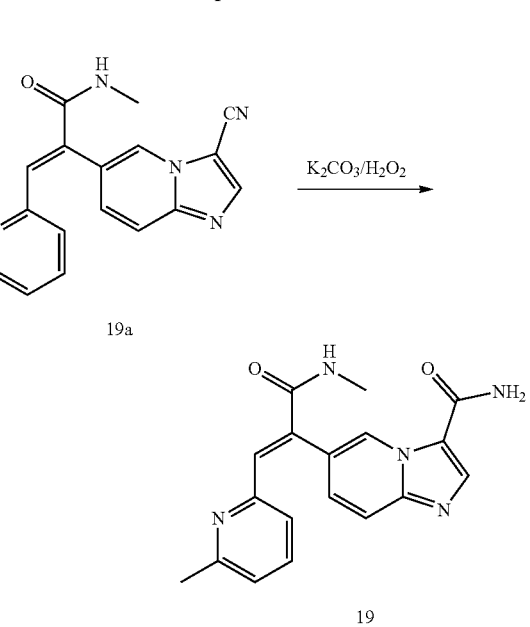

19

Synthesis of Compound 19

Compound 19a (30 mg, 0.095 mmol), potassium carbonate (2 mg, 0.014 mmol), and dimethyl sulfoxide (2 mL) were added to a reaction flask. Under an ice bath, $H_2O_2$ (12.9 mg, 0.38 mmol) was added dropwise. After the addition was completed, the mixture was stirred overnight at room temperature. The next day, the mixture was filtered, and the filter cake was washed with water and dried to obtain compound 19 (10 mg, 32%) as a white solid. LC-MS (ESI): m/z=336.3 [M+H]$^+$; $^1$H NMR (500 MHz, DMSO-tifc): δ 9.31 (s, 1H), 8.35 (s, 1H), 7.95 (bs, 1H), 7.73-7.78 (m, 1H), 7.68 (d, J=9 Hz, 1H), 7.57 (s, 1H), 7.49 (t, J=8.5 Hz, 1H), 7.35 (bs, 1H), 7.18 (dd, J=9.5, 2 Hz, 1H), 7.05 (d, J=7.5 Hz, 1H), 6.88 (d, J=7.5 Hz, 1H), 2.67 (d, J=4 Hz, 3H), 2.22 (s, 3H).

Synthetic Route of Compound 20a

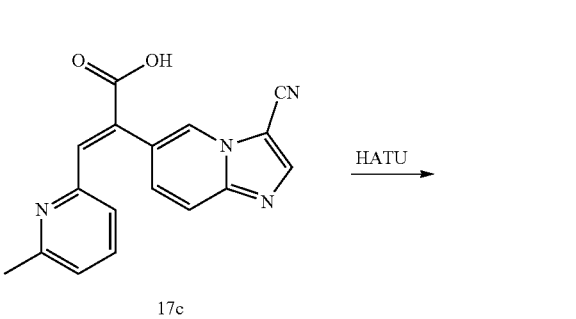

17c

-continued

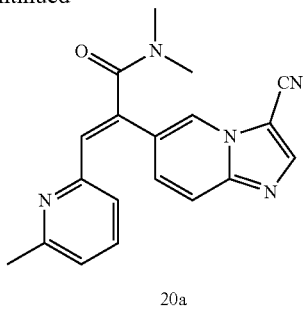

20a

Synthesis of Compound 20a

HATU (125 mg, 0.33 mmol) and DIPEA (212 mg, 1.6 mmol) were added to a solution of 17c (50 mg, 0.16 mmol) and dimethylamine hydrochloride (329 mg, 0.66 mmol) in dichloromethane (10 mL). The resulting reaction solution was stirred at room temperature overnight. After the reaction was completed, the reaction solution was diluted with water and separated, and the aqueous phase was extracted with dichloromethane. The combined organic phase was washed with saturated brine, dried over anhydrous $Na_2SO_4$, concentrated, and purified by Prep-TLC (DCM:Methanol=20:1) to obtain compound 20a (40 mg, 73%) as a white solid. LC-MS (ESI): m/z=332.2 $[M+H]^+$.

Synthetic Route of Compound 20

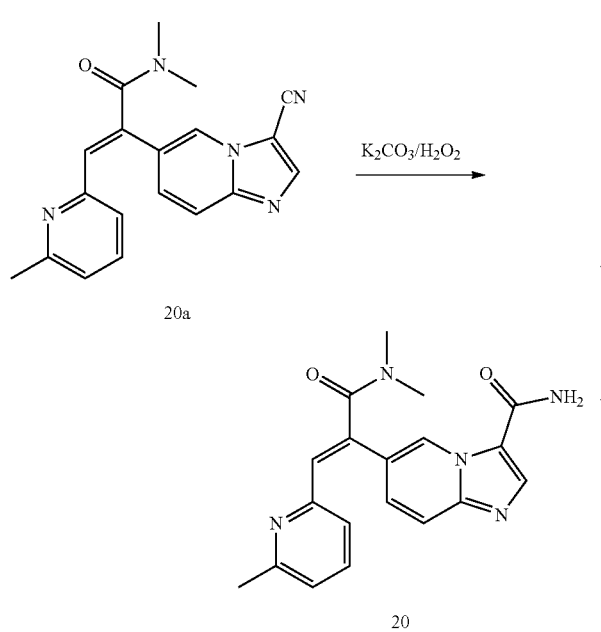

Synthesis of Compound 20

Compound 20a (40 mg, 0.12 mmol), potassium carbonate (2.5 mg, 0.018 mmol), and dimethyl sulfoxide (2 mL) were added to a reaction flask. Under an ice bath, $H_2O_2$ (16.4 mg, 0.48 mmol) was added dropwise. After the addition was completed, the mixture was stirred overnight at room temperature. The next day, the mixture was filtered, and the filter cake was washed with water and dried to obtain 20 (25 mg, 59%) as a white solid. LC-MS (ESI): m/z=350.0 $[M+H]^+$; $^1H$ NMR (400 MHz, DMSO-$d_6$): δ 9.56 (s, 1H), 8.33 (s, 1H), 7.94 (bs, 1H), 7.62 (dd, J=9.2, 0.8 Hz, 1H), 7.53 (t, J=7.6 Hz, 1H), 7.35 (bs, 1H), 7.26 (dd, J=9.2, 1.6 Hz, 1H), 7.08 (d, J=7.6 Hz, 1H), 6.98 (d, J=7.6 Hz, 1H), 6.78 (s, 1H), 3.08 (s, 3H), 2.94 (s, 3H), 2.29 (s, 3H).

Synthetic Route of Compound 21a

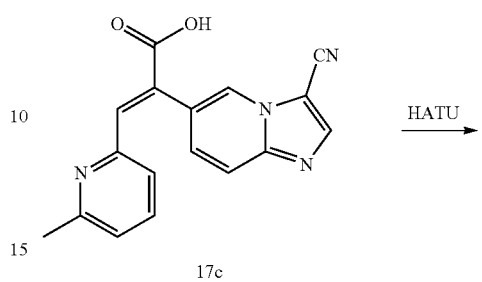

17c

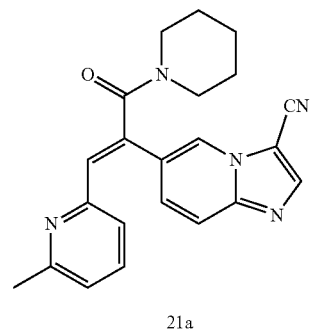

21a

Synthesis of Compound 21a

HATU (125 mg, 0.33 mmol) and DIPEA (64 mg, 0.49 mmol) were added to a solution of 17c (50 mg, 0.16 mmol) and piperidine (56 mg, 0.66 mmol) in methylene chloride (10 mL). The resulting reaction solution was stirred at room temperature overnight. After the reaction was completed, the reaction solution was diluted with water and separated, and the aqueous phase was extracted with dichloromethane. The combined organic phase was washed with saturated brine and dried over anhydrous $Na_2SO_4$, and concentrated. A crude product was purified by Prep-TLC (DCM:Methanol=20:1) to obtain compound 21a (50 mg, 82%) as a white solid. LC-MS (ESI): m/z=372.1 $[M+H]^+$.

Synthetic Route of Compound 21

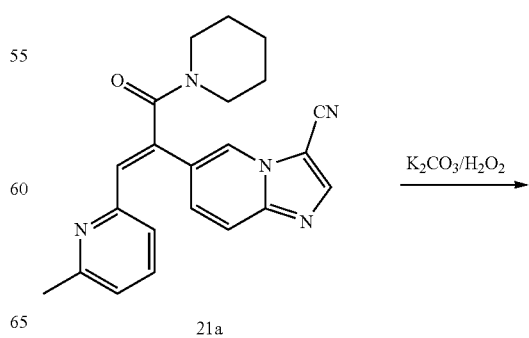

21a

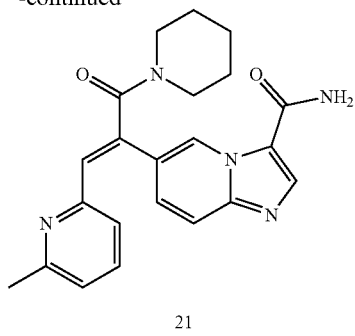

21

Synthesis of Compound 21

Compound 21a (50 mg, 0.13 mmol), potassium carbonate (2.8 mg, 0.02 mmol), and dimethyl sulfoxide (2 mL) were added to a reaction flask. Under an ice bath, $H_2O_2$ (18.3 mg, 0.54 mmol) was added dropwise. After the addition was completed, the mixture was stirred overnight at room temperature. The next day, the mixture was filtered, and the filter cake was washed with water and dried to obtain compound 21 (30 mg, 57%) as a white solid. LC-MS (ESI): m/z=390.2 [M+H]$^+$; $^1$H NMR (500 MHz, MeOD): δ 9.61 (s, 1H), 8.28 (s, 1H), 7.60 (d, J=9.5 Hz, 1H), 7.55 (t, J=7.5 Hz, 1H), 7.34 (dd, J=10, 2 Hz, 1H), 7.16 (d, j=8 Hz, 1H), 7.04 (d, j=8 Hz, 1H), 6.89 (s, 1H), 3.70 (m, 4H), 2.46 (s, 3H), 1.55-1.72 (m, 6H).

Synthetic Route of Compound 22

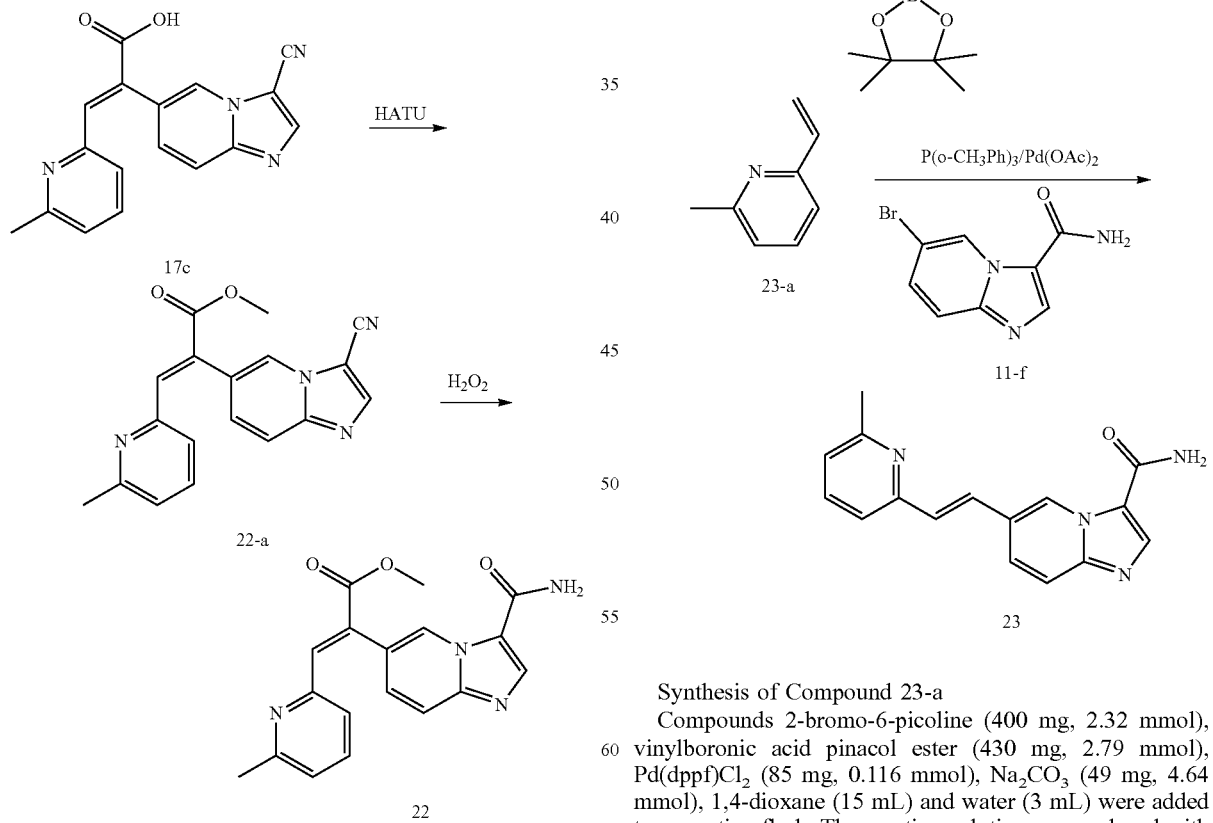

Synthesis of Compound 22-a

HATU (949 mg, 1.97 mmol) and DIPEA (637.1 mg, 4.93 mmol) were added to a solution of 17c (300 mg, 0.99 mmol) and methanol (1.97 g, 3.94 mmol) in methylene chloride (10 mL). The resulting reaction solution was stirred at room temperature overnight. After the reaction was completed, the reaction solution was diluted with water and separated, and the aqueous phase was extracted with dichloromethane. The combined organic phase was washed with saturated brine and dried over anhydrous $Na_2SO_4$, and concentrated. A crude product was purified by Prep-TLC (PE:EA=1:1) to obtain compound 22-a (250 mg, 80%) as a white solid. LC-MS (ESI): m/z=319.0 [M+H]$^+$.

Synthesis of Compound 22

Compound 22-a (80 mg, 0.25 mmol), potassium carbonate (5 mg, 0.038 mmol), and dimethyl sulfoxide (2 mL) were added to a reaction flask. Under an ice bath, $H_2O_2$ (34.2 mg, 1.0 mmol) was added dropwise. After the addition was completed, the mixture was stirred overnight at room temperature. The next day, the mixture was filtered, and the filter cake was washed with water and dried to obtain a white solid 22 (40 mg, 47%). LC-MS (ESI): m/z=337.2 [M+H]$^+$; $^1$H NMR (500 MHz, MeOD): δ: 9.40 (s, 1H), 8.30 (s, 1H), 8.02 (s, 1H), 7.67 (d, J=9 Hz, 1H), 7.51 (t, J=8 Hz, 1H), 7.37 (dd, J=9, 1.5 Hz, 1H), 7.13 (d, J=8.5 Hz, 1H), 6.97 (d, J=8 Hz, 1H), 3.88 (s, 3H), 2.37 (s, 3H).

Synthetic Route of Comparative Compound 23

Synthesis of Compound 23-a

Compounds 2-bromo-6-picoline (400 mg, 2.32 mmol), vinylboronic acid pinacol ester (430 mg, 2.79 mmol), Pd(dppf)Cl$_2$ (85 mg, 0.116 mmol), Na$_2$CO$_3$ (49 mg, 4.64 mmol), 1,4-dioxane (15 mL) and water (3 mL) were added to a reaction flask. The reaction solution was replaced with N$_2$, stirred overnight at 90° C., added with water (30 mL), and extracted with ethyl acetate (50 mL). The organic phase was dried over anhydrous sodium sulfate, filtered and concentrated. A crude product was purified by silica gel column chromatography (PE:EA=10:1) to obtain compound 23-a (160 mg, 58%) as red oil. LC-MS (ESI): m/z=120.2[M+H]+.

Synthesis of Comparative Compound 23

Compounds 23-a (160 mg, 1.3 mmol), 11-f (387 mg, 1.6 mmol), tri(o-tolyl)phosphine (79 mg, 0.26 mmol), palladium acetate (29 mg, 0.13 mmol), tri ethyl amine (0.362 mL, 2.6 mmol) and DMF (10 mL) were added to a reaction flask. The reaction solution was replaced with $N_2$, stirred overnight at 90° C., added with water (50 mL), and extracted with ethyl acetate (30 mL×2). The organic phase was dried over anhydrous sodium sulfate, filtered, and concentrated. A crude product was purified by Prep-HPLC to obtain compound 23 (45 mg, 12%) as a white solid. LC-MS (ESI): m/z=279.1 [M+H]+; $^1$H NMR (500 MHz, CDCl$_3$): δ 9.63 (s, 1H), 8.05 (s, 1H), 7.75 (dd, 7=9.5, 1.5 Hz, 1H), 7.70 (d, J=9.5 Hz, 1H), 7.64 (d, J=16.5 Hz, 1H), 7.58 (t, J=7.5 Hz, 1H), 7.24 (d, J=8.0 Hz, 1H), 7.20 (d, J=16.0 Hz, 1H), 7.06 (d, J=8.0 Hz, 1H), 5.67 (brs, 1H), 2.60 (s, 3H). Wherein 7.64 (d, J=16.5 Hz, 1H), 7.20 (d, J=16.0 Hz, 1H) is the compound displacement and coupling constant of the hydrogen on the carbon-carbon double bond.

Synthetic Route of Comparative Compound 24

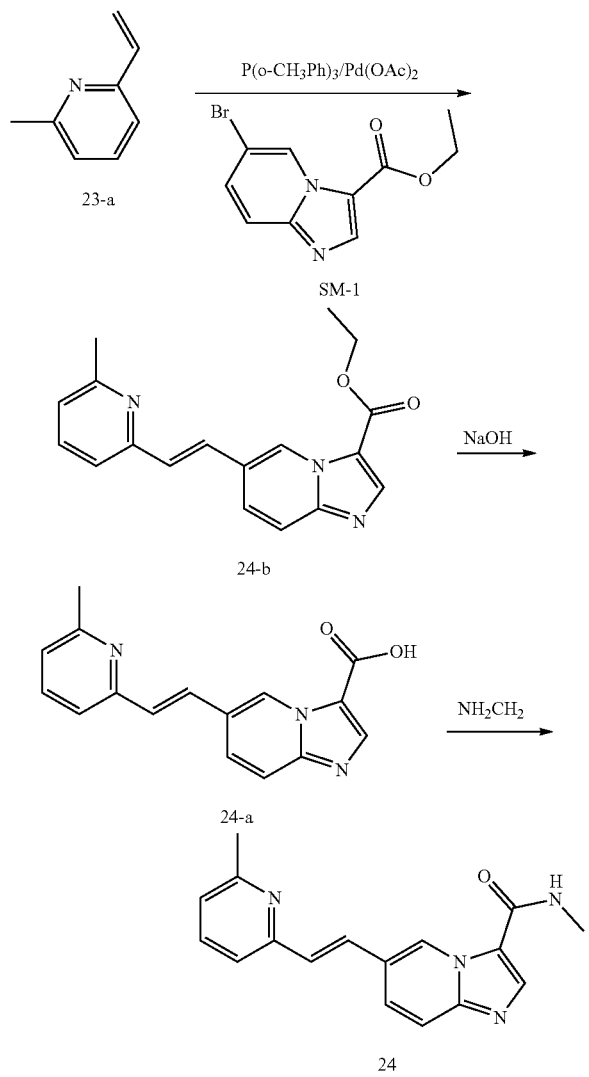

Synthesis of Compound 24-b

Compounds 23-a (300 mg, 2.52 mmol), SM-1 (677 mg, 2.52 mmol), tri(o-tolyl)phosphine (153 mg, 0.5 mmol), palladium acetate (56 mg, 0.25 mmol), triethylamine (0.7 mL, 5 mmol) and DMF (10 mL) were added to a reaction flask. The reaction solution was replaced with $N_2$, stirred overnight at 90° C., added with water (50 mL), and extracted with ethyl acetate (30 mL×2). The organic phase was dried over anhydrous sodium sulfate, filtered, and concentrated. A crude product was purified by silica gel column chromatography to obtain compound 24-b (500 mg, 65%) as a white solid. LC-MS (ESI): m/z=308.0 [M+H]+.

Synthesis of Compound 24-a 24-b (0.5 g, 1.63 mmol) was added to methanol (10 mL) and THF (10 mL), and a sodium hydroxide aqueous solution (4M, 2 mL) was added. The reaction solution was stirred overnight at room temperature. After the reaction was completed, the mixture was concentrated under reduced pressure to remove organic solvents, water (10 mL) and DCM (50 mL) were added. The liquid was separated, and the organic layer was discarded. The water layer was cooled to 0° C. and neutralized with hydrochloric acid (2 M) to pH 6 to 7. A yellowish precipitate was filtered off and dried to obtain compound 24-a (0.4 g, 88%). LC-MS (ESI): m/z=280.3 [M+H]+; $^1$H NMR (400 MHz, MeOD): δ 9.76 (s, 1H), 8.07 (s, 1H), 7.85 (d, J=8.4 Hz, 1H), 7.71 (t, J=7.6 Hz, 1H), 7.61-7.65 (m, 2H), 7.49 (d, J=8 Hz, 1H), 7.28 (d, 7=16.4 Hz, 1H), 7.17 (d, J=7.6 Hz, 1H), 2.57 (s, 3H).

Synthesis of Comparative Compound 24

24-a (100 mg, 0.36 mmol) was dissolved in dichloromethane (10 mL). Under an ice bath, oxalyl chloride (1 mL) and a drop of DMF were slowly added to the solution. The reactants were heated to room temperature and reacted for 60 minutes. The reactants were concentrated under reduced pressure and diluted with dichloromethane (5 mL). Under an ice bath, the solution was slowly added dr op wise to a solution of methylamine tetrahydrofuran (2M, 5 mL). The reaction mixture was reacted at 0° C. for 10 minutes, and then heated to room temperature and stirred overnight. The liquid was separated and the aqueous layer was extracted with dichloromethane. The organic phases were combined, washed with water and brine, dried over anhydrous sodium sulfate, and concentrated to obtain a crude. The crude was subjected to high performance liquid preparative chromatography to obtain a white solid 24 (10 mg, 10%). LC-MS (ESI): m/z=293.3 [M+H]+; $^1$H NMR (500 MHz, MeOD): δ 9.43 (s, 1H), 8.06 (s, 1H), 7.75 (dd, 7=9.5, 1.5 Hz, 1H), 7.59 (t, 7=7.5 Hz, 1H), 7.54 (d, 7=9.5 Hz, 1H), 7.44 (d, J=16.0 Hz, 1H), 7.34 (d, J=7.5 Hz, 1H), 7.11 (d, J=16.5 Hz, 1H), 7.06 (d, J=7.5 Hz, 1H), 4.90 (s, 3H), 2.91 (s, 3H). Wherein 7.44 (d, J=16.0 Hz, 1H), 7.11 (d, J=16.5 Hz, 1H) is the compound displacement and coupling constant of the hydrogen on the carbon-carbon double bond.

Effect Example 1 Evaluation Experiment of ALK5 Enzyme Activity Inhibition $IC_{50}$ 1. Preparation of a 1× kinase buffer: 40 mM Tris (pH 7.5), 20 mM MgCl2, 0.10% BSA, 1 mM DTT.

2. Compound preparation: The final detection concentration of the compound was 10 μM, which was prepared to a 100-fold concentration, i.e., 1 mM. 100 μL of the 100-fold compound was added in the second well of the 384-well plate, and 60 μL of 100% DMSO was added to the other wells. 30 μL of compound from the second well was added to the third well, which was made a 3-fold dilution in sequence, diluting a total of 10 concentrations. 50 nL of the compound was transferred to the reaction plate with echo.

3. Kinase reaction: The kinase was added to a 1× kinase buffer to form a 2× enzyme solution. The final concentration of the kinase solution was ALK5: 25 nM. The polypeptide TGFbR1 (purchased from Signal Chem, catalog number T36-58) and ATP were added to a 1× kinase buffer to form a 2× substrate solution. The final concentration of the substrate solution was peptide TGFbR1 0.1 mg/mL, ATP 7 μM. 2.5 μL of the 2× enzyme solution was added to the 384-well reaction plate (there was already 50 nL of 100% DMSO dissolved compound), and a 1× kinase buffer was added to a negative control well. The reaction solution was incubated at room temperature for 10 minutes. 2.5 μL of 2× substrate solution was added to the 384-well reaction plate. The 384-well plate was covered and incubated at 30° C. for 1 hour. ADP-Glo reagent (purchased from Promege, catalog number v9102) was equilibrated to room temperature. 5 μL of ADP-Glo reagent was transferred to the reaction well of the 384-well plate to stop the reaction.

4. Detection of reaction results: 10 μL of kinase detection reagent was transferred to each well, shaken for 1 minute, and let stand at room temperature for 30 minutes. The sample luminescence value was read at Synegy.

5. Curve fitting: The data of the luminescence reading were copied from the Synegy program. The value of the luminescence reading was converted to inhibition percentage by a formula (inhibition percentage=(max−sample RLU)/(max−min)×100, where "min" was a fluorescence reading for a control sample without enzyme; "max" was a fluorescence reading for a sample with DMSO as a control). The data were imported into MS Excel and GraphPad Prism was used for curve fitting. $IC_{50}$ value was calculated.

TABLE 1

$IC_{50}$ results of the compounds of the present invention on ALK5 activity

| Compound No. | ALK5 $IC_{50}$ (nM) | Compound No. | ALK5 $IC_{50}$ (nM) |
| --- | --- | --- | --- |
| 1 | 8 | 2 | 44 |
| 3 | 9.2 | 4 | 17 |
| 5 | 35 | 6 | 25 |
| 7 | 21 | 8 | 56 |
| 9 | 15 | 10 | 15 |
| 11 | 10 | 12 | 8.5 |
| 13 | 5.1 | 14 | 78 |
| 15 | 33 | 16 | 48 |
| 17 | 616 | 17a | 6.6 |
| 18 | 328 | 19 | 207 |
| 20 | 34 | 21a | 4946 |
| 21 | 58 | SB431542 | 108 |
| 22 | 7.4 | Comparative compound 23 | 372 |
| Comparative compound 24 | 88 | / | / | wherein SB431542 (CAS number: 301836-41-9) is a known ALK5 inhibitor, and its structure is as follows:

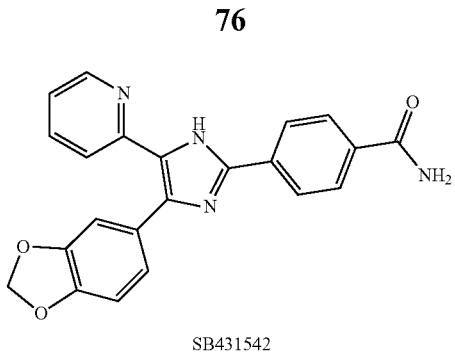

SB431542

From the results of the above tests, it can be confirmed that the compounds of the present invention have a significant inhibitory effect on ALK5 activity.

Although the specific embodiments of the present invention have been described above, it will be understood by those skilled in the art that these are merely illustrative, and that various alterations or modifications can be made to these embodiments without departing from the principle and essence of the present invention. Therefore, the scope of protection of the present invention is defined by the appended claims.

What is claimed is:

1. An aromatic heterocyclic substituted olefin compound represented by general formula I or a pharmaceutically acceptable salt thereof:

I wherein ring A and ring B are located on the same side of the double bond;

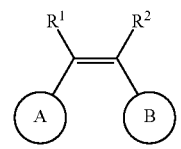 is

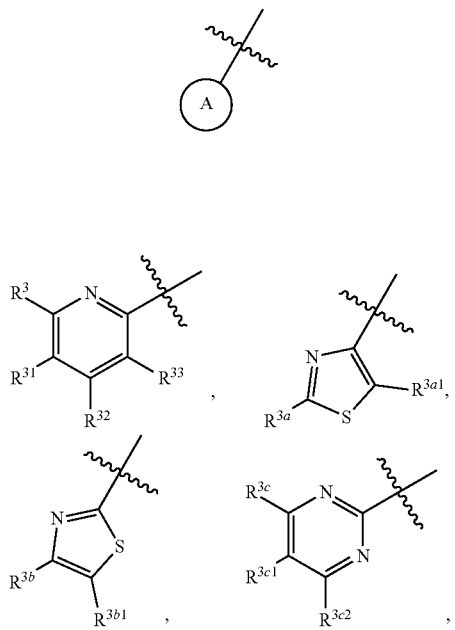

-continued

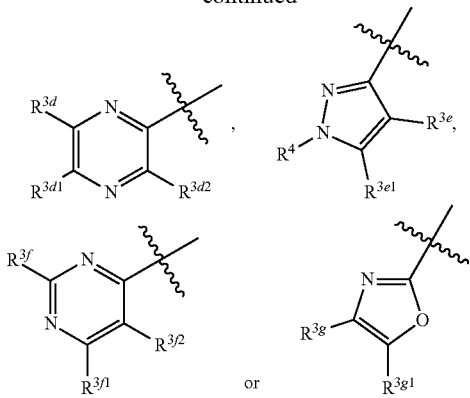

is

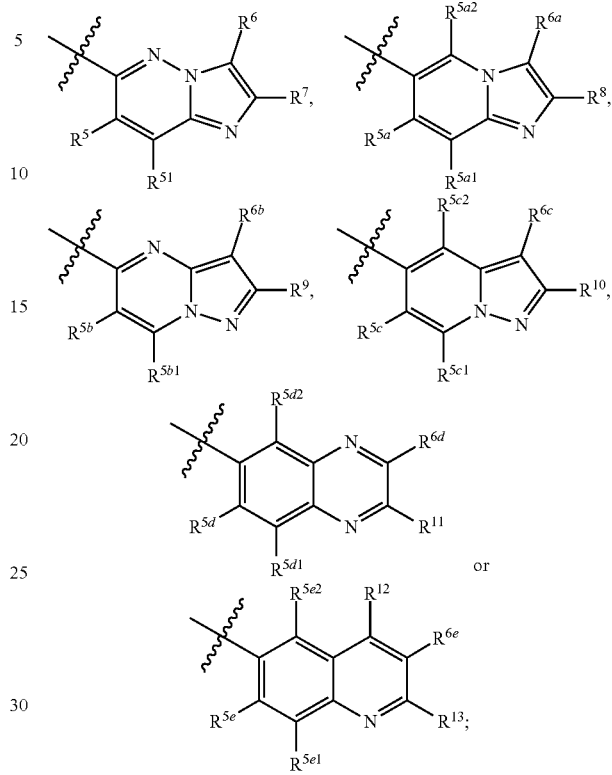

R³, R³¹, R³², R³³, R³ᵃ, R³ᵃ¹, R³ᵇ, R³ᵇ¹, R³ᶜ, R³ᶜ¹, R³ᶜ², R³ᵈ, R³ᵈ¹, R³ᵈ², R³ᵉ, R³ᵉ¹, R³ᶠ, R³ᶠ¹, R³ᶠ², R³ᵍ and R³ᵍ¹ are each independently hydrogen, halogen, cyano, nitro, —NRᵃ³Rᵃ⁴, —ORᵃ⁵, —SRᵃ⁶, —C(O)ORᵃ⁷, —C(O)NRᵃ⁸Rᵃ⁹, —CORᵃ¹⁰, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{4-8}$ cycloalkenyl, substituted or unsubstituted $C_{6-20}$ aryl, or substituted or unsubstituted $C_{2-10}$ heteroaryl; wherein Rᵃ³, Rᵃ⁴, Rᵃ⁵, Rᵃ⁶, Rᵃ⁷, Rᵃ⁸, Rᵃ⁹ and Rᵃ¹⁰ are each independently hydrogen, substituted or unsubstituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl; Rᵃ³ and Rᵃ⁸ can also be independently hydroxyl or $C_{1-6}$ alkoxy;

substituents in the substituted $C_{1-6}$ alkyl in R³, R³¹, R³², R³³, R³ᵃ, R³ᵃ¹, R³ᵇ, R³ᵇ¹, R³ᶜ, R³ᶜ¹, R³ᶜ², R³ᵈ, R³ᵈ¹, R³ᵈ², R³ᵉ, R³ᵉ¹, R³ᶠ, R³ᶠ¹, R³ᶠ², R³ᵍ, R³ᵍ¹, Rᵃ³, Rᵃ⁴, Rᵃ⁵, Rᵃ⁶, Rᵃ⁷, Rᵃ⁸, Rᵃ⁹ and Rᵃ¹⁰, and substituents in the substituted $C_{2-8}$ alkenyl, substituted $C_{2-8}$ alkynyl, substituted $C_{3-10}$ cycloalkyl, substituted $C_{2-8}$ heterocycloalkyl, substituted $C_{4-8}$ cycloalkenyl, substituted $C_{6-20}$ aryl, and substituted $C_{2-10}$ heteroaryl in R³, R³¹, R³², R³³, R³ᵃ, R³ᵃ¹, R³ᵇ, R³ᵇ¹, R³ᶜ, R³ᶜ¹, R³ᶜ², R³ᵈ, R³ᵈ¹, R³ᵈ², R³ᵉ, R³ᵉ¹, R³ᶠ, R³ᶠ¹, R³ᶠ², R³ᵍ and R³ᵍ¹ are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —ORᵃ¹⁵, —SRᵃ¹⁶, —C(O)ORᵃ¹⁷, —CORᵃ¹⁸, —C(O)NH₂, $C_{3-10}$ cycloalkyl, $C_{2-8}$ heterocycloalkyl, $C_{6-20}$ aryl or $C_{2-10}$ heteroaryl; Rᵃ¹⁵, Rᵃ¹⁶, Rᵃ¹⁷ and Rᵃ¹⁸ are each independently hydrogen or $C_{1-6}$ alkyl; when there are multiple substituents, the substituents are the same or different;

R⁴ is hydrogen, cyano, $C_{1-6}$ alkyl, $C_{3-10}$ cycloalkyl, $C_{2-8}$ heterocycloalkyl, —C(O)ORᵃ¹⁹ or $C_{1-6}$ alkyl substituted with —ORᵃ²⁰; Rᵃ¹⁹ and Rᵃ²⁰ are each independently $C_{1-6}$ alkyl;

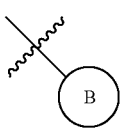

R⁵, R⁵¹, R⁵ᵃ, R⁵ᵃ¹, R⁵ᵃ², R⁵ᵇ, R⁵ᵇ¹, R⁵ᶜ, R⁵ᶜ¹, R⁵ᶜ², R⁵ᵈ, R⁵ᵈ¹, R⁵ᵈ², R⁵ᵉ, R⁵ᵉ¹ and R⁵ᵉ², are each independently hydrogen, deuterium or halogen;

R⁶, R⁶ᵃ, R⁶ᵇ, R⁶ᶜ, R⁶ᵈ and R⁶ᵉ are each independently hydrogen, deuterium, halogen, sulfonyl, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, substituted or unsubstituted $C_{2-10}$ heteroaryl, cyano, —OR⁶¹, —SR⁶², —NRᵃ⁶³Rᵃ⁶⁴, —C(O)R⁶⁵, —C(O)OR⁶⁶, —OC(O)R⁶⁷, —OC(O)OR⁶⁸, —(O)NRᵃ⁶⁹Rᵃ⁶¹⁰, —N(R⁶¹¹)C(O)R⁶¹², —S(O)R⁶¹³, —S(O)₂R⁶¹⁴ —S(O)₂NRᵃ⁶¹⁵Rᵃ⁶¹⁶, —OC(O)NRᵃ⁶¹⁷Rᵃ⁶¹⁸, —N(R⁶¹⁹)C(O)R⁶²⁰, —N(R⁶²¹)C(O)NRᵃ⁶²²Rᵃ⁶²³, —N(R⁶²⁴)S(O)₂R⁶²⁵ or —OP(O)(OR⁶²⁶)₂;

R⁶¹, R⁶², Rᵃ⁶⁴, R⁶⁵, R⁶⁶, R⁶⁷, R⁶⁸, Rᵃ⁶¹⁰, R⁶¹¹, R⁶¹², R⁶¹³, R⁶¹⁴, Rᵃ⁶¹⁵, Rᵃ⁶¹⁶, Rᵃ⁶¹⁷, Rᵃ⁶¹⁸, R⁶¹⁹, R⁶²⁰, R⁶²¹, Rᵃ⁶²², Rᵃ⁶²³, R⁶²⁴, R⁶²⁵ and R⁶²⁶ are each independently hydrogen, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

Rᵃ⁶³ and Rᵃ⁶⁹ are each independently hydrogen, hydroxyl, $C_{1-6}$ alkoxy, substituted or unsubstituted $C_{1-6}$ alkyl, substituted or unsubstituted $C_{2-8}$ alkenyl, substituted or unsubstituted $C_{2-8}$ alkynyl, Substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

in $R^6$, $R^{6a}$, $R^{6b}$, $R^{6c}$, $R^{6d}$ and $R^{6e}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl, and substituted $C_{2-10}$ heteroaryl are each independently one or more of the following groups: deuterium, halogen, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, cyano, —$OR^{71}$, —$SR^{72}$, —$NR^{a73}R^{a74}$, —$C(O)R^{75}$, —$C(O)OR^{76}$, —$C(O)R^{77}$, —$OC(O)OR^{78}$, —$C(O)NR^{a79}R^{a710}$, —$N(R^{711})C(O)R^{712}$, $S(O)R^{713}$, —$S(O)_2R^{714}$, —$S(O)_2NR^{a715}R^{a716}$, —$OC(O)NR^{a717}R^{a718}$, —$N(R^{719})C(O)OR^{720}$, —$N(R^{721})C(O)NR^{a722}R^{a723}$, —$NR^{724})S(O)_2R^{725}$ or —$OP(O)(OR^{726})_2$; when there are multiple substituents, the substituents are the same or different; $R^{71}$, $R^{72}$, $R^{a73}$, $R^{a74}$, $R^{75}$, $R^{76}$, $R^{77}$, $R^{78}$, $R^{a79}$, $R^{a710}$, $R^{711}$, $R^{712}$, $R^{713}$, $R^{714}$, $R^{a715}$, $R^{a716}$, $R^{a717}$, $R^{a718}$, $R^{719}$, $R^{720}$, $R^{721}$, $R^{a722}$, $R^{a723}$, $R^{724}$, $R^{725}$ and $R^{726}$ are each independently deuterium, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl;

in $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl or substituted $C_{2-10}$ heteroaryl are one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, —$OR^c$, —$SR^{c1}$, —$NR^{b1}R^{b2}$, —$C(O)R^{c2}$, —$C(O)OR^{c3}$, —$OC(O)R^{c4}$, —$OC(O)OR^{c5}$, —$C(O)NR^{b3}R^{b4}$,—$N(R^{c6})C(O)OR^{c7}$, $S(O)R^{c8}$, —$S(O)_2R^{c9}$, —$S(O)_2NR^{b5}R^{b6}$, —$N(R^{c10})c(O)R^{c11}$, —$N(R^{c12})C(O)NR^{b7}R^{b8}$ or —$N(R^{c13})S(O)_2R^{c14}$, $R^c$, $R^{c1}$, $R^{b1}$, $R^{b2}$, $R^{c2}$, $R^{c3}$, $R^{c4}$, $R^{c5}$, $R^{b3}$, $R^{b4}$, $R^{c6}$, $R^{c7}$, $R^{c8}$, $R^{c9}$, $R^{b5}$, $R^{b6}$, $R^{c10}$, $R^{c11}$, $R^{c12}$, $R^{b7}$, $R^{b8}$, $R^{c13}$ and $R^{c14}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

$R^7$, $R^8$, $R^9$, $R^{10}$, $R^{11}$, $R^{12}$ and $R^{13}$ are each independently hydrogen, deuterium or halogen;

one of $R^1$ and $R^2$ is hydrogen, deuterium, halogen, or substituted or unsubstituted $C_{1-6}$ alkyl, and the other is hydrogen, deuterium, halogen, cyano, sulfonyl, substituted or unsubstituted $C_{1-6}$ alkyl, —$C(O)OR^{91}$, —$COR^{92}$,

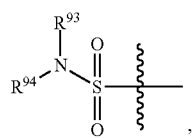

—$S(O)R^{95}$, —$S(O)_2R^{96}$, —$C(O)NR^{97}R^{98}$, or substituted or unsubstituted $C_{2-10}$ heteroaryl; in $R^1$ and $R^2$, substituents in the substituted $C_{1-6}$ alkyl and the substituted $C_{2-10}$ heteroaryl are each independently one or more of the following groups: deuterium, halogen, cyano, $C_{1-6}$ alkyl, $C_{2-8}$ alkenyl, $C_{2-8}$ alkynyl, —$OR^{920}$, —$SR^{921}$, —$C(O)OR^{922}$, —$COR^{923}$, —$C(O)NH_2$, —$NR^{924}R^{925}$, $C_{3-10}$ cycloalkyl, $C_{2-8}$ heterocycloalkyl, $C_{6-20}$ aryl or $C_{2-10}$ heteroaryl; $R^{921}$, $R^{922}$, $R^{923}$, $R^{924}$ and $R^{925}$ are each independently hydrogen or $C_{1-6}$ alkyl, wherein $R^1$ is not cyano;

$R^{91}$, $R^{92}$, $R^{93}$ and $R^{94}$ are independently one or more of the following groups hydrogen, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C^{2-10}$ heteroaryl; $R^{95}$ and $R^{96}$ are independently hydrogen or $C_{1-6}$ alkyl; $R^{97}$ and $R^{98}$ are independently hydroxyl, hydrogen, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

in $R^{97}$ and $R^{98}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl, and substituted $C_{2-10}$ heteroaryl are each independently one or more of the following groups: deuterium, halogen, cyano, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, —$OR^{101}$, —$SR^{102}$, —$NR^{b103}R^{b104}$, —$C(O)R^{105}$, —$C(O)OR^{106}$, —$OC(O)R^{107}$, —$OC(O)OR^{108}$, —$C(O)NR^{b109}R^{b1010}$, —$N(R^{1011})C(O)OR^{1012}$, $S(O)R^{1013}$, —$S(O)_2R^{1014}$, —$S(O)_2NR^{b1015}Rb^{1016}$, —$N(R^{1017})C(O)OR^{1018}$, —$OC(O)NR^{b1019}R^{b1020}$, —$N(R^{1021})S(O)_2R^{1022}$; when there are multiple substituents, the substituents are the same or different; $R^{101}$, $R^{102}$, $R^{b103}$, $R^{b104}$, $R^{105}$, $R^{106}$, $R^{107}$, $R^{108}$, $R^{b109}$, $R^{b1010}$, $R^{1011}$, $R^{1012}$, $R^{1013}$, $R^{1014}$, $R^{b1015}$, $R^{b1016}$, $R^{1017}$, $R^{1018}$, $R^{b1019}$, $R^{b1020}$, $R^{1021}$ and $R^{1022}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

or $R^1$ and $R^2$ together with the carbon atom to which they are attached form substituted or unsubstituted 4-8 membered cycloalkenyl, or a substituted or unsubstituted 4-8 membered heterocycle, and the heteroatoms in the 4-8 membered heterocycle are one or more of O, S and N, and the number of the heteroatoms is 1, 2, 3 or 4;

substituents in the substituted 4-8 membered cycloalkenyl and the substituted 4-8 membered heterocycle are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{111}$, —$SR^{112}$, —$C(O)OR^{113}$, —$COR^{114}$, —$C(O)NH_2$, $C_{3-10}$ cycloalkyl, $C_{2-8}$ heterocycloalkyl, $C_{6-20}$ aryl or $C_{2-10}$ heteroaryl; $R^{111}$, $R^{112}$, $R^{113}$ and $R^{114}$ are each independently hydrogen or $C_{1-6}$ alkyl;

in each of the above letters and groups, the heteroatoms in the substituted or unsubstituted $C_{2-8}$ heterocycloalkyl or the $C_{2-8}$ heterocycloalkyl are one or more of N, O and S, and the number of the heteroatoms is 1, 2, 3 or 4; the heteroatoms in the substituted or unsubstituted $C_{2-10}$ heteroaryl or the $C_{2-10}$ heteroaryl are one or more of N, O and S, and the number of the heteroatoms is 1, 2, 3 or 4; when there are multiple heteroatoms, the heteroatoms are the same or different;

or in the above groups or substituents, when $NR^XR^Y$ is present, then $R^X$ and $R^Y$ together with the nitrogen atom to which they are attached form substituted or unsubstituted 3-8 membered heterocyclyl; the heteroatoms in the 3-8 membered heterocyclyl are N, N and O, N and S, or N, O and S; the number of the heteroatoms is 1, 2, 3 or 4; the substituents in the substituted 3-8 membered heterocyclyl are one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{a81}$, —$SR^{a82}$, —$C(O)OR^{a83}$, —$COR^{a84}$, —$C(O)NH_2$, $C_{3-10}$ cycloalkyl, $C_{2-8}$ heterocycloalkyl, $C_{6-20}$ aryl or $C_{2-10}$ heteroaryl; $R^{a81}$, $R^{a82}$, $R^{a83}$ and $R^{a84}$ are each independently hydrogen or $C_{1-6}$ alkyl; $NR^XR^Y$ is —$NR^{a3}R^{a4}$, —$NR^{a8}R^{a9}$, —$NR^{a63}R^{a64}$, —$NR^{a69}R^{a610}$, —$NR^{a615}R^{a616}$, —$NR^{a617}R^{a618}$, —$NR^{a622}R^{a623}$, —$NR^{a73}R^{a74}$, —$NR^{a79}R^{a710}$, —$NR^{a715}R^{a716}$, —$NR^{a717}R^{a718}$, —$NR^{a722}R^{a723}$, —$NR^{b1}R^{b2}$, —$NR^{b3}R^{b4}$, —$NR^{b5}R^{b6}$, —$NR^{b7}R^{b8}$, —$NR^{93}R^{94}$, —$NR^{97}R^{98}$, —$NR^{924}R^{925}$, —$NR^{b103}R^{b104}$, —$NR^{b109}R^{b1010}$, —$NR^{b1015}R^{b1016}$ or —$NR^{b1019}R^{b1020}$.

2. The aromatic heterocyclic substituted olefin compound represented by general formula I or the pharmaceutically acceptable salt thereof as defined in claim 1, wherein
   the $C_{1-6}$ alkyl in the substituted or unsubstituted $C_{1-6}$ alkyl and the $C_{1-6}$ alkyl are independently $C_{1-4}$ alkyl;
   and/or, the $C_{2-8}$ alkenyl in the substituted or unsubstituted $C_{2-8}$ alkenyl and the $C_{2-8}$ alkenyl are independently $C_{2-4}$ alkenyl;
   and/or, the $C_{2-8}$ alkynyl in the substituted or unsubstituted $C_{2-8}$ alkynyl and the $C_2$-alkynyl are independently $C_{2-4}$ alkynyl;
   and/or, the $C_{3-10}$ cycloalkyl in the substituted or unsubstituted $C_{3-10}$ cycloalkyl and the $C_{3-10}$ cycloalkyl are independently cyclopropyl, cyclobutyl, cyclopentyl, cyclohexyl, cycloheptyl, cyclooctyl, cyclononyl, cyclodecyl, bicyclo[3.1.1]heptyl, bicyclo[2.2.1]heptyl, bicyclo[2.2.2]octyl, Bicyclo[3.2.2]nonyl, bicyclo[3.3.1]nonyl or bicyclo[4.2.1]nonyl;
   and/or, the $C_{2-8}$ heterocycloalkyl in the substituted or unsubstituted $C_{2-8}$ heterocycloalkyl and the $C_{2-8}$ heterocycloalkyl are independently azetidinyl, azepanyl, aziridine, diazacycloheptyl, 1,3-dioxanyl, 1,3-dioxopenyl, 1,3-dithiopentyl, 1,3-dithianyl, imidazolinyl, imidazolidinyl, isothiazolidinyl, isothiazolyl, isoxazolinyl, morpholinyl, oxadiazolinyl, oxadiazole alkyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxothiomorpholinyl, thiopyranyl, trithianyl, 2,3-dihydrobenzofuran-2-yl, 2,3-dihydrobenzofuran-3-yl, dihydroindole-1-yl, indoline-2-yl, dihydroindole-3-yl, 2,3-dihydrobenzothiophen-2-yl, decahydroquinolinyl, decahydroisoquinolinyl, octahydro-1H-indolyl or octahydrobenzofuranyl;
   and/or, the $C_{4-8}$ cycloalkenyl in the substituted or unsubstituted $C_{4-8}$ cycloalkenyl and the $C_{4-8}$ cycloalkenyl are independently cyclobutenyl, cyclopentenyl, cyclohexenyl, cycloheptenyl, cyclooctenyl, norbornenyl or bicyclo[2.2.2]octenyl;
   and/or, the $C_{6-20}$ aryl in the substituted or unsubstituted $C_{6-20}$ aryl or the $C_{6-20}$ aryl is independently phenyl, naphthyl, anthryl, phenanthryl, azulenyl, indan-1-yl, indan-2-yl, indan-3-yl, indan-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalene-2-yl, dihydronaphthalene-3-yl, dihydronaphthalene-4-yl, dihydronaphthalene-1-yl, 5,6,7,8-tetrahydronaphthalene-1-yl, 5,6,7,8-tetrahydronaphthalene-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-benzofuran-2-one-5-yl, 2H-benzofuran-2-one-6-yl, 2H-benzofuran-2-one-7-yl, 2H-benzofuran-2-one-8-yl, isoindoline-1,3-dione-4-yl, isoindoline-1,3-dione-5-yl, inden-1-one-4-yl, inden-1-one-5-yl, inden-1-one-6-yl, inden-1-one-7-yl, 2,3-dihydrobenzo[b][1,4]dioxan-5-yl, 2,3-dihydrobenzo[b][1,4]dioxan-6-yl, 2H-benzo[b][1,4]oxazepine 3(4H)-keto-5-yl, 2H-benzo[b][1,4]oxazepine 3(4H)-one-6-yl, 2H-benzo[b][1,4]oxazepine 3(4H)-keto-7-yl, 2H-benzo[b][1,4]oxazepine 3(4H)-one-8-yl, benzo[d]oxazepine-2(3H)-one-5-yl, benzo[d]oxazepine-2(3H)-one-6-yl, benzo[d]oxazepine-2(3H)-one-7-yl, benzo[d]oxazepine-2(3H)-one-8-yl, quinazoline-4(3H)-one-5-yl, quinazoline-4(3H)-one-6-yl, quinazoline-4(3H)-one-7-yl, quinazoline-4(3H)-one-8-yl, quinoxaline-2(1H)-one-5-yl, quinoxaline-2(1H)-one-6-yl, quinoxaline-2(1H)-one-7-yl, quinoxaline-2(1H)-one-8-yl, benzo[d]thiazole-2(3H)-one-4-yl, benzo[d]thiazole-2(3)-one-5-yl, benzo[d]thiazole-2(3H)-one-6-yl or benzo[d]thiazole-2(3H)-one-7-yl;
   and/or, the $C_{2-10}$ heteroaryl in the substituted or unsubstituted $C_{2-10}$ heteroaryl and the $C_{2-10}$ heteroaryl are independently furanyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzothiazolyl, cinnolinyl, 5,6-dihydroquinolin-2-yl, 5,6-dihydroquinolin-1-yl, furopyridinyl, indazolyl, indolyl, isoquinolinyl, naphthyridinyl, purinyl, quinolinyl, 5,6,7,8-tetrahydroquinoline-2-yl, 5,6,7,8-tetrahydroquinoline-3-yl, 5,6,7,8-tetrahydroquinoline-4-yl, 5,6,7,8-tetrahydroisoquinoline-1-yl, thienopyridyl, 4,5,6,7-tetrahydro[c][1,2,5]oxadiazolyl or 6,7-dihydropyro [c][1,2,5]oxadiazole-4(5H)keto.

3. The aromatic heterocyclic substituted olefin compound represented by general formula I or the pharmaceutically acceptable salt thereof as defined in claim 1, wherein
   one of $R^1$ and $R^2$ is hydrogen, or substituted or unsubstituted $C_{1-6}$ alkyl, and the other is hydrogen, cyano, sulfonyl, substituted or unsubstituted $C_{1-6}$ alkyl, —$C(O)OR^{91}$, —$COR^{92}$,

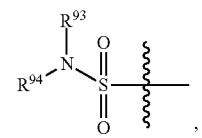

—$S(O)R^{95}$, —$S(O)_2R^{96}$, —$C(O)NR^{97}R^{98}$, or substituted or unsubstituted $C_{2-10}$ heteroaryl; or $R^1$ and $R^2$ together with the carbon atom to which they are attached form substituted or unsubstituted 4-8 membered cycloalkenyl, or a substituted or unsubstituted 4-8 membered heterocycle; wherein, definitions of $R^{91}$, $R^{92}$, $R^{93}$, $R^{94}$, $R^{95}$, $R^{96}$, $R^{97}$ and $R^{98}$ are the same as defined in claim 1; definitions of the substitutions in the substituted $C_{1-6}$ alkyl, the substituted $C_{2-10}$ heteroaryl, the substituted 4-8 membered cycloalkenyl and the substituted 4-8 membered heterocycle are the same as defined in claim 1;
   and/or, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —$NR^{a3}R^{a4}$, —$OR^{a5}$, —$SR^{a6}$, —$C(O)OR^{a7}$, —$C(O)NR^{a8}R^{a9}$, —$COR^{a10}$, substituted or unsubstituted $C_{1-6}$ alkyl, substituted or unsubstituted $C_{2-8}$ heterocycloalkyl, substituted or unsubstituted $C_{6-20}$ aryl, or substituted or unsubstituted $C_{2-10}$ heteroaryl; wherein, the definitions of $R^{a3}$, $R^{a4}$, $R^{a5}$, $R^{a6}$, $R^{a7}$, $R^{a8}$, $R^{a9}$ and $R^{a10}$ are the same as defined in claim 1; definitions of the substitutions in the substituted $C_{1-6}$ alkyl, substituted $C_{2-8}$ heterocycloalkyl, substituted $C_{6-20}$ aryl or substituted $C_{2-10}$ heteroaryl are the same as defined in claim 1;

and/or, $R^4$ is hydrogen, $C_{1-6}$ alkyl or $C_{3-10}$ cycloalkyl;

and/or, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen;

and/or, $R^6$, $R^{6a}$, $R^{6b}$, $R^{6c}$, $R^{6d}$ and $R^{6e}$ are each independently hydrogen, halogen, cyano, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, cyano, —$OR^{61}$, —$SR^{62}$, —$C(O)R^{65}$, —$C(O)OR^{66}$ or —$C(O)NR^{a69}R^{a610}$, definitions of $R^{61}$, $R^{62}$, $R^{65}$, $R^{66}$, $R^{a69}$ and $R^{a610}$ are the same as defined in claim 1; definitions of the substitutions in the substituted $C_{1-6}$ alkyl, substituted $C_{2-8}$ heterocycloalkyl, substituted $C_{6-20}$ aryl or substituted $C_{2-10}$ heteroaryl are the same as defined in claim 1.

4. The aromatic heterocyclic substituted olefin compound represented by general formula I or the pharmaceutically acceptable salt thereof as defined in claim 1, wherein one of $R^1$ and $R^2$ is hydrogen, and the other is hydrogen, cyano, substituted or unsubstituted $C_{1-6}$ alkyl, —$C(O)OR^{91}$ or —$C(O)NR^{97}R^{98}$, wherein $R^1$ is not cyano; or $R^1$ and $R^2$ together with the carbon atom to which they are attached form substituted or unsubstituted 4-8 membered cycloalkenyl; wherein $R^{91}$ is hydrogen or $C_{1-6}$ alkyl; $R^{97}$ and $R^{98}$ are independently hydrogen, or substituted or unsubstituted $C_{1-6}$ alkyl; or $R^{97}$ and $R^{98}$ together with the nitrogen atom to which they are attached form substituted or unsubstituted 3-8 membered heterocyclyl; wherein in $R^1$ or $R^2$, definitions of the substitutions in the substituted $C_{1-6}$ alkyl, the substituted 4-8 membered cycloalkenyl and the substituted 4-8 membered heterocycle are the same as defined in claim 1; in $R^{97}$ or $R^{98}$, definitions of the substituents in the substituted $C_{1-6}$ alkyl or the substituted 3-8 membered heterocyclyl are the same as defined in claim 1;

and/or, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, —$OR^{a5}$, or substituted or unsubstituted $C_{1-6}$ alkyl; $R^{a5}$ is $C_{1-6}$ alkyl; the substituents in the substituted $C_{1-6}$ alkyl are one or more of the following groups: deuterium or halogen;

and/or, $R_4$ is hydrogen, $C_{1-6}$ alkyl or $C_{3-10}$ cycloalkyl;

and/or, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen;

and/or, $R^6$, $R^{6a}$, $R^{6b}$, $R^{6c}$, $R^{6d}$ and $R^{6e}$ are each independently cyano, —$C(O)OR^{66}$ or —$C(O)NR^{a69}R^{a610}$, wherein $R^{66}$ is $C_{1-6}$ alkyl; $R^{a69}$ and $R^{a610}$ are each independently hydrogen, substituted or unsubstituted $C_{1-6}$ alkyl, substituted or unsubstituted $C_{3-10}$ cycloalkyl or —$OR^{627}$;

definitions of the substitutions in the substituted $C_{1-6}$ alkyl or the substituted $C_{3-10}$ cycloalkyl are the same as defined in claim 1; a definition of $R^{627}$ is the same as defined in claim 1.

5. The aromatic heterocyclic substituted olefin compound represented by general formula I or the pharmaceutically acceptable salt thereof as defined in claim 1, wherein one of $R^1$ and $R^2$ is hydrogen, and the other is hydrogen, $C_{1-6}$ alkyl, —$C(O)OR^{91}$ or —$C(O)NR^{97}R^{98}$; or $R^1$ and $R^2$ together with the carbon atom to which they are attached form 4-8 membered cycloalkenyl; wherein $R^{91}$, $R^{97}$ and $R^{98}$ are independently hydrogen or $C_{1-6}$ alkyl; or $R^{97}$ and $R^{98}$ together with the nitrogen atom to which they are attached form 3-8 membered heterocyclyl;

and/or, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, trifluoromethyl, difluoromethyl, methyl, deuterated methyl or methoxy; one or two positions in ring A are not hydrogen; and/or $R^4$ is hydrogen, $C_{1-6}$ alkyl or $C_{3-10}$ cycloalkyl;

and/or, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen;

and/or, $R^6$, $R^{6a}$, $R^{6b}$, $R^{6c}$, $R^{6d}$ and $R^{6e}$ are each independently cyano, —$C(O)OR^{66}$ or —$C(O)NR^{a69}R^{a610}$, wherein $R^{66}$ is $C_{1-6}$ alkyl; $R^{a69}$ and $R^{a610}$ are each independently hydrogen, substituted or unsubstituted $C_{1-6}$ alkyl, $C_{3-10}$ cycloalkyl or —$OR^{627}$; the substituents in the substituted $C_{1-6}$ alkyl are $C_{2-8}$ heterocycloalkyl; $R^{627}$ is $C_{2-8}$ heterocycloalkyl.

6. The aromatic heterocyclic substituted olefin compound represented by general formula I or the pharmaceutically acceptable salt thereof as defined in claim 1, wherein $R^1$ is hydrogen, and $R^2$ is hydrogen, $C_{1-6}$ alkyl, —$C(O)OR^{91}$ or —$C(O)NR^{97}R^{98}$; $R^{91}$, $R^{97}$ and $R^{98}$ are independently hydrogen or $C_{1-6}$ alkyl;

and/or ring A is

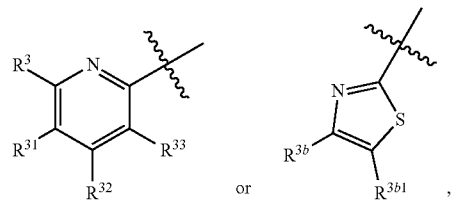

wherein $R^3$ and $R^{33}$ are independently hydrogen, halogen, —$OR^{a5}$, or substituted or unsubstituted $C_{1-6}$ alkyl, but not hydrogen at the same time; $R^{3b}$ is hydrogen, halogen, —$OR^{a5}$, or substituted or unsubstituted $C_{1-6}$ alkyl; a definition of $R^{a5}$ is the same as defined in claim 1; definitions of the substitutions in the substituted $C_{1-6}$ alkyl are the same as defined in claim 1; $R^{31}$, $R^{32}$ and $R^{3b1}$ are hydrogen;

and or

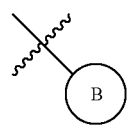

is

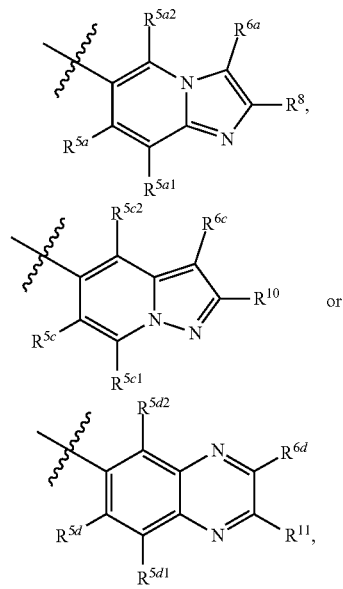

wherein $R^{5a}$, $R^{5a1}$, $R^{5a2}$, $R^{5c}$, $R^{5c1}$, $R^{5c2}$, $R^{5d}$, $R^{5d1}$, $R^{5d2}$, $R^{10}$ and $R^{11}$ are hydrogen; $R^{6a}$, $R^{6c}$ and $R^{6d}$ are each independently cyano, $C_{2-10}$ heteroaryl, —C(O)OR$_{66}$ or —C(O)NR$^{a69}$R$^{a610}$, wherein definitions of $C_{2-10}$ heteroaryl, $R^{66}$, $R^{a69}$ and $R^{a610}$ are the same as defined in claim 1.

7. The aromatic heterocyclic substituted olefin compound represented by general formula I or the pharmaceutically acceptable salt thereof as defined in claim 1, wherein $R^1$ and $R^2$ are both hydrogen;

or $R^1$ is hydrogen, $R^2$ is

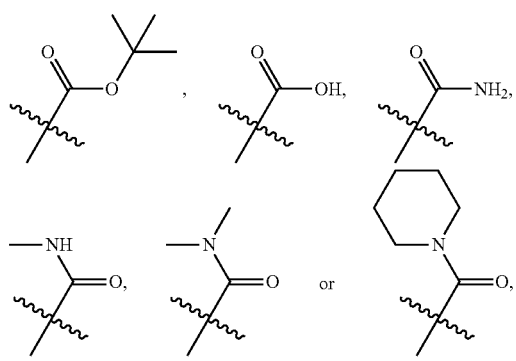

or $R^1$ and $R^2$ together with the carbon atom to which they are attached form cyclohexene;

and/or

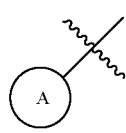

is

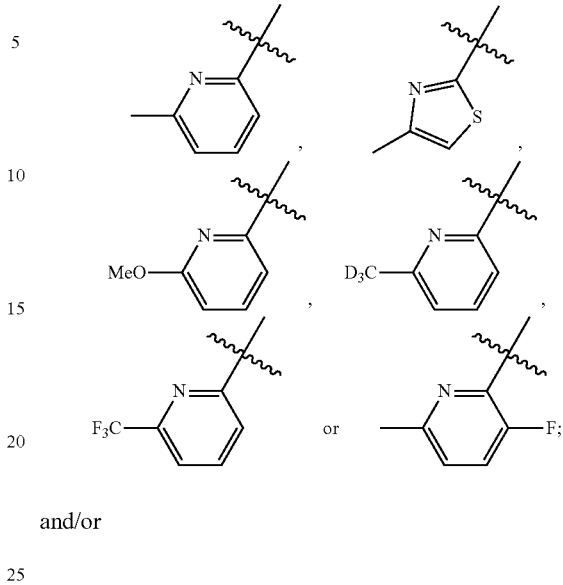

and/or

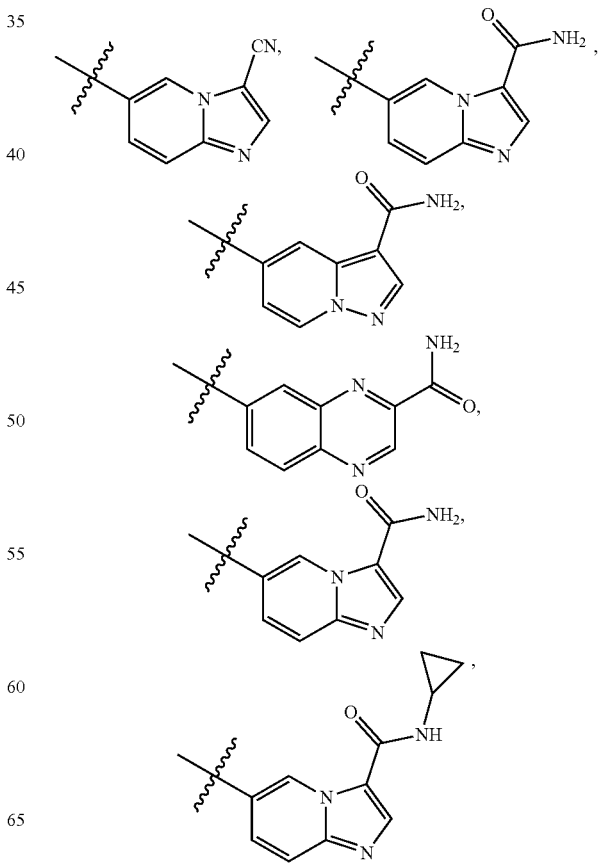

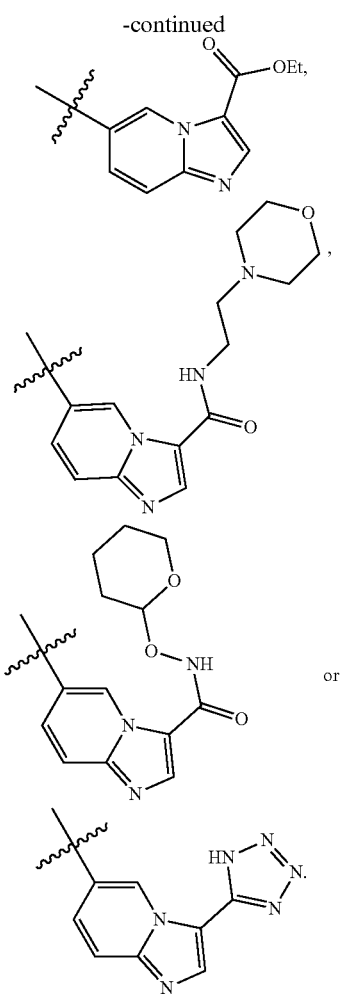
8. The aromatic heterocyclic substituted olefin compound represented by general formula I or the pharmaceutically acceptable salt thereof as defined in claim 1, wherein the aromatic heterocyclic substituted olefin compound represented by general formula I is any one of the following compounds:
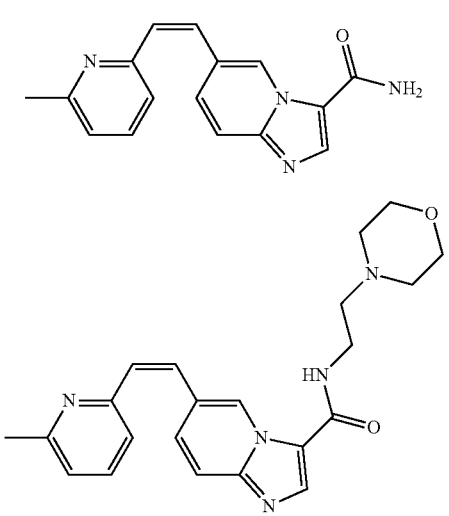
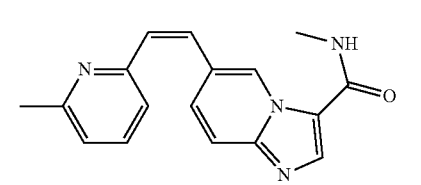
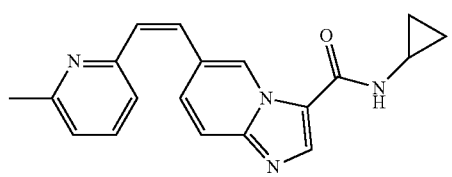
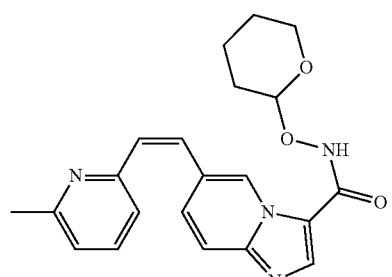
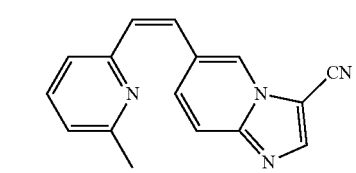
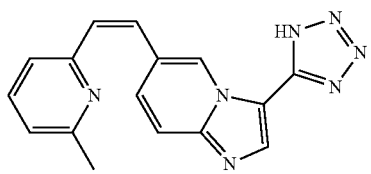
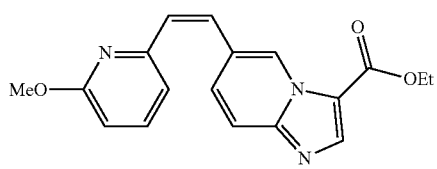
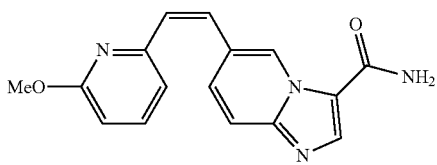
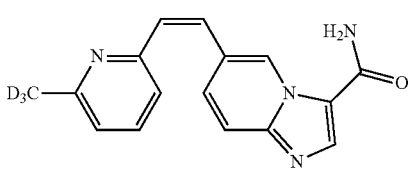

11
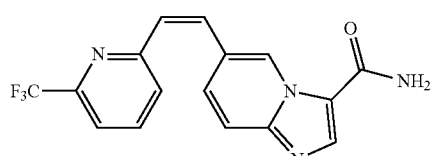
12
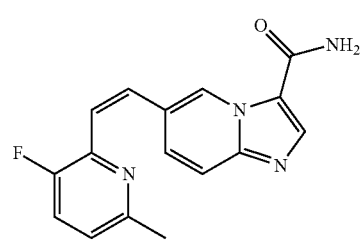
13
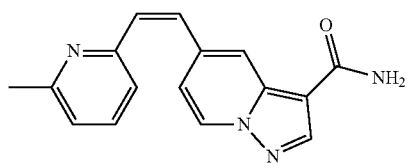
14
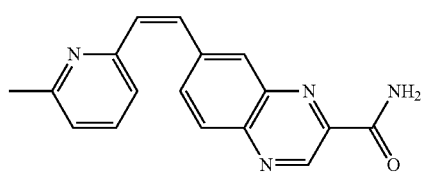
15
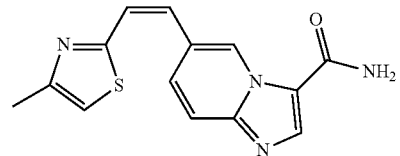
16
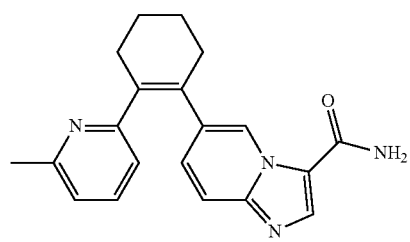
17a
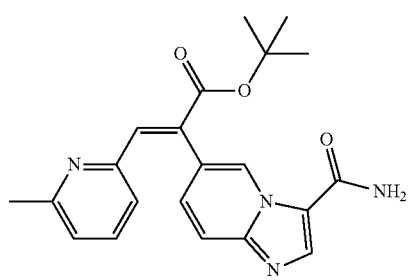
17b
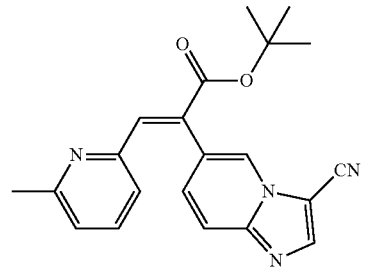
17c
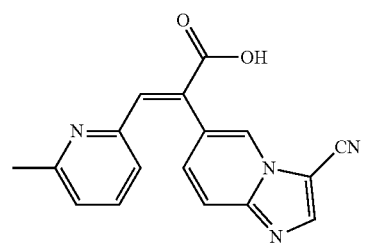
17
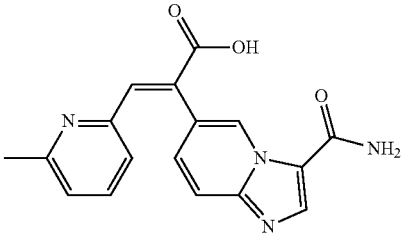
18a
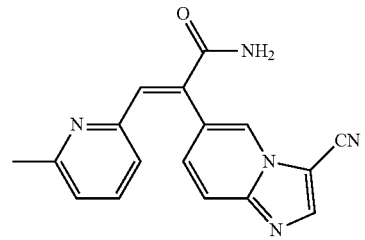
18
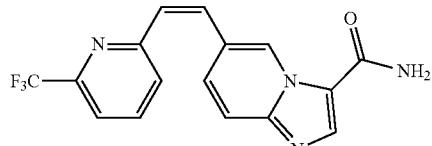
19a
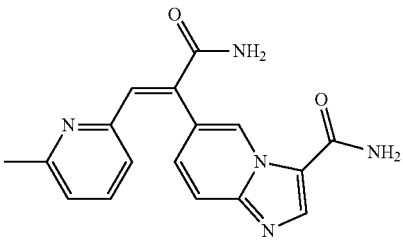

-continued

19
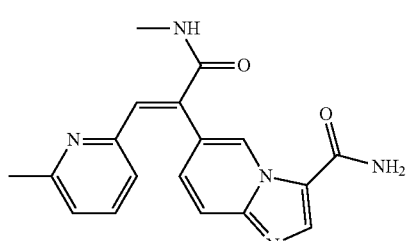

20a
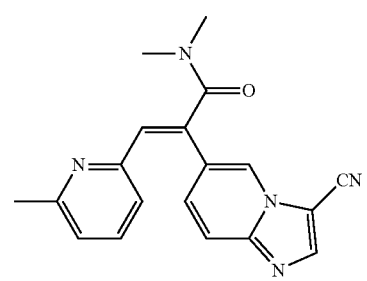

20
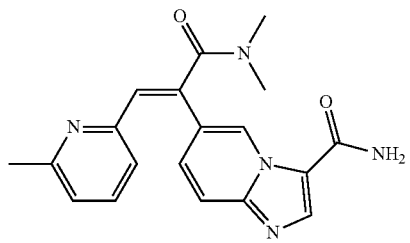

21a
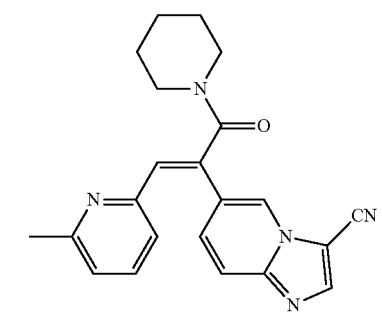

9-a
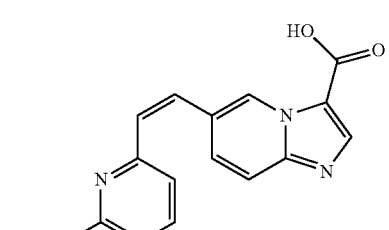

21
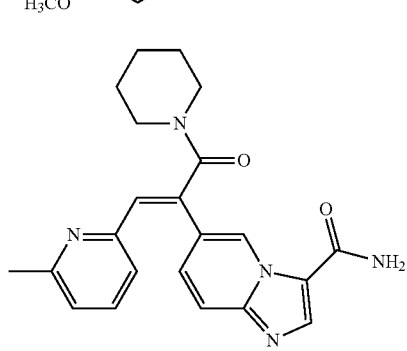

-continued

22
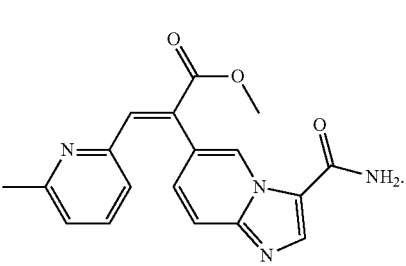

9. A method for preparing the aromatic heterocyclic substituted olefin compound represented by general formula I as defined in claim 1, comprising any one of the following methods:

method I, comprising the following steps of: conducting a coupling reaction of compound II-A with compound II-2 as shown below;

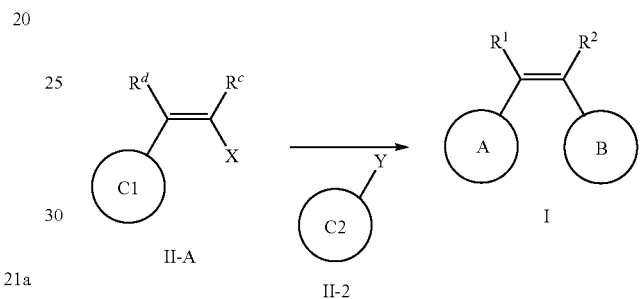

wherein one of X and Y is halogen; the other is an organotin reagent or an organoboron reagent; one of ring C1 and ring C2 is ring A, and the other is ring B; one of $R^d$ and $R^c$ is $R^1$, and the other is $R^2$; when ring C1 is ring A, then $R^d$ is $R^1$ definitions of $R^1$, $R^2$, ring A and ring B are the same as defined in claim 1;

method II, comprising the following steps of: conducting a reaction of compound III-1 to obtain a compound represented by general formula I, wherein in compound III-1, EWG2 is an electron withdrawing group that can be converted into R1 or R2;

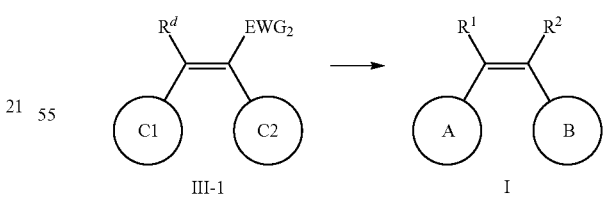

one of ring C1 and ring C2 is ring A, and the other is ring B; one of $R^d$ and $R^c$ is $R^1$ and the other is $R^2$; when ring C1 is ring A, then $R^d$ is $R^1$; definitions of $R^1$, $R^2$, ring A and ring B are the same as defined in claim 1; or method III, comprising the following steps of: hydrogenolyzing compound I-1 under the action of a palladium reagent;

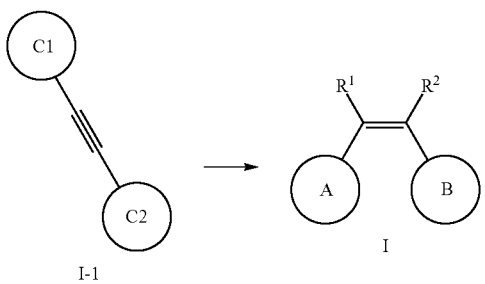

wherein $R^1$ and $R^2$ are hydrogen, one of ring C1 and ring C2 is ring A, and the other is ring B; wherein definitions of ring A and ring B are the same as defined in claim 1.

10. A method for inhibiting ALK 5 activity, or treating ALK5-mediated diseases comprising administering an effective amount of the aromatic heterocyclic substituted olefin compound represented by general formula I or the pharmaceutically acceptable salt thereof as defined in claim 1 to the subject.

11. The method as defined in claim 10, wherein the ALK5-mediated diseases are one or more of cancer, organ fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, arteriosclerosis, and tumor metastasis and growth.

12. A pharmaceutical composition, comprising one or more of the aromatic heterocyclic substituted olefin compound represented by general formula I and the pharmaceutically acceptable salt thereof as defined in claim 1, and a pharmaceutically acceptable carrier.

13. The method as defined in claim 11, wherein the cancer is one or more of colon cancer, pancreatic cancer, breast cancer, prostate cancer, lung cancer, brain cancer, ovarian cancer, cervical cancer, testicular cancer, kidney cancer, head or neck cancer, bone cancer, skin cancer, rectal cancer, liver cancer, colon cancer, esophageal cancer, gastric cancer, pancreatic cancer, thyroid cancer, bladder cancer, lymphoma, leukemia and melanoma; and/or
the organ fibrosis is one or more of renal fibrosis, liver fibrosis and lung fibrosis.

14. The aromatic heterocyclic substituted olefin compound represented by general formula I or the pharmaceutically acceptable salt thereof as defined in claim 2, wherein
the $C_{1-6}$ alkyl in the substituted or unsubstituted $C_{1-6}$ alkyl and the $C_{1-6}$ alkyl are independently $C_{1-4}$ alkyl; the $C_{1-4}$ alkyl is methyl, ethyl, n-propyl, isopropyl, n-butyl, isobutyl, or tent-butyl;

and/or, the $C_{2-8}$ alkenyl in the substituted or unsubstituted $C_{2-8}$ alkenyl and the $C_{2-8}$ alkenyl are independently C2-4 alkenyl; the C2-4 alkenyl is vinyl, propenyl, allyl,

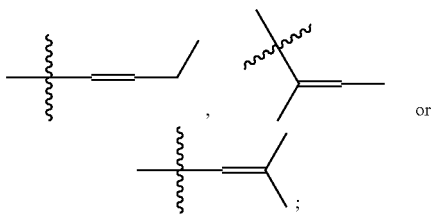

and/or, the $C_{2-8}$ alkynyl in the substituted or unsubstituted $C_{2-8}$ alkynyl and the $C_{2-8}$ are independently $C_{2-4}$ alkynyl; the $C_{2-4}$ alkynyl is ethynyl, propynyl, butynyl or 3-methylpropynyl.

* * * * *